US007736897B2

(12) United States Patent
Tao et al.

(10) Patent No.: US 7,736,897 B2
(45) Date of Patent: *Jun. 15, 2010

(54) FRT RECOMBINATION SITES AND METHODS OF USE

(75) Inventors: Yumin Tao, Urbandale, IA (US); Dennis L. Bidney, Urbandale, IA (US); William J. Gordon-Kamm, Urbandale, IA (US); Leszek A. Lyznik, Johnston, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 640 days.

This patent is subject to a terminal disclaimer.

(21) Appl. No.: 11/487,300

(22) Filed: Jul. 14, 2006

(65) Prior Publication Data
US 2008/0047031 A1    Feb. 21, 2008

Related U.S. Application Data

(60) Provisional application No. 60/700,225, filed on Jul. 18, 2005.

(51) Int. Cl.
*C12N 15/87* (2006.01)
*C12N 15/82* (2006.01)

(52) U.S. Cl. ..................................... 435/419; 536/24.2

(58) Field of Classification Search ........................ None
See application file for complete search history.

(56) References Cited

U.S. PATENT DOCUMENTS

| | | | |
|---|---|---|---|
| 5,658,772 A | 8/1997 | Odell et al. | |
| 5,744,336 A | 4/1998 | Hodges et al. | |
| 6,010,884 A | 1/2000 | Griffiths et al. | |
| 6,051,409 A | 4/2000 | Hansen et al. | |
| 6,114,600 A | 9/2000 | Ow et al. | |
| 6,175,058 B1 | 1/2001 | Baszczynski et al. | |
| 6,187,994 B1 | 2/2001 | Baszczynski et al. | |
| 6,262,341 B1 | 7/2001 | Baszczynski et al. | |
| 6,300,545 B1 | 10/2001 | Baszczynski et al. | |
| 6,331,661 B1 | 12/2001 | Baszczynski et al. | |
| 6,410,329 B1 | 6/2002 | Hansen et al. | |
| 6,455,315 B1 | 9/2002 | Baszczynski et al. | |
| 6,458,594 B1 | 10/2002 | Baszczynski et al. | |
| 6,465,254 B1 | 10/2002 | Saito et al. | |
| 6,528,700 B1 | 3/2003 | Baszczynski et al. | |
| 6,541,231 B1 | 4/2003 | Baszczynski et al. | |
| 6,552,248 B1 | 4/2003 | Baszczynski et al. | |
| 6,573,425 B1 | 6/2003 | Baszczynski et al. | |
| 6,624,297 B1 | 9/2003 | Baszczynski et al. | |
| 6,664,108 B1 | 12/2003 | Baszczynski et al. | |
| 6,696,278 B1 | 2/2004 | Carstens | |
| 6,720,475 B1 | 4/2004 | Baszczynski et al. | |
| 6,746,870 B1 | 6/2004 | Ow et al. | |
| 6,849,778 B1 | 2/2005 | Staub et al. | |
| 6,911,575 B1 | 6/2005 | Baszczynski et al. | |
| 6,992,235 B2 | 1/2006 | Bode et al. | |
| 7,060,499 B1 | 6/2006 | Saito et al. | |
| 7,074,611 B2 | 7/2006 | Chambon et al. | |
| 7,102,055 B1 | 9/2006 | Baszczynski et al. | |
| 7,126,041 B1 | 10/2006 | Helmer et al. | |
| 7,179,599 B2 | 2/2007 | Baszczynski et al. | |
| 7,179,644 B2 | 2/2007 | Farmer | |
| 7,198,924 B2 | 4/2007 | Chesnut et al. | |
| 7,223,601 B2 | 5/2007 | Baszczynski et al. | |
| 7,238,854 B2 | 7/2007 | Yadav et al. | |
| 7,244,560 B2 | 7/2007 | Chesnut et al. | |
| 7,267,979 B2 | 9/2007 | Yadav | |
| 2001/0032341 A1 | 10/2001 | Bode et al. | |
| 2002/0023278 A1 | 2/2002 | Lyznik et al. | |
| 2002/0123145 A1 | 9/2002 | Ow | |
| 2003/0119166 A1 | 6/2003 | Baszczynski et al. | |
| 2003/0226160 A1 | 12/2003 | Baszczynski et al. | |
| 2003/0226164 A1 | 12/2003 | Suttie et al. | |
| 2003/0237107 A1 | 12/2003 | Baszczynski et al. | |
| 2004/0003435 A1 | 1/2004 | Baszczynski et al. | |
| 2004/0005713 A1 | 1/2004 | Baszczynski et al. | |
| 2004/0083500 A1 | 4/2004 | Baszczynski et al. | |
| 2004/0137624 A1 | 7/2004 | Lowe | |

(Continued)

FOREIGN PATENT DOCUMENTS

EP    1 035 208 A1    5/1999

(Continued)

OTHER PUBLICATIONS

Araki, K., et al.; "Targeted integration of DNA using mutant lox sites in embryonic stem cells"; Nucleic Acids Research (1997) 25(4):868-872; Oxford University Press, Oxford, UK.

(Continued)

*Primary Examiner*—David H Kruse
*Assistant Examiner*—Li Zheng

(57) ABSTRACT

Methods and compositions using populations of randomized modified FRT recombination sites to identify, isolate and/or characterize modified FRT recombination sites are provided. The recombinogenic modified FRT recombination sites can be employed in a variety of methods for targeted recombination of polynucleotides of interest, including methods to recombine polynucleotides, assess promoter activity, directly select transformed organisms, minimize or eliminate expression resulting from random integration into the genome of an organism, such as a plant, remove polynucleotides of interest, combine multiple transfer cassettes, invert or excise a polynucleotide, and identify and/or characterize transcriptional regulating regions are also provided.

19 Claims, No Drawings

U.S. PATENT DOCUMENTS

| | | | |
|---|---|---|---|
| 2004/0261145 | A1 | 12/2004 | Lyznik et al. |
| 2005/0009182 | A1 | 1/2005 | Ow |
| 2006/0094111 | A1 | 5/2006 | Saito et al. |
| 2006/0195937 | A1 | 8/2006 | Baszczynski et al. |
| 2006/0253939 | A1 | 11/2006 | Baszczynski et al. |
| 2007/0015195 | A1 | 1/2007 | Tao et al. |

FOREIGN PATENT DOCUMENTS

| | | | |
|---|---|---|---|
| EP | 0 939 120 | A1 | 9/1999 |
| EP | 1 122 310 | A1 | 4/2000 |
| WO | 93/01283 | | 1/1993 |
| WO | 93/17116 | | 9/1993 |
| WO | 94/17176 | | 8/1994 |
| WO | 96/04393 | | 2/1996 |
| WO | 97/12046 | | 4/1997 |
| WO | 97/13401 | | 4/1997 |
| WO | 97/37012 | | 10/1997 |
| WO | 99/23202 | | 5/1999 |
| WO | 99/25821 | A1 | 5/1999 |
| WO | 99/25840 | | 5/1999 |
| WO | 99/25841 | | 5/1999 |
| WO | 99/25854 | | 5/1999 |
| WO | 99/25855 | | 5/1999 |
| WO | 99/55851 | | 11/1999 |
| WO | 01/07572 | A2 | 2/2001 |
| WO | 01/11058 | A1 | 2/2001 |
| WO | 01/23545 | A1 | 4/2001 |
| WO | 01/85969 | A2 | 11/2001 |
| WO | 02/08409 | A2 | 1/2002 |
| WO | 03/083045 | A2 | 10/2003 |

OTHER PUBLICATIONS

Baer, A., et al.; "Coping with kinetic and thermodynamic barriers: RMCE, an efficient strategy for the targeted integration of transgenes"; Current Opinion in Biotechnology (2001) 12:473-480; Elsevier Science Ltd; Amsterdam, The Netherlands.

Ow, D., et al.; "Genome Manipulation Through Site-Specific Recombination"; Critical Reviews in Plant Sciences (1995) 14(3):239-261; Taylor and Francis, London, UK.

Schlake, T., et al.; "Use of Mutated FLP Recognition Target (FRT) Sites for the Exchange of Expression Cassettes at Defined Chromosomal Loci"; Biochemistry (1994) 33:12746-12751; American Chemical Society; Washington, DC, US.

Wirth, D., et al.; "Flp-Mediated Integration of Expression Cassettes into FRT-Tagged Chromosomal Loci in Mammalian Cells"; Methods in Molecular Biology (2004) 267:467-476; Humana Press Inc., Totowa, NJ, US.

Kerbach, S., et al.; "Site-Specific recombination in *Zea mays*"; Theor Appl Genet (2005) 111:1608-1616; Springer-Verlag, Berlin/Heidelberg, Germany.

Dale, E., et al.; "Gene transfer with subsequent removal of the selection gene from the host genome"; Proc Natl Acad Sci USA (Dec. 1991) 88:10558-10562; National Academy of Sciences, Washington, DC US.

Lyznik, L.A., et al.; "Activity of yeast FLP recombinase in maize and rice protoplasts"; Nucleic Acids Research (1993) 21(4):969-975; Oxford University Press, Oxford, UK.

Proteau, G., et al.; "The minimal duplex DNA sequence required for site-specific recombination promoted by the FLP protein of yeast in vitro"; Nucleic Acids Research (1986) 14(12):4787-4802; Oxford University Press, Oxford, UK.

Senecoff, J.F., et al.; "The FLP recombinase of the yeast 2-mu m plasmid: Characterization of its recombination site"; Proc Natl Acad Sci USA (Nov. 1985) 82:7270-7274; National Academy of Sciences, Washington, DC US.

Seibler, J., et al.; "Double-Reciprocal Crossover Mediated by FLP-Recombinase: A Concept and an Assay"; Biochemistry (1997) 36:1740-1747; American Chemical Society, Washington, DC US.

Umlauf, S.W., et al.; "The functional significance of DNA sequence structure in a site-specific genetic recombination reaction"; The EMBO Journal (1988) 7(6):1845-1852; IRL Press Limited, Oxford, UK.

Senecoff, J.F., et al.; "DNA Recognition by the FLP Recombinase of the Yeast 2 mu Plasmid, A Mutational Analysis of the FLP Binding Site"; J Mol Biol (1988) 201:405-421; Elsevier Ltd, Amsterdam, The Netherlands.

Kilby, N.J., et al.; "FLP recombinase in transgenic plants: constitutive activity in stably transformed tobacco and generation of marked cell clones in *Arabidopsis*"; The Plant Journal (1995) 8(5):637-652; Blackwell Publishing Ltd, Oxford, UK.

Lloyd, A.M., et al.; "Functional expression of the yeast FLP/FRT site-specific recombination system in *Nicotiana tabacum*"; Mol Gen Genet (1994) 242:653-657; Springer, Berlin/Heidelberg, Germany.

Albert, H., et al.; "Site-specific integration of DNA into wild-type and mutant lox sites place in the plant genome"; The Plant Journal (1995) 7(4):649-659; Blackwell Publishing Ltd, Oxford, UK.

Lyznik, L.A., et al.; "Site-specific recombination for genetic engineering in plants"; Plant Cell Rep (2003) 21:925-932; Springer, Berlin/Heidelberg, Germany.

Sadowski, P.D.; "Site-specific genetic recombination: hops, flips, and flops"; The FASEB Journal (Jun. 1993) 7:760-767; The Federation of American Societies for Experimental Biology, Bethesda, MD US.

Argos, P., et al.; "The integrase family of site-specific recombinases: regional similarities and global diversity"; The EMBO Journal (1986) 5(2):433-440; IRL Press Limited, Oxford, UK.

Lyznik, L.A., et al.; "FLP-mediated recombination of FRT sites in the maize genome"; Nucleic Acids Research (1996) 24(19):3784-3789; Oxford University Press, Oxford, UK.

Esposito, D., et al.; "The integrase family of tyrosine recombinases: evolution of a conserved active site domain"; Nucleic Acids Research (1997) 25(18):3605-3614; Oxford University Press, Oxford, UK.

FRT RECOMBINATION SITES AND METHODS OF USE

CROSS-REFERENCE TO RELATED APPLICATIONS

This application claims the benefit of U.S. Application Ser. No. 60/700,225 filed Jul. 18, 2005, which is herein incorporated by reference in its entirety.

FIELD OF THE INVENTION

The invention relates to site-specific recombination systems and method of use.

BACKGROUND

The random insertion of introduced DNA into the genome of a host cell can be lethal if the foreign DNA happens to insert into, and thereby mutate, a critically important native gene. In addition, even if a random insertion event does not impair the functioning of a gene of a host cell, the expression of an inserted foreign nucleotide sequence may be influenced by position effects caused by the surrounding genomic DNA. In some cases, the nucleotide sequence is inserted into a site where the position effect is strong enough to suppress the function or regulation of the introduced nucleotide sequence. In other instances, overproduction of the gene product has deleterious effects on a cell.

For example, in plants, position effects can result in reduced agronomics, additional costs for further research, creation of additional transgenic events, and slower time to product. For these reasons, efficient methods are needed for targeting the insertion of nucleotide sequences into the genome of various organisms, such as plants, at chromosomal positions that allow desired function of the sequence of interest.

SUMMARY

Methods and compositions using populations of randomized modified FRT recombination sites to identify, isolate and/or characterize modified FRT recombination sites are provided. The recombinogenic modified FRT recombination sites can be employed in a variety of methods for targeted recombination of polynucleotides of interest, including methods to recombine polynucleotides, assess promoter activity, directly select transformed organisms, minimize or eliminate expression resulting from random integration into the genome of an organism, such as a plant, remove polynucleotides of interest, combine multiple transfer cassettes, invert or excise a polynucleotide, and identify and/or characterize transcriptional regulating regions are also provided.

DETAILED DESCRIPTION

Methods and compositions using modified FRT recombination sites include, but are not limited to the following:

1. A method to select a recombinogenic modified FRT recombination site comprising:

a) providing a first population of plasmids wherein each plasmid in said first population comprises a common first selectable marker; and, each plasmid in said first population comprises a member of a population of modified FRT recombination sites;

b) providing a second population of plasmids wherein each plasmid in said second population comprises a common second selectable marker, wherein said first and said second selectable markers are distinct; and, each plasmid in said second population comprises a member of the population of modified FRT recombination sites;

c) combining said first population of plasmids with said second population of plasmids in the presence of a FLP recombinase under conditions where site-specific recombination can occur; and, d) selecting for a co-integrant plasmid comprising the first and the second selectable marker, said co-integrate plasmid comprising the modified FRT recombination site.

2. The method of 1, wherein each member of said population of randomized modified FRT recombination sites comprises a spacer region comprising at least one nucleotide alteration in SEQ ID NO:43.

3. The method of 1, wherein said first and said second population of plasmids are combined in the presence of the FLP recombinase.

4. The method of 1, wherein said co-integrant plasmid comprises a functional modified FRT recombination site.

5. The method of 1 further comprising isolating the co-integrant plasmid.

6. The method of 1, further comprising characterizing the modified FRT recombination site of said co-integrant plasmid.

7. The method of 6, wherein characterizing the modified FRT recombination site comprises determining excision efficiency.

8. The method of 6, wherein characterizing the modified FRT recombination site comprises determining recombination specificity.

9. The method of 6, wherein characterizing the modified FRT recombination sites comprises sequencing the modified FRT recombination site of the co-integrant plasmid.

10. The method of 1, wherein at least one of said first or said second selectable markers is selected from the group consisting of ampicillin and spectinomycin.

11. The method of 1, wherein said first population of plasmids and said second population of plasmids are combined in an equimolar ratio.

12. An isolated library comprising a population of plasmids wherein each plasmid in said population comprises a common selectable marker; and, each plasmid in said population comprises a member of a population of modified FRT recombination sites, wherein said population of plasmids comprises at least about 5 distinct members of the plasmid population.

13. The isolated library of 12, wherein each member of said population of modified FRT recombination sites comprises a spacer region comprising at least one nucleotide alteration in SEQ ID NO:43.

14. The isolated library of 12 or 13, wherein said modified FRT recombination sites of said population are recombinogenic.

15. The isolated library of any one of 12-14, wherein the selectable marker is selected from the group consisting of ampicillin and spectinomycin.

16. The isolated library of any one of 12-15, wherein said population of plasmids comprises at least about 100 distinct members of the plasmid population.

17. The isolated library of any one of 12-15, wherein said population of plasmids comprises at least one modified recombinogenic FRT site comprising a spacer region selected from the group consisting of SEQ ID NOS:1, 2, 3, 5, 6, 7, 8, 9, 10, 11, 12, 13, 14, 15, 16, 17, and 18.

18. The isolated library of 17, wherein said population of plasmids comprises at least one modified recombinogenic FRT site selected from the group consisting of SEQ ID NO:21, 22, 23, 25, 26, 27, 28, 29, 30, 31, 32, 33, 34, 35, 36, 37, or 38.

19. A kit comprising a) a first population of plasmids wherein each plasmid in said first population comprises a first common selectable marker; and, each plasmid in said first population comprises a member of a population of modified FRT recombination sites; and, b) a second population of plasmids wherein each plasmid in said second population comprises a second common selectable marker, wherein said first and said second selectable markers are distinct; and, each plasmid in said second population comprises a member of the population of modified FRT recombination sites.

20. The kit of 19, wherein said kit further comprises a FLP recombinase or a polynucleotide encoding said FLP recombinase.

21. The kit of 20, wherein said kit comprises the polynucleotide encoding a biologically active variant of the FLP recombinase or a biologically active fragment of the FLP recombinase.

22. The kit of any one of 19-21, wherein at least one member of said first population, or said second population of modified FRT recombination sites, or both populations comprises a) a spacer region comprising at least one nucleotide alteration in SEQ ID NO:43; and b) a spacer region selected from the group consisting of SEQ ID NOS:1, 2, 3, 5, 6, 7, 8, 9, 10, 11, 12, 13, 14, 15, 16, 17, 18, or 21, 22, 23, 25, 26, 27, 28, 29, 30, 31, 32, 33, 34, 35, 36, 37, or 38.

23. The kit of any one of 19-22, wherein each member of said first and said second population of modified FRT recombination site is recombinogenic.

24. The kit of any one of 19-22, wherein at least one of said first or said second selectable marker is selected from the group consisting of ampicillin and spectinomycin.

25. A method for generating a library of molecules comprising a) providing a population of modified FRT recombination sites; and, b) contacting said population of modified FRT recombination sites with a population of plasmids having a common selectable marker under conditions for the insertion of said population of modified FRT recombination sites into said population of plasmids, such that each of the plasmids of said population comprises a single member of the population of modified FRT recombination sites, whereby a library of molecules is generated.

26. The method of 25, wherein each member of said population of modified FRT recombination sites comprises a spacer region comprising at least one nucleotide alteration in SEQ ID NO:43.

27. An isolated polynucleotide comprising a nucleotide sequence comprising at least one functional modified FRT recombination site, said functional modified FRT recombination site comprising a spacer sequence selected from the group consisting of SEQ ID NOS:1, 2, 3, 5, 6, 7, 8, 9, 10, 11, 12, 13, 14, 15, 16, 17, and 18.

28. The isolated polynucleotide of 27, wherein said functional modified FRT recombination site comprises SEQ ID NO:21, 22, 23, 25, 26, 27, 28, 29, 30, 31, 32, 33, 34, 35, 36, 37, or 38 or a functional variant thereof, wherein said functional variant is substantially identical to SEQ ID NO:21, 22, 23, 25, 26, 27, 28, 29, 30, 31, 32, 33, 34, 35, 36, 37, or 38.

29. The isolated polynucleotide of 28, wherein said functional modified FRT recombination site comprises SEQ ID NO:21, 22, 23, 25, 26, 27, 28, 29, 30, 31, 32, 33, 34, 35, 36, 37, or 38.

30. The isolated polynucleotide of 27, 28, or 29, wherein said polynucleotide comprises a second recombination site.

31. The isolated polynucleotide of 30, wherein said second recombination site is selected from the group consisting of a FRT site, a mutant FRT site, a LOX site, or a mutant LOX site.

32. The isolated polynucleotide of 31, wherein said second recombination site is selected from the group consisting SEQ ID NO:1, 2, 3, 4, 5, 6, 7, 8, 9, 10, 11, 12, 13, 14, 15, 16, 17, 18, 21, 22, 23, 24, 25, 26, 27, 28, 29, 30, 31, 32, 33, 34, 35, 36, 37, or 38.

33. The isolated polynucleotide of any one of 30-32, wherein said second recombination site is dissimilar and non-recombinogenic with respect to the functional modified FRT recombination site.

34. The isolated polynucleotide of any one of 30-32, wherein said functional modified FRT recombination site and said second recombination site are corresponding recombination sites.

35. A cell comprising the polynucleotide of any one of 27-34.

36. The cell of 35, wherein said cell is from a plant.

37. The cell of 35 or 36, wherein the polynucleotide is stably integrated into the genome of said cell.

38. The cell of 36, wherein said cell is from a monocotyledonous plant.

39. The cell of 38, wherein said monocotyledonous plant cell is from maize, barley, millet, wheat, sorghum, rye, or rice.

40. The cell of 36, wherein said plant cell is from a dicotyledonous plant.

41. The cell of 40, wherein said dicotyledonous plant cell is from soybean, canola, alfalfa, sunflower, safflower, tobacco, *Arabidopsis*, or cotton.

42. A plant comprising the cell of any one of 36-41.

43. A seed having stably integrated into its genome the polynucleotide of any one of 27-34.

44. The cell of any one of 35-42, wherein said cell further has stably incorporated into its genome a polynucleotide encoding a FLP recombinase.

45. The cell of 44, wherein said polynucleotide encodes a biologically active variant of the FLP recombinase.

46. A method for determining the relative recombination excision efficiency of a first and a second FRT recombination site comprising a) providing a polynucleotide comprising the first and the second FRT recombination site, wherein the spacer sequence of said first or said second FRT recombination site is selected from the group consisting of SEQ ID NOS:1, 2, 3, 5, 6, 7, 8, 9, 10, 11, 12, 13, 14, 15, 16, 17, and 18;

b) providing a FLP recombinase under conditions such that said FLP recombinase implements a recombinase-mediated excision event; and, c) determining excision efficiency of said first and said second FRT recombination site relative to a control reaction, wherein the control reaction is done under identical conditions using wild type FRT recombination sites as the first and the second FRT recombination sites.

47. The method of 46, wherein said first and said second FRT recombination sites are corresponding recombination sites.

48. A method to identify dissimilar and non-recombinogenic recombination sites comprising a) providing a first FRT recombination site wherein the spacer sequence is selected from the group consisting of SEQ ID NOS:1, 2, 3, 5, 6, 7, 8, 9, 10, 11, 12, 13, 14, 15, 16, 17, and 18;

b) providing a second dissimilar FRT recombination site;

c) providing a FLP recombinase under conditions such that said FLP recombinase implements a recombination event; and, d) assaying for a recombination event to thereby determine if the first and the second recombination site are non-recombinogenic.

49. The method of any one of 46-48, wherein said first FRT recombination site comprises SEQ ID NO:21, 22, 23, 25, 26, 27, 28, 29, 30, 31, 32, 33, 34, 35, 36, 37, 38 or a functional variant thereof, wherein said functional variant is substantially identical to SEQ ID NO:21, 22, 23, 25, 26, 27, 28, 29, 30, 31, 32, 33, 34, 35, 36, 37, or 38.

50. The method of 49, wherein said first FRT recombination site comprises SEQ ID NO:21, 22, 23, 25, 26, 27, 28, 29, 30, 31, 32, 33, 34, 35, 36, 37, or 38.

51. The method of 46-48, wherein said method occurs in vivo.

52. The method of 51, wherein providing one or more of said first FRT site or said second FRT site comprises transformation.

53. A method for producing site-specific recombination of DNA comprising a) providing a first DNA fragment comprising a first site-specific recombination site, wherein the first site-specific recombination site comprises a polynucleotide is selected from the group consisting of:

i) a FRT recombination site having a spacer region selected from the group consisting of SEQ ID NOS:1, 2, 3, 5, 6, 7, 8, 9, 10, 11, 12, 13, 14, 15, 16, 17, and 18; and ii) a FRT recombination site selected from the group consisting of SEQ ID NOS: 21, 22, 23, 25, 26, 27, 28, 29, 30, 31, 32, 33, 34, 35, 36, 37, and 38;

b) providing a second DNA fragment comprising a second site-specific recombination site which is recombinogenic with the first site-specific recombination site; and, c) providing a site-specific recombinase that catalyzes a site-specific recombination between the first and the second site-specific recombination sites.

54. The method of 53 wherein the first DNA fragment and the second DNA fragment are provided on a single polynucleotide molecule.

55. The method of 53 or 54 wherein the first site-specific recombination site and the second site-specific recombination sites are corresponding sites.

56. The method of 53 or 54 wherein the first site-specific recombination site and the second site-specific recombination sites are dissimilar sites.

57. The method of any one of 53-56 wherein the first site-specific recombination site and the second site-specific recombination site are directly oriented relative to each other.

58. The method of 57 wherein the first and the second site-specific recombination sites flank a first polynucleotide of interest, whereby providing the site-specific recombinase excises the first polynucleotide of interest.

59. The method of 58 wherein excision of the first polynucleotide of interest activates expression of a second polynucleotide of interest.

60. The method of any one of 54-56 wherein the first site-specific recombination site and the second site-specific recombination site are in the opposite orientation relative to each other.

61. The method of 60 wherein the first and the second site-specific recombination sites flank a first polynucleotide of interest, whereby providing the site-specific recombinase inverts the first polynucleotide of interest.

62. The method of 61 wherein inversion of the first polynucleotide of interest activates expression of the first polynucleotide of interest.

63. The method of 61 wherein inversion of the first polynucleotide of interest activates expression of a second polynucleotide of interest.

64. The method of 53 wherein the first DNA fragment is provided on a first polynucleotide and the second DNA fragment is provided on a second separate polynucleotide.

65. The method of 64, wherein the second polynucleotide is a circular molecule.

66. The method of 64 or 65 wherein the second polynucleotide further comprises a polynucleotide of interest.

67. The method of any one of 53-66 wherein the second site-specific recombination site is a modified FRT recombination site comprising a polynucleotide selected from the group consisting of SEQ ID NOS:1, 2, 3, 4, 5, 6, 7, 8, 9, 10, 11, 12, 13, 14, 15, 16, 17, 18, 21, 22, 23, 24, 25, 26, 27, 28, 29, 30, 31, 32, 33, 34, 35, 36, 37, and 38.

68. The method of any one of 53-67 wherein the site-specific recombination occurs in vivo.

69. The method of 68 wherein the site-specific recombination occurs in a eukaryotic cell.

70. The method of 69 wherein the eukaryotic cell is a plant cell.

71. The method of 70 wherein the plant cell is from a plant selected from the group consisting of maize, rice, wheat, barley, millet, sorghum, rye, soybean, alfalfa, canola, *Arabidopsis*, tobacco, sunflower, cotton, and safflower.

72. A method for targeting the insertion of a polynucleotide of interest to a target site comprising a) providing the target site comprising a first functional recombination site comprising a spacer sequence selected from the group consisting of SEQ ID NOS:1, 2, 3, 5, 6, 7, 8, 9, 10, 11, 12, 13, 14, 15, 16, 17, and 18;

b) providing a transfer cassette comprising a second functional recombination site and said polynucleotide of interest, wherein said first and said second recombination sites are recombinogenic with respect to one another; and, c) providing a recombinase wherein said recombinase recognizes and implements recombination at the first and the second recombination sites, and the polynucleotide of interest is inserted at the target site.

73. A method for targeting the insertion of a polynucleotide of interest to a target site, said method comprising:

a) providing the target site comprising a first and a second functional recombination site, wherein said first and said second recombination sites are dissimilar and non-recombinogenic with respect to one another; and at least one of said first or said second recombination sites comprises a spacer sequence selected from the group consisting of SEQ ID NOS: 1, 2, 3, 5, 6, 7, 8, 9, 10, 11, 12, 13, 14, 15, 16, 17, and 18;

b) providing a transfer cassette comprising the polynucleotide of interest, wherein said polynucleotide of interest is flanked by said first and said second recombination sites, and, c) providing a recombinase, wherein said recombinase recognizes and implements recombination at the first and the second recombination sites, and the polynucleotide of interest is inserted at the target site.

74. The method of 73, wherein said target site comprises a second polynucleotide of interest flanked by said first and said second recombination site.

75. A method for assessing promoter activity in a cell comprising:

a) providing the cell having in its genome a target site comprising a first and a second functional recombination site, wherein said first and said second recombination sites are dissimilar and non-recombinogenic, and at least one of said first or said second recombination sites comprises a spacer sequence selected from the group consisting of SEQ ID NOS: 1, 2, 3, 5, 6, 7, 8, 9, 10, 11, 12, 13, 14, 15, 16, 17, and 18; and, b) providing to said cell a transfer cassette comprising a promoter operably linked to a polynucleotide comprising a selectable marker, wherein said transfer cassette is flanked by the first and the second recombination sites, c) providing a recombinase, wherein said recombinase recognizes and implements recombination at the first and the second recombination sites, whereby said transfer cassette is integrated at the target site; and, d) monitoring expression of the selectable marker to assess promoter activity.

76. A method to directly select a transformed cell, said method comprising:

a) providing a population of cells comprising a polynucleotide comprising, in the following order, a promoter operably linked to a target site, wherein the target site comprises a first recombination site and a second recombination site, said first and said second recombination sites are dissimilar and non-recombinogenic with respect to one another, and at least one of said first or said second recombination sites comprises a spacer sequence selected from the group consisting of SEQ ID NOS:1, 2, 3, 5, 6, 7, 8, 9, 10, 11, 12, 13, 14, 15, 16, 17, and 18;

b) introducing into said population of cells a transfer cassette comprising in the following order the first recombination site, a polynucleotide encoding a selectable marker gene not operably linked to a promoter, and the second recombination site;

c) providing a recombinase, wherein said recombinase recognizes and implements recombination at the first and the second recombination sites; and, d) growing said population of cells on an appropriate selective agent to directly select the cell expressing the selectable marker.

77. The method of any one of 72-76, wherein said target site is stably incorporated into the genome of a cell.

78. A method to minimize or eliminate expression resulting from random integration of a nucleic acid molecule of interest into a genome of a cell comprising:

a) providing the cell having stably incorporated into its genome a polynucleotide comprising in the following order: a promoter active in said cell operably linked to an ATG translational start site operably linked to a target site comprising a first and a second functional recombination site, wherein said first and said second recombination sites are dissimilar and non-recombinogenic, and at least one of said first or said second recombination sites comprise a spacer sequence selected from the group consisting of SEQ ID NOS:1, 2, 3, 5, 6, 7, 8, 9, 10, 11, 12, 13, 14, 15, 16, 17, and 18;

b) providing to said cell a transfer cassette comprising in the following order: the first recombination site, the nucleic acid molecule of interest, and the second recombination site, wherein the ATG translational start site of the nucleic acid molecule of interest has been replaced with said first recombination site; and, c) providing a recombinase, wherein said recombinase recognizes and implements recombination at the first and the second recombination sites, whereby the nucleic acid molecule of interest is integrated at the target site and thereby operably linked to the promoter and translational start site of the polynucleotide.

79. A method to excise or invert a polynucleotide of interest in a cell comprising:

a) providing a cell having a transfer cassette comprising the polynucleotide of interest flanked by a first and a second functional recombination site, wherein said first and said second recombination sites are dissimilar and non-recombinogenic and wherein and at least one of said first or said second recombination sites comprise a spacer sequence selected from the group consisting of SEQ ID NOS:1, 2, 3, 5, 6, 7, 8, 9, 10, 11, 12, 13, 14, 15, 16, 17, and 18;

b) providing to said cell an isolated oligonucleotide capable of directing a nucleotide conversion in one of the first or the second recombination sites so as to create two corresponding recombination sites; and, c) providing a recombinase, wherein said recombinase that implements recombination at the corresponding recombination sites, whereby the polynucleotide of interest is excised or inverted.

80. The method of 79, wherein said corresponding recombination sites are directly repeated.

81. The method of 79, wherein said corresponding recombination sites are inverted.

82. The method of 79, wherein said polynucleotide of interest is a promoter or encodes a polypeptide.

83. A method for locating preferred integration sites within the genome of a cell, said method comprising a) introducing into said cell a target site comprising in the following order: a first functional recombination site, a promoter active in said cell operably linked to a polynucleotide, and a second functional recombination site, wherein said first and said second recombination sites are dissimilar and non-recombinogenic and wherein and at least one of said first or said second recombination sites comprise a spacer sequence selected from the group consisting of SEQ ID NOS:1, 2, 3, 5, 6, 7, 8, 9, 10, 11, 12, 13, 14, 15, 16, 17, and 18;

b) determining the level of expression of said polynucleotide; and, c) selecting the cell expressing said polynucleotide.

84. The method of 83, further comprising introducing into the cell a transfer cassette comprising a polynucleotide of interest flanked by said first and said second recombination sites; and, providing a recombinase, wherein said recombinase recognizes and implements recombination at the first and the second recombination sites, whereby the transfer cassette is integrated at the preferred site.

85. The method of any one of 75-84 wherein said cell has stably incorporated into its genome a polynucleotide encoding said recombinase.

86. The method of any one of 73-84 wherein at least one of said dissimilar and non-recombinogenic recombination sites is selected from the group consisting of a FRT site, a functional variant of the FRT site, a LOX site, and a functional variant of the LOX site.

87. The method of 86, wherein one of said dissimilar and non-recombinogenic recombination sites comprises a FRT site or a functional variant of the FRT site.

88. The method of 87, wherein said functional variant of the FRT site is selected from the group consisting of SEQ ID NO:21, 22, 23, 25, 26, 27, 28, 29, 30, 31, 32, 33, 34, 35, 36, 37, 38, 40, 41, or 42.

89. The method of any one of 73-84 wherein said recombinase is a FLP recombinase or a Cre recombinase.

90. The method of 89, wherein the FLP recombinase or the Cre recombinase is encoded by a polynucleotide having maize preferred codons.

91. The method of 89, wherein said recombinase comprises a FLP recombinase or a Cre recombinase.

92. The method of any one of 73, 74, 75, 77 or 78, wherein providing said transfer cassette comprises transformation.

93. The method of any one of 73, 74, 75, 77 or 78, wherein providing said transfer cassette comprises sexual breeding.

94. The method of any one of 72-79 or 84, wherein providing said recombinase comprises transformation.

95. The method of any one of 72-79 or 84, wherein providing said recombinase comprises sexual breeding.

96. The method of any one of 72-78, 83, or 84, wherein at least one of said first or said second recombination sites comprises SEQ ID NO:21, 22, 23, 25, 26, 27, 28, 29, 30, 31, 32, 33, 34, 35, 36, 37, or 38 or a functional variant thereof, wherein said functional variant is substantially identical to SEQ ID NO:21, 22, 23, 25, 26, 27, 28, 29, 30, 31, 32, 33, 34, 35, 36, 37, or 38.

97. The method of 96, wherein at least one of said first or said second recombination site comprises a nucleotide sequence selected from the group consisting of SEQ ID NOS:21, 22, 23, 25, 26, 27, 28, 29, 30, 31, 32, 33, 34, 35, 36, 37, and 38.

98. A method to combine multiple transfer cassettes comprising:

a) providing a target site comprising at least a first and a second functional recombination site;

b) providing a first transfer cassette comprising in the following order at least the first, a third, and the second functional recombination sites, wherein the first and the third recombination sites of the first transfer cassette flank a first polynucleotide of interest, said first, said second, and said third recombination sites are dissimilar and non-recombinogenic with respect to one another, and at least one of said first, said second, or said third recombination sites comprises a spacer sequence selected from the group consisting of SEQ ID NOS: 1, 2, 3, 5, 6, 7, 8, 9, 10, 11, 12, 13, 14, 15, 16, 17, and 18;

c) providing a first recombinase, wherein said first recombinase recognizes and implements recombination at the first and the second recombination sites;

d) providing a second transfer cassette comprising at least the second and the third recombination sites, wherein the second and the third recombination sites of the second transfer cassette flank a second polynucleotide of interest; and, e) providing a second recombinase, wherein said second recombinase recognizes and implements recombination at the second and third recombination sites, whereby the first and the second transfer cassettes are integrated at the target site.

99. A method to combine multiple transfer cassettes comprising:

a) providing a target site comprising in the following order at least a first, a second, and a third functional recombination site; wherein said first, said second, and said third recombination sites are dissimilar and non-recombinogenic with respect to one another, and at least one of said first, said second, or said third recombination sites comprise a spacer sequence selected from the group consisting of SEQ ID NOS: 1, 2, 3, 5, 6, 7, 8, 9, 10, 11, 12, 13, 14, 15, 16, 17, and 18;

b) providing a first transfer cassette comprising a first polynucleotide of interest flanked by the first and the second recombination sites;

c) providing a first recombinase, wherein said first recombinase or variant thereof recognizes and implements recombination at the first and the second recombination sites;

d) providing a second transfer cassette comprising a second polynucleotide of interest flanked by at least the second and the third recombination sites; and, e) providing a second recombinase, wherein said second recombinase recognizes and implements recombination at the second and third recombination sites, whereby the first and the second transfer cassettes are integrated at the target site.

100. The method of 98 or 99, wherein said target site is in a cell.

101. The method of 100, wherein said target site is stably incorporated into the genome of the cell.

102. The method of 98 or 99, wherein at least one of said first, said second, or said first and said second recombinase comprises a FLP recombinase.

103. The method of 102, wherein said first or said second recombinase further comprises a Cre recombinase.

104. The method of 100, wherein at least one polynucleotide encoding at least said first or said second recombinase is stably incorporated into the genome of the cell.

105. The method of 97 or 98, wherein at least one of said dissimilar and non-recombinogenic recombination sites is selected from the group consisting of a FRT site, a biologically active variant of the FRT site, a LOX site, and a biologically active variant of the LOX site.

106. The method of 105, wherein one of said dissimilar and non-recombinogenic recombination sites comprises a FRT site or a biologically active variant of the FRT site.

107. The method of 106, wherein said biologically active variant of the FRT site is FRT 5 (SEQ ID NO:40), FRT 6 (SEQ ID NO:41), FRT 7 (SEQ ID NO:42), or FRT 87 (SEQ ID NO: 24).

108. The method of 102 or 103, wherein the FLP recombinase or the Cre recombinase is encoded by a polynucleotide having maize preferred codons.

109. The method of 102, wherein said first, said second, or said first and said second recombinase comprises a FLP recombinase.

110. The method of 102, wherein said first, said second, or said first and said second recombinase comprises a Cre recombinase.

111. The method 98 or 99, wherein providing at least one of said first or said second recombinase comprises transformation.

112. The method of 98 or 99, wherein providing at least one of said first or said second recombinase comprises sexual breeding.

113. The method 98 or 99, wherein introducing at least one of said first or said second transfer cassette comprises transformation.

114. The method of 98 or 99, wherein introducing at least one of said first or said second transfer cassette comprises sexual breeding.

115. The method of 98 or 99, wherein at least one of said first, said second, or said third recombination sites comprises SEQ ID NO:21, 22, 23, 25, 26, 27, 28, 29, 30, 31, 32, 33, 34, 35, 36, 37, or 38 or a functional variant thereof, wherein said functional variant is substantially identical to SEQ ID NO:21, 22, 23, 25, 26, 27, 28, 29, 30, 31, 32, 33, 34, 35, 36, 37, or 38.

116. The method of 115, wherein at least one of said first, said second, or said third recombination site comprises SEQ ID NO:21, 22, 23, 25, 26, 27, 28, 29, 30, 31, 32, 33, 34, 35, 36, 37, or 38.

117. A method for inverting a polynucleotide of interest comprising a) providing a target site comprising the polynucleotide of interest flanked by a first and a second recombination site, said first and said second recombination sites are recombinogenic with respect to one another and are in an inverted orientation relative to each other; and at least one of said first and said second recombination site comprises a spacer sequence selected from the group consisting of SEQ ID NOS: 1, 2, 3, 5, 6, 7, 8, 9, 10, 11, 12, 13, 14, 15, 16, 17, and 18; and, b) providing a FLP recombinase, wherein said FLP recombinase recognizes and implements recombination at the first and the second recombination sites, thereby inverting the polynucleotide of interest.

118. A method to excise a polynucleotide of interest comprising a) providing a target site comprising a polynucleotide of interest flanked by a first and a second recombination site, said first and said second recombination sites are recombinogenic with respect to one another and are in a directly repeated orientation relative to each other; and at least one of said first and said second recombination site comprises a spacer sequence selected from the group consisting of SEQ ID NOS: 1, 2, 3, 5, 6, 7, 8, 9, 10, 11, 12, 13, 14, 15, 16, 17, and 18;

b) providing a FLP recombinase, wherein said FLP recombinase recognizes and implements recombination at the first and the second recombination sites, thereby excising the polynucleotide of interest.

119. The method of 117 or 118, wherein said target site is in a cell.

120. The method of 119, wherein said target site is stably incorporated into the genome of the cell.

121. The method of any one of 75, 76, 77, 79, 82, 90, 91, 119 or 120, wherein said cell is a plant cell.

122. The method of 119, wherein said method occurs in a cell having stably incorporated into its genome a nucleotide sequence encoding said FLP recombinase.

123. The method of any one of 113, 117, 118, or 122 wherein the FLP recombinase is encoded by a polynucleotide having maize preferred codons.

124. The method of any one of 113, 117 or 118, wherein said recombinase comprises the FLP recombinase.

125. The method of 119, wherein providing said target site comprises transformation.

126. The method of 119, wherein providing said target site comprises sexual breeding.

127. The method 119, wherein providing said FLP recombinase comprises transformation.

128. The method of 119, wherein providing said FLP recombinase comprises sexual breeding.

129. The method of any one of 113, 117 or 118, wherein said first or said second recombination sites comprise SEQ ID NO:21, 22, 23, 25, 26, 27, 28, 29, 30, 31, 32, 33, 34, 35, 36, 37, or 38 or a functional variant thereof, wherein said functional variant is substantially identical to SEQ ID NO:21, 22, 23, 25, 26, 27, 28, 29, 30, 31, 32, 33, 34, 35, 36, 37, or 38.

130. The method of 129, wherein said first or said second recombination sites comprise a nucleotide sequence selected from the group consisting of SEQ ID NOS:21, 22, 23, 25, 26, 27, 28, 29, 30, 31, 32, 33, 34, 35, 36, 37, and 38.

131. The method of 121, wherein said plant cell is a monocotyledonous plant cell.

132. The method of 131, wherein said monocotyledonous cell is from maize, barley, millet, wheat, sorghum, rye, or rice.

133. The method of 121, wherein said plant cell is a dicotyledonous plant cell.

134. The method of 133, wherein said dicotyledonous cell is from soybean, canola, alfalfa, sunflower, safflower, tobacco, *Arabidopsis*, or cotton.

135. The method of any one of 72, 117, or 118, wherein said first and said second recombination sites are corresponding.

136. The method of 72 or 135, wherein said first and said second recombination sites comprise SEQ ID NO:21, 22, 23, 25, 26, 27, 28, 29, 30, 31, 32, 33, 34, 35, 36, 37, or 38 or a functional variant thereof, wherein said functional variant is substantially identical to SEQ ID NO:21, 22, 23, 25, 26, 27, 28, 29, 30, 31, 32, 33, 34, 35, 36, 37, or 38.

137. The method of 136, wherein said first and said second recombination sites comprise a nucleotide sequence selected from the group consisting of SEQ ID NOS:21, 22, 23, 25, 26, 27, 28, 29, 30, 31, 32, 33, 34, 35, 36, 37, and 38.

138. The method of 73, wherein said target site is operably linked to a first and a second convergent promoter; said transfer cassette comprises, in the following order, the first functional recombination site, a polynucleotide of interest orientated in the 5' to 3' direction, a second polynucleotide of interest oriented in the 3' to 5' direction, and the second functional recombination site; wherein insertion of the transfer cassette at the target site results in the first polynucleotide of interest operably linked to the first convergent promoter and the second polynucleotide of interest operably linked to the second convergent promoter.

139. The isolated polynucleotide of 30, wherein said polynucleotide comprises a first convergent promoter, the first recombination site, the second recombination site, and the second convergent promoter.

140. The isolated polynucleotide of 139, wherein said polynucleotide comprises the first convergent promoter, the first recombination site, a first polynucleotide sequence of interest operably linked to said first convergent promoter, a second polynucleotide of interest operably linked to said convergent promoter and the second convergent promoter.

141. A method of excising or inverting a polynucleotide of interest comprising a) providing a polynucleotide comprising, in the following order, a first functional recombination site comprising a spacer sequence selected from the group consisting of SEQ ID NOS:1, 2, 3, 5, 6, 7, 8, 9, 10, 11, 12, 13, 14, 15, 16, 17 and 18, the polynucleotide of interest, and a second functional recombination site, wherein said first and said second recombination sites are recombinogenic with respect to one another; and, b) providing a recombinase or a biologically active variant of said recombinase, wherein said recombinase recognizes and implements recombination at the first and the second recombination sites, wherein the polynucleotide sequence of interest is excised or inverted.

142. The method of 141, wherein said first and said second recombination sites are identical.

143. The method of 141 or 142, wherein said first recombination site, said second recombination site, or both comprise SEQ ID NO:21, 22, 23, 25, 26, 27, 28, 29, 30, 31, 32, 33, 34, 35, 36, 37, or 38 or a functional variant thereof, wherein said functional variant is substantially identical to SEQ ID NO:21, 22, 23, 25, 26, 27, 28, 29, 30, 31, 32, 33, 34, 35, 36, 37, or 38.

144. The method of 143, wherein said first recombination site, said second recombination site, or both comprise a nucleotide sequence selected from the group consisting of SEQ ID NOS:21, 22, 23, 25, 26, 27, 28, 29, 30, 31, 32, 33, 34, 35, 36, 37, and 38.

145. The method of any one of 1-11, 46, 48, 52-82, 84, 85, 89, 94, 95, 98-138, or 141-144, wherein said recombinase is a biologically active variant of the native recombinase.

Various populations of modified FRT recombination sites are provided, including, for example, an isolated library of molecules comprising a population of plasmids where each plasmid in the population comprises a common selectable marker; and, each plasmid in the population comprises a member of a population of modified FRT recombination sites. The population can comprise at least about 5 distinct members of the plasmid population. Other compositions include, an isolated library where the members of the population of modified FRT recombination sites comprise a variant of a spacer region as set forth in SEQ ID NO:43, wherein the variant comprises at least one nucleotide alteration in SEQ ID NO:43. Other compositions include an isolated library where the modified FRT recombination sites comprise a population of functional modified FRT recombination sites.

Compositions further include kits comprising two populations of plasmids. The plasmids in the first population comprise a first common selectable marker; and, each of the plasmids in the first population comprises a member of a population of modified FRT recombination sites. The second population of plasmids comprises a common second and distinct selectable marker; and, each of the plasmids in the second population comprises a member of the population of modified FRT recombination sites. The kit can further comprise a FLP recombinase, a biologically active variant of the FLP recombinase, a polynucleotide encoding a FLP recombinase, or a polynucleotide encoding a biologically active variant of the FLP recombinase.

Methods to select a recombinogenic modified FRT recombination site are also provided. The method comprises providing a first population of plasmids where each of the plasmids in the first population comprises a common first selectable marker; and, each of the plasmids in the first population comprises a member of a population of modified FRT recombination sites. A second population of plasmids is provided where each of the plasmids in the second population comprises a common second distinct selectable marker; and, each of the plasmids in the second population comprises a member of the population of modified FRT recombination sites. The first population of plasmids is combined with the second population of plasmids in the presence of a FLP recombinase or a biologically active variant of the FLP recombinase, under conditions that allow for recombinase-mediated integration. A co-integrant plasmid comprising both the first and the second selectable marker is selected, wherein the co-integrant plasmid comprises at least one modified FRT recombination site.

Methods further comprise isolating the co-integrant plasmid and/or characterizing the modified FRT recombination site of the co-integrant plasmid. Characterizing the modified FRT recombination site can comprise determining recombination excision efficiency and/or determining the sequence of the modified FRT recombination site.

A method for generating a library of molecules is further provided. The method comprises providing a population of modified FRT recombination sites; and, contacting the population of modified FRT recombination sites with a population of plasmids having a common selectable marker under conditions that allow for the insertion of the population of modified FRT recombination sites into the population of plasmids, such that each of the plasmids of the population comprises a member of the population of modified FRT recombination sites.

Additional compositions include an isolated polynucleotide comprising at least one functional modified FRT recombination site, where the functional modified FRT recombination site comprises a spacer sequence selected from the group consisting of SEQ ID NOS:1, 2, 3, 5, 6, 7, 8, 9, 10, 11, 12, 13, 14, 15, 16, 17, and 18. Other compositions include an isolated polynucleotide comprising a nucleotide sequence comprising at least one functional modified FRT recombination site comprising the nucleotide sequence set forth in SEQ ID NOS:21, 22, 23, 25, 26, 27, 28, 29, 30, 31, 32, 33, 34, 35, 36, 37, or 38 or a functional variant thereof, where the variant has substantial sequence identity to SEQ ID NOS:21, 22, 23, 25, 26, 27, 28, 29, 30, 31, 32, 33, 34, 35, 36, 37, or 38.

Organisms, including, for example, prokaryotes, such as bacteria, and eukaryotes, such as yeast, mammals, insects, worms, plants, plant cells, and seed comprising the recited polynucleotides comprising a modified FRT recombination site are also provided. In specific examples, the polynucleotides are stably integrated into the genome of the organism.

Methods are also provided, including methods for producing site-specific recombination of DNA. In some examples the site-specific recombination is an intramolecular reaction, in other examples the site-specific recombination is an intermolecular reaction. The site-specific recombination can be done in vitro or in vivo. The in vivo site-specific recombination reaction can be done in any cell, including prokaryotic or eukaryotic cells. In some examples, the cells are from a plant. Additional methods employ various recombination methods to allow for the targeted insertion, exchange, alteration, expression, excision and/or inversion of any polynucleotide(s) of interest. In one example, a method for targeting the insertion of a polynucleotide of interest to a target site is provided. The method comprises providing the target site, wherein the target site comprises a first and a second functional recombination site, the first and the second functional recombination sites are dissimilar and non-recombinogenic with respect to one another; and at least one of the first or the second recombination sites comprises a modified FRT recombination site disclosed herein. A transfer cassette is provided, wherein the transfer cassette comprises the polynucleotide of interest flanked by the first and the second recombination sites. At least one recombinase is provided. The recombinase recognizes and implements recombination at the first and second recombination sites. The method can occur in vitro or in vivo. In specific examples, the target site is stably incorporated into the genome of an organism.

In another example, a method for targeting the insertion of a polynucleotide of interest is provided. The method comprises providing a target site having at least a first functional recombination site. A transfer cassette is provided comprising a polynucleotide of interest and at least a second functional recombination site, wherein the second functional recombination site is recombinogenic with the first functional recombination site, and the first and/or the second recombination site comprise a modified FRT site disclosed herein. In some examples, the first and the second recombination sites have the same sequence. At least one recombinase is provided. The recombinase recognizes and implements recombination at the first and second recombination sites. The method can occur in vitro or in vivo. In specific examples, the first functional recombination site is stably incorporated into the genome of an organism. In some examples, the polynucleotide of interest and/or the target can later be excised, inverted, or otherwise modified, for example, by the addition of a second polynucleotide of interest at the target site.

In other examples, methods for assessing promoter activity, methods to directly select transformed organisms, methods to minimize or eliminate expression resulting from random integration into the genome of an organism, such as a plant, methods to excise or invert a polynucleotide of interest, methods to combine multiple transfer cassettes, methods for determining the excision efficiency or co-integration efficiency of a set of FRT recombination sites, methods to identify recombinogenic or non-recombinogenic recombination sites, methods for locating preferred integration sites within the genome of an organism, methods to recombine DNA molecules both in vitro and in vivo, methods to reduce non-specific agronomic impact of the insertion of a polynucleotide of interest such as reducing yield drag, and, methods to identify cis regulatory elements in an organism, such as a plant, are also provided.

The minimal wild type FRT recombination site has been characterized and comprises a series of domains including the following nucleotide sequence 5'-AGTTCCTATTCTCTA-GAAAGTATAGGAACT-3' (SEQ ID NO:39). The domains of the minimal FRT recombination site comprises a pair of 11 base pair symmetry elements which are the FLP binding sites (nucleotides 1-11 and 20-30 of SEQ ID NO:39); the 8 base pair core, or spacer, region (nucleotides 12-19 of SEQ ID NO:39); and, the polypyrimidine tracts (nucleotides 3-14 and nucleotides 16-29 of SEQ ID NO:39). A modified FRT recombination site can comprise 1, 2, 3, 4, 5, 6, 7, 8, 9, 10 or more alterations which include substitutions, additions, and/or deletions in one or more of these domains.

Modified FRT recombination sites are provided. A modified FRT recombination site is a nucleotide sequence that is similar but not identical to the minimal native FRT recombination site set forth in SEQ ID NO:39. While the modified FRT recombination site can be functional, a modified FRT recombination site need not retain activity. Unless otherwise noted, a modified FRT recombination site retains the biological activity of the wild type FRT recombination site and comprises a functional recombination site that is recognized by a FLP recombinase and capable of a recombinase-mediate recombination reaction. Thus, a modified FRT recombination site can comprise a deletion, addition, and/or substitution of one or more nucleotides in the 5' or 3' end of the minimal native FRT recombination site, in one or more internal sites in the minimal native FRT recombination site. Generally, modified recombination sites will have at least about 40%, 45%, 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or more sequence identity to the minimal native recombination site over its complete length or to any domain contained therein. For example, a modified FRT recombination site will have the recited % sequence identity to the minimal native FRT nucleotide sequence; to the symmetry elements of the minimal native FRT sequence; to the spacer sequence of the wild type FRT sequence; and/or, to the polypyrimidine tract(s) of the minimal native FRT site as determined by sequence alignment programs and parameters described elsewhere herein. The modified FRT recombination site could therefore include 1, 2, 3, 4, 5, 8, 10, 12, 13, 14, 15, 16, 17, 18, 19, 20, 21, 22, 23, 24, 25, 28, 29 or greater nucleotide substitutions, additions, and/or deletions across the entire length of the minimal recombination site, or alternatively, in each of the various domains of the recombination site as outlined above.

A fragment is a portion of a nucleotide sequence, or of any characterized domain contained therein. For example, a fragment of a modified FRT recombination site could be a portion of the minimal native FRT recombination site, a portion of one or both of the symmetry elements, a portion of the spacer region and/or a portion of the polypyrimidine tract(s) of the native FRT site. While the fragments of a modified recombination site need not have biological activity, in some examples, the fragments of the recombination sites can retain the biological activity of the recombination site, and hence, the fragments can be functional. Unless otherwise noted, a fragment of modified FRT recombination site retains the biological activity of the wild type FRT recombination site. For example, fragments of a modified FRT recombination site may range from at least about 2, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides. Fragments of a modified symmetry element site may range from at least about 2, 3, 4, 5, 6, 7, 8, 9, 10, or 11 nucleotides, fragments of a spacer sequence may range from at least about 1, 2, 3, 5, 6, or 7 of a minimal wild type FRT spacer region, and fragments of a polypyrimidine tract can range from at least 1, 2, 3, 4, 5, 6, 7, 8, 9, 10, 11, 12, 13, or 14 nucleotides.

In other examples, modified FRT recombination sites have mutations such as alterations, additions, deletions in the 8 base pair spacer domain. Non-limiting examples of modified spacer domains are set forth in SEQ ID NO:1, 2, 3, 4, 5, 6, 7, 8, 9, 10, 11, 12, 13, 14, 15, 16, 17 or 18. In specific examples, the modified FRT sites are functional. In other examples, modified FRT recombination sites comprise the spacer regions set forth in SEQ ID NOS:1-18 and further comprise symmetry element FLP binding sites that correspond to those found in the minimal native FRT recombination site. See, SEQ ID NOS:19 and 20 showing wild type symmetry element sequences. Such modified FRT recombination sites are set forth in SEQ ID NOS:21-38. In specific examples, the modified FRT sites are functional. In other examples, modified FRT recombination sites can comprise the spacer sequence set forth in SEQ ID NOS:1-18 and further comprise one or more modifications to the symmetry elements set forth in SEQ ID NOS:19 and 20. In specific examples, the modified FRT sites are functional. Modifications of the symmetry elements (nucleotide sequences at position 1 to 11 and 20 to 30 of SEQ ID NOS:21-38) can include 1, 2, 3, 4, 5, 6, 7, 8, 9, 10 or more substitutions, additions, deletions, or modifications of the nucleotide sequence of the wild type symmetry elements set forth in SEQ ID NOS:19 and 20. In other examples, the modifications of the symmetry elements are substantially identical to SEQ ID NOS:21-28. Substantially identical or substantially similar sequence identity refers to a nucleotide sequence having at least one, two, or three substitutions, deletions, and/or additions as compared to a reference sequence. Thus, a substantially identical variant of a modified FRT recombination site is intended a variant of a functional modified FRT recombination site comprising the nucleotide sequence set forth in SEQ ID NO:21, 22, 23, 24, 25, 26, 27, 28, 29, 30, 31, 32, 33, 43, 35, 36, 37, or 38, wherein the functional variant comprises A) one, two or three alterations, substitutions, additions, and/or deletions between nucleotide positions 1 to 11 of SEQ ID NO:21, 22, 23, 24, 25, 26, 27, 28, 29, 30, 31, 32, 33, 43, 35, 36, 37, or 38; B) one, two or three alterations, substitutions, additions, and/or deletions between nucleotide positions 20 to 30 of SEQ ID NO:21, 22, 23, 24, 25, 26, 27, 28, 29, 30, 31, 32, 33, 43, 35, 36, 37, or 38; and/or C) any combination of A and B. In specific examples, the modified FRT recombination site comprises the spacer sequences of SEQ ID NOS:1-18 and functional variants of the symmetry elements. Functional variants of FRT symmetry elements are known, see, for example, Senecoff et al. (1988) J Mol Biol 201:406-421 and Voziyanov et al. (2002) Nucleic Acid Res 30:7. In certain examples, more than one recombination site may be used in a composition or method.

As discussed above, a modified recombination site can be functional. A functional recombination site is a recombination site that is recombinogenic with a recombination site in the presence of the appropriate recombinase, and unless otherwise noted, a recombination site is functional and includes wild type sites, modified sites, variants, and fragments. Methods to determine if a modified recombination site is recombinogenic are known. As used herein, a functional variant recombination site comprises a functional, modified recombination site.

The recombination sites employed in the methods can be corresponding sites or dissimilar sites. Corresponding recombination sites, or a set of corresponding recombination sites refers to recombination sites have the same nucleotide sequence. In other examples, the recombination sites are dissimilar. Dissimilar recombination sites, or a set of dissimilar recombination sites, are recombination sites that are distinct from each other by having at least one nucleotide difference. The recombination sites within a set of dissimilar recombination sites can be either recombinogenic or non-recombinogenic with respect to one another. Recombinogenic refers to recombination sites capable of recombining with one another. Unless otherwise stated, recombinogenic recombination sites or a set of recombinogenic recombination sites include those sites where the relative excision efficiency of recombination between the sites is greater than 2%, 5%, 10%, 20%, 30%, 40%, 50%, 75%, 100%, or greater. As defined herein, the relative recombination excision efficiency is the excision efficiency in the presence of the native recombinase of a first modified recombination site with a second modified recombination site divided by the excision efficiency of a pair of the appropriate native recombination sites X 100%. For example, when working with modified FRT sites, the relative recombination excision efficiency is defined as the excision efficiency in the presence of native FLP (SEQ ID NO:49) of a first modified FRT site with a second modified FRT site divided by the excision efficiency of a pair of native FRT sites (FRT1, SEQ ID NO:39). Non-recombinogenic refers to recombination sites which in the presence of the appropriate recombinase will not recombine with one another, or recombination between the sites is minimal. Unless otherwise stated, non-recombinogenic recombination sites, or a set of recombinogenic recombination sites include those sites where the relative excision efficiency of recombination between the sites is lower than 2%, 1.5%, 1%, 0.75%, 0.5%, 0.25%, 0.1%, 0.075, 0.005%, 0.001%. Accordingly, any suitable set of non-recombinogenic and/or recombinogenic recombination sites may be utilized, including a FRT site or functional variant thereof, a LOX site or functional variant thereof, any combination thereof, or any other combination of non-recombinogenic and/or recombination sites known.

Methods to identify dissimilar and non-recombinogenic recombination sites are provided. In one method, a first FRT recombination site comprising a spacer sequence selected from the group consisting of SEQ ID NOS:1, 2, 3, 5, 6, 7, 8, 9, 10, 11, 12, 13, 14, 15, 16, 17, and 18 is provided. A second dissimilar FRT recombination site is provided, along with a FLP recombinase under conditions that allow said FLP recombinase to implement a recombination event. Recombination is assayed to determine if the first and the second recombination site are non-recombinogenic with respect to one another. In specific examples, the first and the second recombination sites are provided on the same polynucleotide, while in other examples, the first and the second recombination sites are provided on distinct polynucleotides.

In one example, a method for determining the recombination efficiency, such as relative excision efficiency or the relative co-integration efficiency of a first and a second FRT recombination sites are provided. For example, a method for determining excision efficiency comprises providing a polynucleotide comprising the first and the second FRT recombination site wherein the spacer sequence for at least the first and/or the second FRT site is selected from the group consisting of SEQ ID NOS:1, 2, 3, 4, 5, 6, 7, 8, 9, 10, 11, 12, 13, 14, 15, 16, 17, and 18 or a variant thereof; and, providing a FLP recombinase under conditions that allow the FLP recombinase to implement a recombinase mediated excision event. Recombination excision efficiency is determined. Methods to assay for recombination excision efficiency are known. For example, in Example 3 excision vectors comprising two copies of a modified FRT recombination site in direct orientation are used. In vivo or in vitro assays can be used to determine if the two modified FRT recombination sites are capable of mediating excision in the presence of FLP recombinase.

In another example, a method for determining relative co-integration efficiency is provided. The method comprises providing a first polynucleotide comprising a first FRT recombination site and providing a second polynucleotide comprising a second FRT recombination site, wherein the spacer sequence of either one or both of the first or second recombination site is selected from the group consisting of SEQ ID NOS:1, 2, 3, 4, 5, 6, 7, 8, 9, 10, 11, 12, 13, 14, 15, 16, 17, and 18 or a variant thereof; and, providing a FLP recombinase under conditions that allow the FLP recombinase to implement a recombinase mediated integration event. Relative co-integration efficiency is determined. The relative co-integration efficiency of a set of FRT sites is defined as the co-integration efficiency of the first modified FRT site with a second FRT site compared to the co-integration efficiency of any given FRT site chosen as an appropriate standard such as the wild type minimal FRT1 (SEQ ID NO: 39). A functional modified FRT recombination site can have a co-integration efficiency of about 2%, 10%, 20%, 25%, 30%, 40%, 40%, 50%, 60%, 70%, 80%, 90%, 95%, or 100%, or greater to the relative standard, shown for example in Example 4.

In one example, the first and the second FRT recombination sites have corresponding nucleotide sequences. In yet another example, the first and the second FRT recombination sites are dissimilar. Therefore various sets and combinations of FRT recombination sites can be identified such as sets of functional, dissimilar, non-recombinogenic FRT sites, functional, dissimilar, recombinogenic sites, and/or sets of functional, corresponding, recombinogenic FRT sites.

One or more of the modified FRT recombination sites can be contained in a polynucleotide. In one example, the polynucleotide comprises one or more expression units. An expression unit is a nucleotide sequence comprising a unit of DNA characterized by having a single transcriptional promoter. Alternatively, the polynucleotide containing the modified FRT recombination site need not contain a promoter and/or downstream regulatory sequences. In other examples, the polynucleotide comprising the modified recombination site can be designed such that upon integration into the genome, the sequences contained in the polynucleotide are operably linked to an active promoter. It is recognized that a polynucleotide can have additional elements including, but not limited to, nucleotide sequences of interest, marker genes, recombination sites, termination regions, etc. As illustrated below, the polynucleotide may comprise transfer cassettes, target sites, or any portions thereof.

An isolated or purified polynucleotide or protein, or biologically active portion thereof, is substantially or essentially free from components that normally accompany or interact with the polynucleotide or protein as found in its naturally occurring environment. An isolated or purified polynucleotide or protein is substantially free of other cellular material, or culture medium when produced by recombinant techniques, or substantially free of chemical precursors or other chemicals when chemically synthesized. Typically, an isolated polynucleotide is free of sequences that naturally flank the 5' and/or 3' ends polynucleotide in the genomic DNA of the organism from which the polynucleotide is derived. For example, in various examples, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A protein that is substantially free of cellular material includes preparations of protein having less than about 30%, 20%, 10%, 5%, or 1% dry weight of contaminating protein. When the protein or biologically active portion thereof is recombinantly produced, generally the culture medium represents less than about 30%, 20%, 10%, 5%, or 1% (by dry weight) of chemical precursors or non-protein-of-interest chemicals.

Polynucleotides can comprise ribonucleotides and combinations of ribonucleotides and deoxyribonucleotides. Such deoxyribonucleotides and ribonucleotides include both naturally occurring molecules and synthetic analogues. Polynucleotides also encompass all forms of sequences including, but not limited to, single-stranded forms, double-stranded forms, hairpins, stem-and-loop structures, and the like.

In one example, an isolated polynucleotide is provided, wherein the polynucleotide comprises a modified FRT recombination site. In specific examples, the modified FRT recombination site is the polynucleotide sequence. For example, an isolated polynucleotide can comprise at least one functional modified FRT recombination site, where the functional modified FRT recombination site comprises a spacer sequence selected from the group consisting of SEQ ID NOS: 1, 2, 3, 4, 5, 6, 7, 8, 9, 10, 11, 12, 13, 14, 15, 16, 17, and 18 is provided. In specific examples, the modified FRT recombination site is heterologous to the polynucleotide.

Heterologous refers to a polypeptide or a nucleotide sequence that originates from a different species, or if from the same species, is substantially modified from its native form in composition and/or genomic locus. For example, a heterologous recombination site is a polynucleotide is not found in the native polynucleotide or is not found in the same location in the native polynucleotide, and/or is modified from its native composition.

In other examples, an isolated polynucleotide is provided comprising a nucleotide sequence set forth in SEQ ID NO:21, 22, 23, 24, 25, 26, 27, 28, 29, 30, 31, 32, 33, 34, 35, 36, 37, or 38 or a functional variant thereof. In specific examples, the functional variant comprises at least one, two, three, four, five, six or more alterations between nucleotide positions 1 to 11 and/or between nucleotide positions 20 to 30 of SEQ ID NO:21, 22, 23, 24, 25, 26, 27, 28, 29, 30, 31, 32, 33, 34, 35, 37, or 38. In other examples, the functional variant is substantially identical to the sequence set forth in SEQ ID NO:21, 22, 23, 24, 25, 26, 27, 28, 29, 30, 31, 32, 33, 34, 35, 36, 37, or 38.

A modified FRT recombination site can be introduced into an organism of interest. Introducing comprises presenting to the organism at least one molecule, composition, polynucleotide, or polypeptide, in such a manner that the composition gains access to the interior of a cell. The methods do not depend on a particular method for introducing a polynucleotide or polypeptide to an organism, only that the polynucleotide or polypeptide gains access to the interior of at least one cell of the organism.

Organisms of interest include, but are not limited to both prokaryotic and eukaryotic organisms including, for example, bacteria, yeast, insects, mammals including mice, humans, and plants. In one example, the organism is a plant.

Methods for providing or introducing a composition into various organisms are known and include but are not limited to, stable transformation methods, transient transformation methods, virus-mediated methods, and sexual breeding. Stable transformation indicates that the introduced polynucleotide integrates into the genome of the organism and is capable of being inherited by progeny thereof. Transient transformation indicates that the introduced composition is only temporarily expressed or present in the organism.

Protocols for introducing polynucleotides and polypeptides into plants may vary depending on the type of plant or plant cell targeted for transformation, such as monocot or dicot. Suitable methods of introducing polynucleotides and polypeptides into plant cells and subsequent insertion into the plant genome include microinjection (Crossway et al. (1986) Biotechniques 4:320-334; and U.S. Pat. No. 6,300,543), meristem transformation (U.S. Pat. No. 5,736,369), electroporation (Riggs et al. (1986) Proc Natl Acad Sci USA 83:5602-5606, *Agrobacterium*-mediated transformation (U.S. Pat. Nos. 5,563,055; and 5,981,840), direct gene transfer (Paszkowski et al. (1984) EMBO J 3:2717-2722), and ballistic particle acceleration (U.S. Pat. Nos. 4,945,050; 5,879,918; 5,886,244; 5,932,782; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); McCabe et al. (1988) Biotechnology 6:923-926; Weissinger et al. (1988) Ann Rev Genet 22:421-477; Sanford et al. (1987) Particulate Science and Technology 5:27-37 (onion); Christou et al. (1988) Plant Physiol 87:671-674 (soybean); Finer & McMullen (1991) In Vitro Cell Dev Biol 27P:175-182 (soybean); Singh et al. (1998) Theor Appl Genet 96:319-324 (soybean); Datta et al. (1990) Biotechnology 8:736-740 (rice); Klein et al. (1988) Proc Natl Acad Sci USA 85:4305-4309 (maize); Klein et al. (1988) Biotechnology 6:559-563 (maize); U.S. Pat. Nos. 5,240,855; 5,322,783, and 5,324,646; Klein et al. (1988) Plant Physiol 91:440-444 (maize); Fromm et al. (1990) Biotechnology 8:833-839 (maize); Hooykaas-Van Slogteren et al. (1984) Nature 311: 763-764; U.S. Pat. No. 5,736,369 (cereals); Bytebier et al. (1987) Proc Natl Acad Sci USA 84:5345-5349 (Liliaceae); De Wet et al. (1985) in *The Experimental Manipulation of Ovule Tissues*, ed. Chapman et al. (Longman, N.Y.), pp. 197-209 (pollen); Kaeppler et al. (1990) Plant Cell Rep 9:415-418) and Kaeppler et al. (1992) Theor Appl Genet 84:560-566 (whisker-mediated transformation); D'Halluin et al. (1992) Plant Cell 4:1495-1505 (electroporation); Li et al. (1993) Plant Cell Rep 12:250-255; Christou & Ford (1995) Annals of Botany 75:407-413 (rice); and, Osjoda et al. (1996) Nat Biotechnol 14:745-750 (maize via *Agrobacterium tumefaciens*).

Alternatively, the polynucleotides may be introduced into plants by contacting plants with a virus or viral nucleic acids. Generally, such methods involve incorporating a polynucleotide within a viral DNA or RNA molecule. It is recognized that a polypeptide of interest may be initially synthesized as part of a viral polyprotein, which later may be processed by proteolysis in vivo or in vitro to produce the desired recombinant protein. Further, it is recognized that promoters also encompass promoters utilized for transcription by viral RNA polymerases. Methods for introducing polynucleotides into plants and expressing a protein encoded therein, involving viral DNA or RNA molecules, are known, see, for example, U.S. Pat. Nos. 5,889,191, 5,889,190, 5,866,785, 5,589,367 and 5,316,931.

Transient transformation methods include, but are not limited to, the introduction of polypeptides such as recombinase protein, directly into the organism, the introduction of polynucleotides such as DNA and/or RNA polynucleotides, and the introduction of the RNA transcript, such as an mRNA encoding a recombinase, into the organism. Such methods include, for example, microinjection or particle bombardment. See, for example, Crossway et al. (1986) Mol Gen Genet 202:179-185; Nomura et al. (1986) Plant Sci 44:53-58; Hepler et al. (1994) Proc Natl Acad Sci USA 91:2176-2180; and, Hush et al. (1994) J Cell Sci 107:775-784.

The cells having the introduced sequence may be grown into plants in accordance with conventional ways, see, for example, McCormick et al. (1986) Plant Cell Rep 5:81-84. These plants may then be grown, and either pollinated with the same transformed strain or with a different strain, and the resulting progeny expressing the desired phenotypic characteristic and/or comprising the introduced polynucleotide or polypeptide identified. Two or more generations may be grown to ensure that the polynucleotide is stably maintained and inherited, and seeds harvested. In this manner, transformed seed, also referred to as transgenic seed, having a polynucleotide, for example, comprising a modified FRT site, stably incorporated into their genome are provided.

Examples of plant genuses and species of interest include, but are not limited to, monocots and dicots such as corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats (*Avena*), barley (*Hordeum*), palm, legumes including beans and peas such as guar, locust bean, fenugreek, garden beans, cowpea, mungbean, lima bean, fava bean, lentils, chickpea, and castor, *Arabidopsis*, vegetables, ornamentals, grasses, conifers, crop and grain plants that provide seeds of interest, oil-seed plants, and other leguminous plants. Vegetables include tomatoes (*Lycopersicon esculentum*), lettuce (e.g., *Lactuca sativa*), green beans (*Phaseolus vulgans*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum. Conifers include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*).

The term plant includes plant cells, plant protoplasts, plant cell tissue cultures from which plants can be regenerated, plant calli, plant clumps, and plant cells that are intact in plants or parts of plants such as embryos, pollen, ovules, seeds, flowers, kernels, ears, cobs, husks, stalks, roots, root tips, anthers, and the like.

Prokaryotic cells may also be used in the methods. Prokaryotes include various strains of *E. coli*; however, other microbial strains may also be used, including, for example, *Bacillus* sp, *Salmonella*, and *Agrobacterium*. Exemplary *Agrobacterium* strains include C58c1 (pGUSINT), Agt121 (pBUSINT), EHA101 (pMTCA23GUSINT), EHA105 (pMT1), LBA4404 (pTOK233), GU2260, BU3600, AGL-1, and LBA4402. Such strains are described in detail in Chan et al. (1992) Plant Cell Physiol 33:577; Smith et al. (1995) Crop Sci 35:301; and Hiei et al. (1994) Plant J 6:271-282. Exemplary bacterial strains include, but are not limited to, C600 (ATCC 23724), C600hfl, DH1 (ATCC 33849), DH5α, DH5αF', ER1727, GM31, GM 119 (ATCC 53339), GM2163, HB101 (ATCC 33694), JM83 (ATCC 35607), JM101 (ATCC 33876), JM103 (ATCC 39403), JM105 (ATCC 47016), JM107 (ATCC 47014), JM108, JM109 (ATCC53323), JM110 (ATCC 47013), LE392 (ATCC 33572), K802 (ATCC 33526), NM522 (ATCC 47000), RR1 (ATCC31343), X1997 (ATCC 31244), and Y1088 (ATCC 37195). See also, Jendrisak et al. (1987) *Guide to Molecular Cloning Techniques*, Academic Press, 359-371, Hanahan et al. (1983) J Mol Biol 166:557-580, Schatz et al. (1989) Cell 59:1035, Bullock et al. (1987) BioTechniques 5:376-378, ATCC Bacteria and Bacteriophages (1996) 9th Edition, and Palmer et al. (1994) Gene 143:7-8.

Exemplary, but non-limiting, viral strains include, but are not limited to, geminivirus, begomovirus, curtovirus, mastrevirus, (−) strand RNA viruses, (+) strand RNA viruses, potyvirus, potexvirus, tobamovirus, or other DNA viruses, nanoviruses, viroids, and the like, for example, African cassava mosaic virus (ACMV) (Ward et al. (1988) EMBO J 7:899-904 and Hayes et al. (1988) Nature 334:179-182), barley stripe mosaic virus (BSM) (Joshi et al. (1990) EMBO J 9:2663-2669), cauliflower mosaic virus (CaMV) (Gronenborn et al. (1981) Nature 294:773-776 and Brisson et al. (1984) Nature 310:511-514), maize streak virus (MSV) (Lazarowitz et al. (1989) EMBO J 8:1023-1032 and Shen et al. (1994) J Gen Virol 76:965-969), tobacco mosaic virus (TMV) (Takamatsu et al. (1987) EMBO J 6:307-311 and Dawson et al. (1989) Virology 172:285-292), tomato golden mosaic virus (TGMV) (Elmer et al. (1990) Nucleic Acids Res 18:2001-2006), and wheat dwarf virus (WDV) (Woolston et al. (1989) Nucleic Acids Res 17:6029-6041) and derivatives thereof. See also, Porat et al. (1996) Mol Biotechnol 5:209-221.

Commonly used prokaryotic control sequences include promoters for transcription initiation, optionally with an operator, along with ribosome binding sequences, include such commonly used promoters as the beta lactamase (penicillinase) and lactose (lac) promoter systems (Chang et al. (1977) Nature 198:1056), the tryptophan (trp) promoter system (Goeddel et al. (1980) Nucleic Acids Res 8:4057) and the lambda derived P L promoter and N-gene ribosome binding site (Shimatake et al. (1981) Nature 292:128).

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Prokaryotic/bacterial expression systems for expressing a protein are available using *Bacillus* sp. and *Salmonella* (Palva et al. (1983) Gene 22:229-235; Mosbach et al. (1983) Nature 302:543-545). The Tet operon and the Lac operon can also be employed.

A variety of eukaryotic expression systems such as yeast, insect cell lines, plant and mammalian cells, are known for the expression of a polynucleotide of interest. In some examples, transformed/transfected plant cells are employed as expression systems. Synthesis (introduction/expression) of heterologous nucleotide sequences in yeast is well known (Sherman et al. (1982) *Methods in Yeast Genetics*, Cold Spring Harbor Laboratory). Two widely utilized yeasts for production of eukaryotic proteins are *Saccharomyces cerevisiae* and *Pichia pastoris*. Vectors, strains, and protocols for expression in *Saccharomyces* and *Pichia* are known and available from commercial suppliers (e.g., InVitrogen). Suitable vectors usually have expression control sequences, such as promoters, including 3-phosphoglycerate kinase or alcohol oxidase, and an origin of replication, termination sequences and the like as desired.

Recombinant baculoviruses are generated by inserting the particular sequences-of-interest into the baculovirus genome using established protocols with vectors and reagents from commercial suppliers (e.g., InVitrogen, Life Technologies Incorporated). Commercial vectors are readily available with various promoters, such as polyhedrin and p10, optional signal sequences for protein secretion, or affinity tags, such as 6× histidine. These recombinant viruses are grown, maintained and propagated in commercially available cell lines derived from several insect species including *Spodoptera frugiperda* and *Trichoplusia ni*. The insect cells can be cultured using well-established protocols in a variety of different media, for example, with and without bovine serum supplementation. The cultured cells are infected with the recombinant viruses and the sequence-of-interest is expressed. Proteins expressed with the baculovirus system have been extensively characterized and, in many cases, their post-translational modifications such as phosphorylation, acylation, etc., are identical to the natively expressed protein.

Compositions further comprise populations of modified FRT recombination sites. A population is a group or collection that comprises two or more (i.e., 5, 10, 100, 300, 500, 700, 900, 1100, 1300, 1500, 1700, 1900, 2100, 2300, 2500, 2700, 2900, 3100, 3300, 3500, 3700, 3900, 4000, 4096, $10^4$, $10^5$, $10^6$, $10^7$, $10^8$, $10^9$, or greater) dissimilar modified FRT recombination sites. In specific examples, the modified FRT recombination sites are heterologous to the polynucleotide. Various populations of modified FRT recombination sites are provided, including, for example, a library of randomized modified FRT recombination sites. The library of modified FRT recombination sites can be used via selection techniques for the identification of populations of functional, recombinogenic and/or non-recombinogenic modified FRT recombination sites.

In one example, the population of modified FRT recombination sites comprises a library. A library of modified FRT recombination sites comprises a population of plasmids wherein each of the plasmids in the population comprises a common selectable marker. In addition, each of the plasmids in the population comprises a member of the population of randomized modified FRT recombination sites. Accordingly, each plasmid in the library population has the potential to contain a dissimilar member of the randomized modified FRT recombination site. Populations of many different modified FRT recombination sites can be screened to identify recombinogenic modified FRT recombination sites.

Methods of producing or forming a population of randomized modified FRT recombination sites include identifying the region of the FRT recombination site in which alterations are desired, such as the entire length of the FRT site, the symmetry region, the spacer region, the polypyrimidine tract, or any combination thereof, and, for example, generating a population of oligonucleotides that have the randomly modified nucleotides at the desired region. The randomized sequences in the library of modified FRT recombination sites can be of various lengths and comprise various domains. The chemical or enzymatic reactions by which random sequence segments are made may not yield mathematically random sequences due to unknown biases or nucleotide preferences that may exist. The term randomized, or random, reflects the possibility of such deviations from non-ideality. Accordingly, the term randomized is used to describe a segment of a nucleic acid having, in principle, any possible sequence of nucleotides containing natural or modified bases over a given length. In addition, a bias can be deliberately introduced into the randomized sequence, for example, by altering the molar ratios of precursor nucleoside or deoxynucleoside triphosphates of the synthesis reaction. A deliberate bias may be desired, for example, to approximate the proportions of individual bases in a given organism, or to affect secondary structure. See, Hermes et al. (1998) Gene 84:143-151 and Bartel et al. (1991) Cell 67:529-536. See also, Davis et al. (2002) Proc Natl Acad. Sci. USA 99:11616-11621, which generated a randomized population having a bias comprising a desired structure. Therefore a randomized population of modified FRT recombination sites can be generated to contain a desirable bias in the primary and/or secondary structure of the site, or various domains of the site.

It is not necessary that the library include all possible variant sequences. The library can include as large of a number of possible sequence variants as is practical for selection, to insure that a sufficient number of potential functional modified FRT recombination sites are identified. For example, if the randomized sequence in the modified FRT recombination site includes the 6 internal spacer residues (see, Table 1), it would contain approximately 46 (or 4096) sequence permutations using the 4 naturally occurring bases. However, it is not necessary for the library to include all possible sequences to permit selection of functional modified FRT recombination sites.

Once the members of the population of the randomized modified FRT recombination sites are generated, the sequences are packaged into plasmids using standard methods. In some examples, the population of plasmids can be introduced into suitable cells for both amplification and storage. Although cloning and amplification are typically accomplished using bacterial cells, any functional combination of plasmid and cell may be used. The cloned cells can be frozen for future amplification and use, or the packaged plasmid library can be isolated and itself stored in any form that preserves viability.

Typical plasmids of interest include vectors having defined cloning sites, origins of replication and selectable markers. The plasmid may further include transcription and translation initiation sequences, transcription and translation terminators, and promoters useful for regulation of the expression of the particular nucleic acid. Plasmids can also include generic expression cassettes containing at least one independent terminator sequence, sequences permitting replication of the cassette in eukaryotes, or prokaryotes, or both, such as shuttle vectors, and selection markers for both prokaryotic and eukaryotic systems. Vectors may be suitable for replication and integration in prokaryotes, eukaryotes, or both. For general descriptions of cloning, packaging, and expression systems and methods, see Giliman & Smith (1979) Gene 8:81-97; Roberts et al. (1987) Nature 328:731-734; Berger & Kimmel (1989) *Guide to Molecular Cloning Techniques, Methods in Enzymology*, Vol. 152, Academic Press, Inc., San Diego, Calif., (Berger); Sambrook et al. (1989) *Molecular Cloning—A Laboratory Manual* (2nd ed.) Vols. 1-3, Cold Spring Harbor Laboratory, Cold Spring Harbor Press, N.Y., (Sambrook); and F. M. Ausubel et al. (eds.) (1994) *Current Protocols in Molecular Biology, Current Protocols*, a joint venture between Greene Publishing Associates, Inc. and John Wiley & Sons, Inc. (1994 Supplement) (Ausubel).

In one example, the members of the population of randomized modified FRT recombination sites are introduced into a population of plasmids, wherein each of the plasmids in the population comprises a common selectable marker. In this example, a population of randomized modified FRT recombination sites is contacted with a population of plasmids under conditions that allow for the insertion of the population of randomized modified FRT recombination sites into each plasmid of the population of plasmids such that each of the plasmids of said population comprise a single member of the population of randomized modified FRT recombination sites. In one example, the selectable marker is operably linked to a promoter active in a host cell of interest. Various selectable markers can be used in the method.

A selectable or screenable marker comprises a DNA segment that allows one to identify or select for or against a molecule or a cell that contains it, often under particular conditions. Any selectable marker can be used. These markers can encode an activity, such as, but not limited to, production of RNA, peptide, or protein, or can provide a binding site for RNA, peptides, proteins, inorganic and organic compounds or compositions and the like. Examples of selectable markers include, but are not limited to, DNA segments that comprise restriction enzyme sites; DNA segments that encode products which provide resistance against otherwise toxic compounds including antibiotics, such as, spectinomycin, ampicillin, kanamycin, tetracycline, Basta, neomycin phosphotransferase II (NEO) and hygromycin phosphotransferase (HPT)); DNA segments that encode products which are otherwise lacking in the recipient cell (e.g., tRNA genes, auxotrophic markers); DNA segments that encode products which can be readily identified (e.g., phenotypic markers such as β-galactosidase, GUS; fluorescent proteins such as green fluorescent protein (GFP), cyan (CFP), yellow (YFP), red (RFP), and cell surface proteins); the generation of new primer sites for PCR (e.g., the juxtaposition of two DNA sequence not previously juxtaposed), the inclusion of DNA sequences not acted upon or acted upon by a restriction endonuclease or other DNA modifying enzyme, chemical, etc.; and, the inclusion of a DNA sequences required for a specific modification (e.g., methylation) that allows its identification.

Additional selectable markers include genes that confer resistance to herbicidal compounds, such as glufosinate ammonium, bromoxynil, imidazolinones, and 2,4-dichlorophenoxyacetate (2,4-D). See generally, Yarranton (1992) Curr Opin Biotech 3:506-511; Christopherson et al. (1992) Proc Natl Acad Sci USA 89:6314-6318; Yao et al. (1992) Cell 71:63-72; Reznikoff (1992) Mol Microbiol 6:2419-2422; Barkley et al. (1980) in *The Operon*, pp. 177-220; Hu et al. (1987) Cell 48:555-566; Brown et al. (1987) Cell 49:603-612; Figge et al. (1988) Cell 52:713-722; Deuschle et al. (1989) Proc Natl Acad Sci USA 86:5400-5404; Fuerst et al. (1989) Proc Natl Acad Sci USA 86:2549-2553; Deuschle et al. (1990) Science 248:480-483; Gossen (1993) Ph.D. Thesis, University of Heidelberg; Reines et al. (1993) Proc Natl Acad Sci USA 90:1917-1921; Labow et al. (1990) Mol Cell Biol 10:3343-3356; Zambretti et al. (1992) Proc Natl Acad Sci USA 89:3952-3956; Baim et al. (1991) Proc Natl Acad Sci USA 88:5072-5076; Wyborski et al. (1991) Nucleic Acids Res 19:4647-4653; Hillen & Wissman (1989) Topics Mol Struc Biol 10:143-162; Degenkolb et al. (1991) Antimicrob Agents Chemother 35:1591-1595; Kleinschnidt et al. (1988) Biochemistry 27:1094-1104; Bonin (1993) Ph.D. Thesis, University of Heidelberg; Gossen et al. (1992) Proc Natl Acad Sci USA 89:5547-5551; Oliva et al. (1992) Antimicrob Agents Chemother 36:913-919; Hlavka et al. (1985) *Handbook of Experimental Pharmacology*, Vol. 78 (Springer-Verlag, Berlin); Gill et al. (1988) Nature 334:721-724.

The modified FRT recombination sites, functional modified FRT recombination sites, and the various populations of such molecules including the libraries and plasmid populations can also be used as reagents in kits. For example, kits that can be employed in the various methods disclosed herein are provided. In one example, the kit comprises a first population of plasmids wherein each of the plasmids in the first population comprises a first common selectable marker; and, each of the plasmids in the first population comprises a member of a population of modified FRT recombination sites. The kit can further include a second population of plasmids wherein each of the plasmids in said second population comprises a second common selectable marker, wherein the first and the second selectable markers are distinct; and, each of said plasmids in the second population comprises a member of the population of modified FRT recombination sites. In other examples, the kits can further comprise a FLP recombinase. In still other examples, the kit can comprise a polynucleotide, optionally integrated in the genome of an organism, having at least one target site flanked by functional, dissimilar, non-recombinogenic modified FRT recombination site. Any kit can further be accompanied by instructions for use.

Further provided are kits having a polynucleotide comprising at least one heterologous functional modified FRT recombination site, said functional modified FRT recombination site comprises a spacer sequence selected from the group consisting of SEQ ID NOS:1, 2, 3, 4, 5, 6, 7, 8, 9, 10, 11, 12, 13, 14, 15, 16, 17 and 18. Kits having any of the other polynucleotides disclosed herein are further provided. In specific examples, the polynucleotide in the kit further comprises at least one additional recombination site. In specific examples, the recombination sites are dissimilar and non-recombinogenic with respect to one another, dissimilar and recombinogenic with respect to one another, or corresponding and recombinogenic. Kits can further include one or more of the appropriate recombinases or a polynucleotide encoding the same.

Populations of plasmids comprising a member of a population of modified FRT recombination sites can be generated. Methods to select, identify and/or characterize modified recombinogenic FRT recombination sites from the population of modified FRT recombination sites are provided. In one example selection of a recombinogenic FRT recombination site comprises providing a first population of plasmids wherein each of the plasmids in the first population comprises a common first selectable marker; and, each of the plasmids in the first population comprises a heterologous member of a population of modified FRT recombination sites. A second population of plasmids is provided. The second population of plasmids comprises a second common selectable marker, wherein the first and the second selectable markers are distinct; and, each of the plasmids in the second population comprises a member of the population of modified FRT recombination sites. A distinct selectable marker indicates that the marker present in the first population of plasmids employs a different selection scheme or agent than the selectable marker present in the second population of plasmids. In other words, the presence of a distinct selectable marker in the two populations of plasmids will allow for screening of plasmid populations to determine if none, one, or both of the selectable markers are present.

In one method, the first population of plasmids is combined with the second population of plasmids in the presence of a FLP recombinase. The components are combined in vivo or in vitro under conditions that allow recombinase-mediated integration to occur. Recombinase-mediated integration results in a recombination event between a modified recombinogenic FRT site on one plasmid and a recombinogenic modified FRT site on a second plasmid. The recombination event results in the generation of a co-integrant plasmid. A co-integrant is a nucleic acid molecule that contains both parental molecules, the plasmid of the first library and the plasmid of the second library. It will usually be circular, but may also be linear. A co-integrant can comprise plasmids from the first and second library and therefore have two distinct selectable markers. Additional co-integrant plasmids may form between plasmids of the same population. These co-integrants comprise common selectable markers. Selection schemes that allow for the selection of co-integrants generated via a recombinase-mediated event between plasmids from the first and the second plasmid populations are discussed in detail below.

The conditions in which the two populations of plasmids are combined will allow the FLP recombinase to mediate a recombination event between a modified recombinogenic FRT recombination site contained on a plasmid from the first population with a modified recombinogenic FRT recombination site contained on a plasmid from the second population and thereby form a co-integrant plasmid. Conditions that allow for the recombinase mediated integration event can vary. For instance, the amount of recombinase added to drive the recombinase mediated integration reaction can be determined using known assays, such as titration assays, to determine the appropriate amount of recombinase under given conditions. Similarly, the concentration of both plasmid populations can be varied, along with time, temperature and other reaction conditions to allow for a desired reaction. In one example, the plasmid populations are added in an equimolar ratio.

Any method that allows for the selection, enrichment, or identification of a co-integrant plasmid can be used in the methods. In one example, the co-integrant will comprise two distinct selectable markers. Accordingly, methods for selecting co-integrants away from the plasmids that either failed to undergo a recombinase mediated integration event or undergo an event between plasmids from the same population can entail introducing the mixture comprising the co-integrants and the other unreacted plasmids into a host cell and selecting host cells having both markers.

After the formation of the co-integrant, the selection step can be carried out either in vivo or in vitro depending upon the particular selection scheme being employed, see for example, U.S. Pat. No. 6,277,608. The selection schemes that can be employed in the methods and compositions will vary depending on the selectable marker employed in the plasmid populations.

In vivo selection schemes can be used with a variety of host cells including, for example, E. coli. A non-limiting example of a co-integrant plasmid along with a non-limiting in vivo selection scheme follows. In this example, plasmid A comprises an ampicillin selectable marker and a modified FRT site and plasmid B comprise a spectinomycin selectable marker and a corresponding modified FRT recombination site. Upon addition of FLP recombinase, a recombination event between the modified FRT site of plasmid A and plasmid B occurs. The resulting co-integrant plasmid comprises both the ampicillin marker of the plasmid A and the spectinomycin marker of plasmid B. The plasmids from the reaction mixture are introduced into competent E. coli. E. coli containing co-integrants are resistant to both ampicillin and spectinomycin. Following the selection of co-integrants, the modified FRT recombination sites contained on the co-integrant can be characterized, and the modified FRT recombination sites contained on plasmid A and B can then be determined. For instance, the sites can be sequenced. In addition, the recombination excision efficiency can also be determined. In some examples the modified FRT site of plasmid A and of plasmid B may also be dissimilar and recombinogenic. In such instances, the recombination sites appearing on the co-integrant plasmid may be sequenced to determine the dissimilar/recombinogenic sites appearing on plasmid A and plasmid B.

Other schemes for selection include in vitro assays that assay for the selection of the co-integrants through the generation of new primer sites for PCR; inclusion of DNA sequences acted upon or not acted upon by a restriction endonuclease or other DNA modifying enzyme, chemical, etc.; selection of the desired product by size or other physical property of the molecule; and inclusion of a DNA sequence required for a specific modification (e.g., methylation).

Recombinogenic modified FRT recombination sites can be used in various in vitro and in vivo site-specific recombination methods that allow for the targeted integration, exchange, modification, alteration, excision, inversion, and/or expression of a nucleotide sequence of interest, see for example, WO99/25821, WO99/25854, WO99/25840, WO99/25855, and WO99/25853.

The methods employ a site-specific recombination system. A site-specific recombinase, also referred to as a recombinase, is a polypeptide that catalyzes conservative site-specific recombination between its compatible recombination sites, therefore a recombinase includes native polypeptides as well as variants and/or fragments that retain activity, and native polynucleotides and variants and/or fragments that encode a recombinase that retains activity. The recombinase used in the methods can be a native recombinase or a biologically active fragment or variant of the recombinase. A native polypeptide or polynucleotide comprises a naturally occurring amino acid sequence or nucleotide sequence. For reviews of site-specific recombinases, see Sauer (1994) Curr Op Biotechnol 5:521-527; and Sadowski (1993) *FASEB* 7:760-767. Recombinases useful in the methods and compositions include recombinases from the Integrase and Resolvase families, biologically active variants and fragments thereof, and any other naturally occurring or recombinantly produced enzyme or variant thereof, that catalyzes conservative site-specific recombination between specified DNA recombination sites.

The Integrase family of recombinases has over one hundred members and includes, for example, FLP, Cre, lambda integrase, and R. For other members of the Integrase family, see for example, Esposito et al. (1997) Nucleic Acids Res 25:3605-3614 and Abremski et al. (1992) Protein Eng 5:87-91. Other recombination systems include, for example, the streptomycete bacteriophage phi C31 (Kuhstoss et al. (1991) J Mol Biol 20:897-908); the SSV1 site-specific recombination system from *Sulfolobus shibatae* (Maskhelishvili et al. (1993) Mol Gen Genet 237:334-342); and a retroviral integrase-based integration system (Tanaka et al. (1998) Gene 17:67-76). In other examples, the recombinase is one that does not require cofactors or a supercoiled substrate. Such recombinases include the native Cre (SEQ ID NOS:45 and 46), the native FLP (SEQ ID NOS:48 and 49), or active variants or fragments thereof (SEQ ID NOS:47 and 50).

The FLP recombinase is a protein that catalyzes a site-specific reaction that is involved in amplifying the copy number of the two-micron plasmid of *S. cerevisiae* during DNA replication. FLP recombinase catalyzes site-specific recombination between two FRT sites. The FLP protein has been cloned and expressed (Cox (1993) Proc Natl Acad Sci USA 80:4223-4227). The FLP recombinase for use in the methods and with the compositions may be derived from the genus *Saccharomyces*. One can also synthesize a polynucleotide comprising the recombinase using plant-preferred codons for optimal expression in a plant of interest. A recombinant FLP enzyme encoded by a nucleotide sequence comprising maize preferred codons (FLPm) that catalyzes site-specific recombination events is known (SEQ ID NO:50, and U.S. Pat. No. 5,929,301). Additional functional variants and fragments of FLP are known (Buchholz et al. (1998) Nat Biotechnol 16:617-618, Hartung et al. (1998) J Biol Chem 273:22884-22891, Saxena et al. (1997) Biochim Biophys Acta 1340:187-204, and Hartley et al. (1980) Nature 286:860-864).

The bacteriophage recombinase Cre catalyzes site-specific recombination between two lox sites. The Cre recombinase is known (Guo et al. (1997) Nature 389:40-46; Abremski et al. (1984) J Biol Chem 259:1509-1514; Chen et al. (1996) Somat Cell Mol Genet 22:477-488; Shaikh et al. (1977) J Biol Chem 272:5695-5702; and, Buchholz et al. (1998) Nat Biotechnol 16:617-618. Cre polynucleotide sequences may also be synthesized using plant-preferred codons, for example such sequences (moCre) are described in WO 99/25840 and set forth in SEQ ID NO:47.

It is further recognized that a chimeric recombinase can be used in the methods. A chimeric recombinase is a recombinant fusion protein which is capable of catalyzing site-specific recombination between recombination sites that originate from different recombination systems. For example if a set of functional recombination sites, characterized as being dissimilar and non-recombinogenic with respect to one another, is utilized in the methods and compositions, and the set comprises a FRT site and a LoxP site, a chimeric FLP/Cre recombinase or active variant or fragment thereof will be needed or both recombinases may be separately provided.

Methods for the production and use of such chimeric recombinases or active variants or fragments thereof are described in WO 99/25840.

Fragments and variants of the polynucleotides encoding recombinases and fragments and variants of the recombinase proteins are also encompassed. A fragment is a portion of the polynucleotide and/or any protein encoded thereby or a portion of the polypeptide. Fragments of a polynucleotide may encode protein fragments that retain the biological activity of the native protein and hence implement a recombination event. Thus, fragments of a polynucleotide may range from at least about 20 nucleotides, about 50 nucleotides, about 100 nucleotides, and up to the full-length polynucleotide encoding a recombinase.

A fragment of a polynucleotide that encodes a biologically active portion of a recombinase protein will encode at least 15, 25, 30, 50, 100, 150, 200, 250, 300, 320, 350, 375, 400, or 420 contiguous amino acids, or up to the total number of amino acids present in a full-length recombinase protein (i.e., 423 amino acids for the FLP recombinase and 338 amino acids for the Cre recombinase) used in the methods.

A biologically active portion of a recombinase protein can be prepared by isolating a portion of one of the polynucleotides encoding the portion of the recombinase polypeptide and expressing the encoded portion of the recombinase protein, and assessing the activity of the portion of the recombinase. Polynucleotides that encode fragments of a recombinase polypeptide can comprise nucleotide sequence comprising at least 16, 20, 50, 75, 100, 150, 200, 250, 300, 350, 400, 450, 500, 550, 600, 650, 700, 800, 900, 1,000, 1,100, or 1,200 nucleotides, or up to the number of nucleotides present in a full-length recombinase nucleotide sequence (i.e., 1032 nucleotides for the FLP recombinase and 1260 nucleotides for the Cre recombinase) disclosed herein.

Variant sequences have a high degree of sequence similarity. For polynucleotides, conservative variants include those sequences that, because of the degeneracy of the genetic code, encode the amino acid sequence of one of the native recombinase polypeptides. Variants such as these can be identified with the use of well-known molecular biology techniques, as, for example, with polymerase chain reaction (PCR) and hybridization techniques. Variant polynucleotides also include synthetically derived nucleotide sequences, such as those generated, for example, by using site-directed mutagenesis but which still encode a recombinase protein. Generally, variants of a particular polynucleotide will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by known sequence alignment programs and parameters.

Variants of a particular polynucleotide (the reference nucleotide sequence) can also be evaluated by comparison of the percent sequence identity between the polypeptide encoded by a variant polynucleotide and the polypeptide encoded by the reference polynucleotide. Thus, for example, isolated polynucleotides that encode a polypeptide with a given percent sequence identity to the recombinase are known. Percent sequence identity between any two polypeptides can be calculated using sequence alignment programs and parameters described. Where any given pair of polynucleotides is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

A variant protein is intended a protein derived from the native protein by deletion, addition, and/or substitution of one or more amino acids to the N-terminal, internal region(s), and/or C-terminal end of the native protein. Variant proteins are biologically active, that is they continue to possess the desired biological activity of the native protein, for example a variant recombinase will implement a recombination event between appropriate recombination sites. Such variants may result from, for example, genetic polymorphism or from human manipulation. Biologically active variants of a native recombinase protein will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to the amino acid sequence for the native protein as determined by known sequence alignment programs and parameters. A biologically active variant of a protein may differ from that protein by as few as 1-15 amino acid residues, as few as 1-10, such as 6-10, as few as 5, as few as 4, 3, 2, or even 1 amino acid residue.

Sequence relationships can be analyzed and described using computer-implemented algorithms. The sequence relationship between two or more polynucleotides, or two or more polypeptides can be determined by generating the best alignment of the sequences, and scoring the matches and the gaps in the alignment, which yields the percent sequence identity, and the percent sequence similarity. Polynucleotide relationships can also be described based on a comparison of the polypeptides each encodes. Many programs and algorithms for the comparison and analysis of sequences are available.

Unless otherwise stated, sequence identity/similarity values provided herein refer to the value obtained using GAP Version 10 (GCG, Accelrys, San Diego, Calif.) using the following parameters: % identity and % similarity for a nucleotide sequence using a gap creation penalty weight of 50 and a gap length extension penalty weight of 3, and the nwsgapdna.cmp scoring matrix; % identity and % similarity for an amino acid sequence using a GAP creation penalty weight of 8 and a gap length extension penalty of 2, and the BLOSUM62 scoring matrix (Henikoff & Henikoff (1989) Proc Natl Acad Sci USA 89:10915).

GAP uses the algorithm of Needleman & Wunsch (1970) J Mol Biol 48:443-453, to find an alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. GAP presents one member of the family of best alignments.

Sequence identity, or identity, is a measure of the residues in the two sequences that are the same when aligned for maximum correspondence. Sequences, particularly polypeptides, that differ by conservative substitutions are said to have sequence similarity or similarity. Means for making this adjustment are known, and typically involve scoring a conservative substitution as a partial rather than a full mismatch. For example, where an identical amino acid is given a score of 1 and a non-conservative substitution is given a score of zero, a conservative substitution is given a score between zero and 1. The scoring of conservative substitutions is calculated using the selected scoring matrix (BLOSUM62 by default for GAP).

Proteins may be altered in various ways including amino acid substitutions, deletions, truncations, and insertions. Methods for such manipulations are generally known. For example, amino acid sequence variants of the recombinase proteins can be prepared by mutations in the DNA. Methods for mutagenesis and nucleotide sequence alterations include for example, Kunkel (1985) Proc Natl Acad Sci USA 82:488-492; Kunkel et al. (1987) Methods in Enzymol 154:367-382; U.S. Pat. No. 4,873,192; Walker & Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl Biomed Res Found, Washington, D.C.). Conservative substitutions, such as exchanging one amino acid with another having similar properties, may be preferable.

The recombinase polynucleotides used include both the naturally occurring native sequences as well as mutant or modified forms. Likewise, the proteins used in the methods encompass both naturally occurring proteins as well as variations and modified forms thereof. Such variants continue to possess the ability to implement a recombination event. Generally, the mutations made in the polynucleotide encoding the variant polypeptide do not place the sequence out of reading frame or create complementary regions that could produce secondary mRNA structure. See, EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, the effect will be evaluated by routine screening assays. Assays for recombinase activity are known and generally measure the overall activity of the enzyme on DNA substrates containing recombination sites. For example, to assay for FLP activity, inversion of a DNA sequence in a circular plasmid containing two inverted FRT sites can be detected as a change in position of restriction enzyme sites. This assay is described in Vetter et al. (1983) PNAS 80:7284. Alternatively, excision of DNA from a molecule or intermolecular recombination frequency induced by the enzyme may be assayed, as described, for example, in Babineau et al. (1985) J Biol Chem 260:12313; Meyer-Leon et al. (1987) Nucleic Acid Res 15:6469; and Gronostajski et al. (1985) J Biol Chem 260:12328. Alternatively, recombinase activity may also be assayed by excision of a sequence flanked by recombinogenic FRT sites that upon removal will activate an assayable marker gene. Similar assay strategies may be used for Cre or other recombinase enzymes.

Variant polynucleotides and proteins also encompass sequences and proteins derived from a mutagenic and/or recombinogenic procedure such as DNA shuffling. With such a procedure, one or more different recombinase coding sequences can be manipulated to create a new recombinase protein possessing the desired properties. In this manner, libraries of recombinant polynucleotides are generated from a population of related polynucleotides comprising sequence regions that have substantial sequence identity and can be homologously recombined in vitro or in vivo. Strategies for such DNA shuffling are known and include for example, Stemmer (1994) Proc Natl Acad Sci USA 91:10747-10751; Stemmer (1994) Nature 370:389-391; Crameri et al. (1997) Nat Biotech 15:436-438; Moore et al. (1997) J Mol Biol 272:336-347; Zhang et al. (1997) Proc Natl Acad Sci USA 94:4504-4509; Crameri et al. (1998) Nature 391:288-291; and U.S. Pat. Nos. 5,605,793 and 5,837,458.

The methods and compositions can further employ recombination sites other than the modified FRT sites provided herein. A recombination site is any native or synthetic/artificial polynucleotide that is recognized by the recombinase enzyme of interest. Many recombination systems are known as is the appropriate recombination site(s) to be used with the recombination system of interest, including biologically active variants and fragments of recombination sites. Examples of recombination sites for use are known and include FRT sites including the native FRT site (FRT1, SEQ ID NO:39), and various functional variants of FRT, including but not limited to, FRT5 (SEQ ID NO:40), FRT6 (SEQ ID NO:41), FRT7 (SEQ ID NO:42), FRT87 (SEQ ID NO:24), and the other functional modified FRT sites disclosed herein. See, for example, WO 03/054189, WO 02/00900, WO 01/23545, and, Schlake et al. (1994) Biochemistry 33:12745-12751.

Recombination sites from the Cre/Lox site-specific recombination system can also be used. Such recombination sites include, for example, native LOX sites and various functional variants of LOX. An analysis of the recombination activity of variant LOX sites is presented in Lee et al. (1998) Gene 216:55-65 and in U.S. Pat. No. 6,465,254. Also, see for example, Schlake & Bode (1994) Biochemistry 33:12746-12751; Huang et al. (1991) Nucleic Acids Res 19:443-448; Sadowski (1995) In *Progress in Nucleic Acid Research and Molecular Biology* Vol. 51, pp. 53-91; U.S. Pat. No. 6,465,254; Cox (1989) In *Mobile DNA*, Berg and Howe (eds) American Society of Microbiology, Washington D.C., pp. 116-670; Dixon et al. (1995) Mol Microbiol 18:449-458; Umlauf & Cox (1988) EMBO J 7:1845-1852; Buchholz et al. (1996) Nucleic Acids Res 24:3118-3119; Kilby et al. (1993) Trends Genet 9:413-421; Rossant & Geagy (1995) Nat Med 1:592-594; Albert et al. (1995) Plant J 7:649-659; Bayley et al. (1992) Plant Mol Biol 18:353-361; Odell et al. (1990) Mol Gen Genet 223:369-378; Dale & Ow (1991) Proc Natl Acad Sci USA 88:10558-10562; Qui et al. (1994) Proc Natl Acad Sci USA 91:1706-1710; Stuurman et al. (1996) Plant Mol Biol 32:901-913; Dale et al. (1990) Gene 91:79-85; and WO 01/111058.

Any suitable recombination site or set of recombination sites may be utilized in the methods and compositions, including a FRT site, a functional variant of a FRT site, a LOX site, and functional variant of a LOX site, any combination thereof, or any other combination of recombination sites known.

Directly repeated indicates that the recombination sites in a set of recombinogenic recombination sites are arranged in the same orientation, such that recombination between these sites results in excision, rather than inversion, of the intervening DNA sequence. Inverted recombination site(s) indicates that the recombination sites in a set of recombinogenic recombination sites are arranged in the opposite orientation, so that recombination between these sites results in inversion, rather than excision, of the intervening DNA sequence.

The target site and transfer cassette comprise at least one recombination site. The site-specific recombinase(s) used will depend upon the recombination sites present in the target site and the transfer cassette, for example if FRT sites are utilized, a FLP recombinase or active variant thereof will be provided. In the same manner, where Lox sites are utilized, a Cre recombinase or active variant thereof is provided. If the set of functional recombination sites comprises both a FRT site and a Lox site, either a chimeric FLP/Cre recombinase or an active variant or both FLP and Cre recombinases or active variants thereof will be provided. In one example, at least one of the recombination sites employed at the target site, transfer cassette, or both will comprise at least one functional modified FRT recombination site disclosed herein.

Providing includes any method that allows for a polypeptide and/or a polynucleotide such as a recombinase, target site, transfer cassette, polynucleotide of interest to be brought together with the recited components. For instance, a cell can be provided with these various components via a variety of methods including transient and stable transformation methods; co-introducing a recombinase DNA, mRNA or protein directly into the cell; employing an organism, cell, strain or line that expresses the recombinase for the initial transformation; or growing/culturing the organism carrying the target site and crossing it to an organism that expresses an active recombinase protein and selecting events in the progeny. Any promoter including constitutive, inducible, developmentally/temporal, or spatially regulated promoter capable of regulating expression in the organism of interest may be used to express the appropriate recombinase.

Compositions comprising recombinogenic modified FRT recombination sites are provided, along with biologically active variants and fragments of the recombinogenic modified FRT recombinant sites. The recombinogenic modified FRT recombination site can be used in various site-specific recombination methods.

The methods can employ target sites and transfer cassettes to allow for the manipulation, exchange, excision, alteration, inversion and/or introduction of a nucleotide sequence in vivo or in vitro. A target site comprises at least one recombination site. In specific examples, the target site comprises a polynucleotide that is immediately flanked by at least two recombination sites, including sets of functional recombination sites that are dissimilar and non-recombinogenic with respect to one another; corresponding and recombinogenic with respect to one another; or dissimilar and recombinogenic with respect to one another. One or more intervening sequences may be present between the recombination sites of the target site. Intervening sequences of particular interest include linkers, adapters, regulatory regions, introns, restriction sites, enhancers, insulators, selectable markers, nucleotide sequences of interest, promoters, and/or other sites that aid in vector construction or analysis. It is further recognized that a recombination site can be contained within the nucleotide sequence of interest including introns, coding sequence, 5' UTRs, 3' UTRs, and/or regulatory regions.

In specific examples, the target site is in a cell or an organism of interest. In other examples, the target site is stably integrated into the genome of the cell or the organism of interest. It is recognized that the cell or the organism may comprise multiple target sites, which may be located at one or multiple loci within or across chromosomes. Multiple independent manipulations of each target site in the organism are available. Additionally, the target site may also comprise an expression cassette comprising a nucleotide sequence encoding an appropriate recombinase. In another example, the nucleotide sequence encoding the recombinase is stably integrated in the genome of the organism.

The methods further employ transfer cassettes. A transfer cassette comprises at least one recombination site. In specific examples, the transfer cassette comprising a polynucleotide flanked by at least a first recombination site and a second recombination site, wherein the first and second recombination sites correspond to the recombination sites in the target site. The first and the second functional recombination sites of the transfer cassette can be dissimilar and non-recombinogenic with respect to one another. When a target site and a transfer cassette comprising compatible recombination sites and the recombinase are combined the nucleotide sequence between the recombination sites of the target site will be exchanged with the nucleotide sequence between the recombination sites of the transfer cassette. Flanked by, when used in reference to the position of the recombination sites of the target site or the transfer cassette, refers to a position immediately adjacent to the sequence intended to be exchanged or inserted.

The transfer cassette can further comprise a polynucleotide of interest. The recombination sites may be directly contiguous with the polynucleotide of interest or there may be one or more intervening sequences present between one or both ends of the polynucleotide of interest and the recombination sites. Intervening sequences of particular interest include linkers, adapters, enhancers, introns, insulators, restriction sites, selectable markers, polynucleotides of interest, promoters, and/or other sites that aid in vector construction or analysis. The recombination sites can be contained within the polynucleotide of interest including within introns, coding sequence, and/or 5' and 3' untranslated regions.

In one example, the transfer cassette and/or the target site comprise at least one functional modified FRT recombination site, where the functional modified FRT recombination site comprises a spacer sequence selected from the group consisting of SEQ ID NOS:1, 2, 3, 4, 5, 6, 7, 8, 9, 10, 11, 12, 13, 14, 15, 16, 17, and 18. In other examples, the transfer cassette and/or target site comprises at least one functional modified FRT recombination site comprising SEQ ID NO:21, 22, 23, 24, 25, 26, 27, 28, 29, 30, 31, 32, 33, 34, 35, 36, 37, or 38 or a functional variant thereof. The functional variant can comprise one, two, three, four, five, six, or more alterations between nucleotide positions 1 to 11 and/or between nucleotide positions 20 to 30 of SEQ ID NO:21, 22, 23, 24, 25, 26, 27, 28, 29, 30, 31, 32, 33, 34, 35, 36, 37, or 38. In still other examples, the functional variant is substantially identical to the sequence of SEQ ID NOS:21-38.

Any means can be used to bring together the various components of the recombination system. For example, in in vitro systems, the recombinase and the polynucleotide(s) comprising the recombination sites can be provided by contacting the components under the appropriate conditions to allow for a recombination event. Alternatively a variety of methods are known for the introduction of nucleotide sequences and polypeptides into an organism, including, for example, transformation, sexual crossing, and the introduction of the polypeptide, DNA, or mRNA into the cell. See, also, WO99/25884.

The methods find use in various applications. For example, the methods can employ the use of two modified functional FRT recombination sites and allow for in vivo and in vitro exchange, insertion, inversion, or excision of a nucleotide sequence of interest. For example, the cell or the organism of interest can comprise a first polynucleotide comprising a target site comprising a first functional modified FRT recombination site. The cell or the organism is provided a second polynucleotide comprising a transfer cassette comprising either a second corresponding and functional FRT recombination site or a second dissimilar FRT site that is recombinogenic with respect to the first site. A FLP recombinase is provided under conditions that allow for a recombination event. The recombination event between the two recombinogenic recombination sites results in the insertion of the transfer cassette along with the entire second polynucleotide it is contained on into the first polynucleotide. In some examples, the first polynucleotide is stably integrated into the genome of the organism. The method can also be employed in an in vitro context. For example, the first and the second polynucleotides can comprise polynucleotides such as plasmids combined in vitro in the presence of an appropriate recombinase. In this example, a recombination event will produce a co-integrant plasmid. Such methods find use, for example, in various cloning technologies, including PCR-amplification of fragments (Sadowski et al. (2003) BMC Biotechnol 18:9), cloning vectors (Snaith et al. (1995) Gene 166:173-174 and U.S. Pat. Nos. 6,140,129, 6,410,317, 6,355,412, 5,888,732, 6,143,557, 6,171,861, 6,270,969, and 6,277,608) and viral vectors (U.S. Pat. No. 6,541,245).

In other examples, the method comprises providing a target site having a first and a second functional recombination site, wherein the first and the second recombination sites are dissimilar and non-recombinogenic with respect to one another and at least one of the first or the second recombination sites comprise a functional modified FRt recombination site disclosed herein; providing a transfer cassette comprising a polynucleotide of interest flanked by the first and the second recombination site; and, providing a recombinase. The recombinase recognizes and implements recombination at the first and the second recombination sites.

In specific examples, the target site is in a cell or host organism; and, in other examples, the target site is stably integrated into the genome of the cell or the host organism. In still other examples, the target site comprises a polynucleotide of interest. In this example, if the target site and transfer cassette comprise the first and the second recombination sites which are dissimilar and non-recombinogenic with respect to one another the sequence of interest in the target site is exchanged for a second polynucleotide of interest contained in the transfer cassette.

In other examples, the compositions provided herein are used in methods to reduce the complexity of integration of transgenes in the genome of a cell or an organism, such as a plant cell or a plant. In this method, organisms having simple integration patterns in their genomes are selected. A simple integration pattern indicates that the transfer cassette integrates predominantly only at the target site, and at less than about 25, 20, 15, 10, 9, 8, 7, 6, 5, 4, 3, 2, or 1 random position(s) other than the target site in the genome. Methods for determining the integration patterns are known in the art and include, for example, Southern blot analysis and RFLP analysis.

A method to directly select a transformed cell or an organism, such as a plant or plant cell is provided. The method comprises providing a population of cells or organisms having a polynucleotide comprising a target site. The polynucleotide comprises, in the following order, a promoter and a target site comprising a first and a second functional recombination site, wherein the first and the second recombination sites are dissimilar and non-recombinogenic with respect to one another and at least one of the first or the second recombination sites comprise a functional modified FRT recombination site provided herein. A transfer cassette is introduced into the population of cells or organisms, where the transfer cassette comprises, in the following order, the first recombination site, a polynucleotide comprising a selectable marker not operably linked to a promoter, and the second recombination site. A recombinase or a biologically active fragment is provided that recognizes and implements recombination at the first and second recombination sites, and thereby operably linking the selectable marker to the promoter. The population of cells or organisms is then grown on the appropriate selective agent to recover the organism that has successfully undergone targeted integration of the transfer cassette at the target site. In other examples, the population of cells or organisms has stably incorporated into their genomes the target site.

The activity of various promoters at a characterized location in the genome of a cell or an organism can be determined. Thus, the desired activity and/or expression level of a nucleotide sequence of interest can be achieved, as well as, the characterization of promoters for expression in the cell or the organism of interest. In one example, the method for assessing promoter activity in a cell or an organism comprises providing a cell or an organism comprising in its genome a polynucleotide comprising a target site having a first and a second functional recombination site, wherein the first and the second recombination sites are dissimilar and non-recombinogenic with respect to one another, wherein at least one of the first or the second functional recombination sites comprises a functional modified FRT recombination site provided herein. A transfer cassette is introduced into the cell or the organism, where the transfer cassette comprises a promoter operably linked to a polynucleotide comprising a selectable marker and the transfer cassette is flanked by the first and the second functional recombination sites. A recombinase is provided, wherein said recombinase recognizes and implements recombination at the first and second recombination sites. Promoter activity is assessed by monitoring expression of the selectable marker. In this manner, different promoters can be integrated at the same position in the genome and their activity compared.

In some examples, the transfer cassette comprises in the following order: the first recombination site, a promoter operably linked to a third recombination site operably linked to a polynucleotide comprising a selectable marker, and the second recombination site, where the first, the second, and the third functional recombination sites are dissimilar and non-recombinogenic with respect to one another. This transfer cassette can be generically represented as RSa-P1::RSc::S1-RSb. Following the introduction of the transfer cassette at the target site, the activity of the promoter (P1) can be analyzed using methods known in the art. Once the activity of the promoter is characterized, additional transfer cassettes comprising a polynucleotide of interest flanked by the second and the third recombination site can be introduced into the organism. Upon recombination, the expression of the polynucleotide of interest will be regulated by the characterized promoter. Accordingly, organisms, such as plant lines, having promoters that achieve the desired expression levels in the desired tissues can be engineered so that nucleotide sequences of interest can be readily inserted downstream of the promoter and operably linked to the promoter and thereby expressed in a predictable manner.

In some examples multiple promoters can be employed to regulate transcription at a single target site. In this method, the target site comprising the first and the second recombination sites is flanked by two convergent promoters. Convergent promoters refers to promoters that are oriented on either terminus of the target site. The same promoter, or different promoters may be used at the target site. Each of the convergent promoters is operably linked to either the first or the second recombination site. For example, the target site flanked by the convergent promoters can comprise P1→:R1-R2:←P2, where P is a promoter, the arrow indicates the direction of transcription, R is a recombination site, and the colon indicates the components are operably linked.

The transfer cassette employed with the target site having the convergent promoters can comprise, in the following order, the first recombination site, a first polynucleotide of interest orientated in the 5' to 3' direction, a second polynucleotide of interest orientated in the 3' to 5' direction, and a second recombination site. The insertion of the transfer cassette at the target site results in the first polynucleotide of interest operably linked to the first convergent promoter, and the second polynucleotide of interest operably linked to the second convergent promoter. The expression of the first and/or the second polynucleotide of interest may be increased or decreased in the cell or organism. The expression of the first and/or the second polynucleotide of interest may also be independently regulated depending upon which promoters are used. It is recognized that target sites can be flanked by other elements that influence transcription. For example, insulator elements can flank the target site to minimize position effects. See, for example, U.S. Publication No. 2005/0144665.

Any promoter can be used, and is typically selected based on the desired outcome. A promoter is a region of DNA involved in recognition and binding of RNA polymerase and other proteins to initiate transcription. A plant promoter is a promoter capable of initiating transcription in a plant cell, for a review of plant promoters see Potenza et al. (2004) In Vitro Cell Dev Biol 40:1-22.

Constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) Nature 313:810-812); rice actin (McElroy et al. (1990) Plant Cell 2:163-171); ubiquitin (Christensen et al. (1989) Plant Mol Biol 12:619-632 and Christensen et al. (1992) Plant Mol Biol 18:675-689); pEMU (Last et al. (1991) Theor Appl Genet 81:581-588); MAS (Velten et al. (1984) EMBO J 3:2723-2730); ALS promoter (U.S. Pat. No. 5,659,026), and the like. Other constitutive promoters are described in, for example, U.S. Pat. Nos. 5,608,149; 5,608,144; 5,604,121; 5,569,597; 5,466,785; 5,399,680; 5,268,463; 5,608,142; and 6,177,611.

In some examples an inducible promoter may be used. Pathogen-inducible promoters induced following infection by a pathogen include, but are not limited to those regulating expression of PR proteins, SAR proteins, beta-1,3-glucanase, chitinase, etc. See, for example, Redolfi et al. (1983) Neth J Plant Pathol 89:245-254; Uknes et al. (1992) Plant Cell 4:645-656; Van Loon (1985) Plant Mol Virol 4:111-116; WO 99/43819; Marineau et al. (1987) Plant Mol Biol 9:335-342; Matton et al. (1989) Mol Plant-Microbe Interact 2:325-331; Somsisch et al. (1986) Proc Natl Acad Sci USA 83:2427-2430; Somsisch et al. (1988) Mol Gen Genet 2:93-98; Yang (1996) Proc Natl Acad Sci USA 93:14972-14977; Chen et al. (1996) Plant J 10:955-966; Zhang et al. (1994) Proc Natl Acad Sci USA 91:2507-2511; Warner et al. (1993) Plant J 3:191-201; Siebertz et al. (1989) Plant Cell 1:961-968; U.S. Pat. No. 5,750,386 (nematode-inducible); and the references cited therein; and Cordero et al. (1992) Physiol Mol Plant Path 41:189-200 (Fusarium-inducible). Wound-inducible promoters include potato proteinase inhibitor (pin 11) gene (Ryan (1990) Ann Rev Phytopath 28:425-449; Duan et al. (1996) Nat Biotechnol 14:494-498); wun1 and wun2 (U.S. Pat. No. 5,428,148); win1 and win2 (Stanford et al. (1989) Mol Gen Genet 215:200-208); systemin (McGurl et al. (1992) Science 225:1570-1573); WIP1 (Rohmeier et al. (1993) Plant Mol Biol 22:783-792; Eckelkamp et al. (1993) FEBS Lett 323:73-76); MPI gene (Corderok et al. (1994) Plant J 6:141-150); and the like. Chemical-regulated promoters can be used to modulate the expression of a gene in a plant through the application of an exogenous chemical regulator. The promoter may be a chemical-inducible promoter, where application of the chemical induces gene expression, or a chemical-repressible promoter, where application of the chemical represses gene expression. Chemical-inducible promoters include, but are not limited to, the maize In2-2 promoter, activated by benzenesulfonamide herbicide safeners (De Veylder et al. (1997) Plant Cell Physiol 38:568-77), the maize GST promoter (GST-11-27, WO 93/01294), activated by hydrophobic electrophilic compounds used as pre-emergent herbicides, and the tobacco PR-1a promoter (Ono et al. (2004) Biosci Biotechnol Biochem 68:803-7) activated by salicylic acid. Other chemical-regulated promoters of interest include steroid-responsive promoters (see, for example, the glucocorticoid-inducible promoter in Schena et al. (1991) Proc Natl Acad Sci USA 88:10421-10425; and McNellis et al. (1998) Plant J 14:247-257); tetracycline-inducible and tetracycline-repressible promoters (Gatz et al. (1991) Mol Gen Genet 227:229-237; U.S. Pat. Nos. 5,814,618, and 5,789,156).

Tissue-preferred promoters can be utilized to target enhanced expression of a sequence of interest within a particular plant tissue. Tissue-preferred promoters include Kawamata et al. (1997) Plant Cell Physiol 38:792-803; Hansen et al. (1997) Mol Gen Genet 254:337-343; Russell et al. (1997) Transgenic Res 6:157-168; Rinehart et al. (1996) Plant Physiol 112:1331-1341; Van Camp et al. (1996) Plant Physiol 112:525-535; Canevascini et al. (1996) Plant Physiol 112:513-524; Lam (1994) Results Probl Cell Differ 20:181-196; and Guevara-Garcia et al. (1993) Plant J 4:495-505.

Leaf-preferred promoters are known and include, for example, Yamamoto et al. (1997) Plant J 12:255-265; Kwon et al. (1994) Plant Physiol 105:357-67; Yamamoto et al. (1994) Plant Cell Physiol 35:773-778; Gotor et al. (1993) Plant J 3:509-18; Orozco et al. (1993) Plant Mol Biol 23:1129-1138; Matsuoka et al. (1993) Proc Natl Acad Sci USA 90(20):9586-9590; and cab and rubisco promoters (Simpson et al. (1958) EMBO J 4:2723-2729; Timko et al. (1988) Nature 318:57-58).

Root-preferred promoters are known and include, for example, Hire et al. (1992) Plant Mol Biol 20:207-218 (soybean root-specific glutamine synthase gene); Miao et al. (1991) Plant Cell 3:11-22 (cytosolic glutamine synthase (GS) expressed in roots and root nodules of soybean; Keller & Baumgartner (1991) Plant Cell 3:1051-1061 (root-specific control element in the GRP 1.8 gene of French bean); Sanger et al. (1990) Plant Mol Biol 14:433-443 (root-specific promoter of *A. tumefaciens* mannopine synthase (MAS)); Bogusz et al., (1990) Plant Cell 2:633-641 (root-specific promoters isolated from *Parasponia andersonii* and *Trema tomentosa*); Leach & Aoyagi (1991) Plant Sci 79:69-76 (*A. rhizogenes* rolC and rolD root-inducing genes); Teeri et al. (1989) EMBO J 8:343-350 (*Agrobacterium* wound-induced TR1' and TR2' genes); VfENOD-GRP3 gene promoter (Kuster et al. (1995) Plant Mol Biol 29:759-772); and rolB promoter (Capana et al. (1994) Plant Mol Biol 25(4):681-691; phaseolin gene (Murai et al. (1983) Science 23:476-482; Sengopta-Gopalen et al. (1988) Proc Natl Acad Sci USA 82:3320-3324). See also U.S. Pat. Nos. 5,837,876; 5,750,386; 5,633,363; 5,459,252; 5,401,836; 5,110,732; and 5,023,179.

Seed-preferred promoters include both seed-specific promoters active during seed development, as well as seed-germinating promoters active during seed germination. See Thompson et al. (1989) BioEssays 10:108. Seed-preferred promoters include, but are not limited to, Cim1 (cytokinin-induced message); cZ19B1 (maize 19 kDa zein); and milps (myo-inositol-1-phosphate synthase); (see WO 00/11177 and U.S. Pat. No. 6,225,529). For dicots, seed-preferred promoters include, but are not limited to, bean β-phaseolin, napin, β-conglycinin, soybean lectin, cruciferin, and the like. For monocots, seed-preferred promoters include, but are not limited to, maize 15 kDa zein, 22 kDa zein, 27 kDa gamma zein, waxy, shrunken 1, shrunken 2, globulin 1, oleosin, and nuc1. See also WO 00/12733, where seed-preferred promoters from end1 and end2 genes are disclosed.

In further examples, methods are provided to identify a cis transcriptional regulatory region in an organism. A transcriptional regulatory region is any cis acting element that modulates the level of an RNA. Such elements include, but are not limited to, a promoter, an element of a promoter, an enhancer, an insulator, an intron, or a terminator region that is capable of modulating the level of RNA in a cell. The methods can be used to generate enhancer or promoter traps. In one example, the reporter or marker gene of the target site is expressed only when it inserts close to (enhancer trap) or within (promoter trap) another gene. The expression pattern of the reporter gene will depend on the enhancer elements of the gene near or in which the reporter gene inserts. In this example, the target site introduced into the cell or the organism can comprise a marker gene operably linked to a recombination site. In specific examples, the marker gene is flanked by dissimilar and non-recombinogenic recombination sites. The marker gene is either not operably linked to a promoter (promoter trap) or the marker gene is operably linked to a promoter that lacks enhancer elements (enhancer trap). Following insertion of the target site into the genome of the cell or the organism, the expression pattern of the marker gene is determined for each transformant. When a transformant with a marker gene expression pattern of interest is found, the enhancer/promoter trap sequences can be used as a probe to clone the gene that has that expression pattern, or alternatively to identify the promoter or enhancer regulating the expression. In addition, once a target site is integrated and under transcriptional control of a transcriptional regulatory element, the methods can further be employed to introduce a transfer cassette having a polynucleotide of interest into that target in the cell or the organism. A recombination event between the target site and the transfer cassette will allow the nucleotide sequence of interest to come under the transcriptional control of the promoter and/or enhancer element. See, for example, Geisler et al. (2002) Plant Physiol 130:1747-1753; Topping et al. (1997) Plant Cell 10:1713-245; Friedrich et al. (1991) Genes Dev 5:1513-23; Dunn et al. (2003) Appl Environ Microbiol 1197-1205; and von Melchner et al. (1992) Genes Dev 6:919-27.

In other examples, the target site is constructed to have multiple functional sets of dissimilar and non-recombinogenic recombination sites. Thus, multiple genes or polynucleotides can be stacked or ordered. In specific examples, this method allows for the stacking of sequences of interest at precise locations in the genome of a cell or an organism. Likewise, once a target site has been established within a cell or an organism, additional recombination sites may be introduced by incorporating such sites within the transfer cassette. Thus, once a target site has been established, it is possible to subsequently add sites or alter sites through recombination. Such methods are described in detail in WO 99/25821.

In one example, methods to combine multiple transfer cassettes are provided. The method comprises providing a target site comprising at least a first and a second functional recombination site, wherein the first and the second recombination sites are dissimilar and non-recombinogenic with respect to one another. A first transfer cassette comprising in the following order at least the first, a third, and the second functional recombination sites is provided wherein the first and the third recombination sites of the first transfer cassette flank a first polynucleotide of interest and wherein the first, the second, and the third recombination sites are dissimilar and non-recombinogenic with respect to one another and a first recombinase is provided, whereby the first transfer cassette is integrated at the target site. At least one of the first, the second, or the third recombination sites comprise a functional modified FRT recombination site provided herein.

A second transfer cassette comprising at least the second and the third recombination site is provided, wherein the second and the third recombination sites of the second transfer cassette flank a second polynucleotide of interest and a second recombinase is provided. The second recombinase recognizes and implements recombination at the second and third recombination sites and the second transfer cassettes is inserted at the target site, so that now the first and the second transfer cassette are now combined at the target site. In some examples, the target site is in an organism. In other examples, the target site is stably incorporated into the genome of the organism, for example a plant. In this example, multiple polynucleotides of interest are stacked at a predetermined target position in the genome of the organism.

Various alterations can be made to the stacking method to achieve the desired outcome of having the nucleotides sequences of interest stacked. For instance, a target site comprising in the following order at least a first, a second, and a third functional recombination site, wherein the recombination sites are dissimilar and non-recombinogenic with respect to one another is provided. A first transfer cassette comprising at least the first and the second recombination sites is provided, wherein the first and the second recombination site of the first transfer cassette flank a first polynucleotide of interest and a first recombinase is provided and recognizes and implements recombination at the first and the second recombination sites. At least one of the first, the second, or the third recombination sites comprise a functional modified FRT recombination site provided herein. A second transfer cassette comprising at least the second and the third recombination sites is provided, where the second and the third recombination sites of the second transfer cassette flank a second polynucleotide of interest. A second recombinase is provided. The recombinase recognizes and implements recombination at the second and third recombination sites.

In other examples methods are provided to minimize or eliminate expression resulting from random integration of DNA sequences into the genome of a cell or an organism, such as a plant. This method comprises providing a cell or an organism having stably incorporated into its genome a polynucleotide comprising the following components in the following order: a promoter active in the cell or the organism operably linked to an ATG translational start sequence operably linked to a target site comprising a first and a second functional recombination site, wherein the first and the second recombination sites are dissimilar and non-recombinogenic with respect to one another, and at least one of the first or the second recombination sites comprise a functional modified FRT recombination site provided herein. A transfer cassette comprising a polynucleotide of interest and the first and the second recombination site is introduced into the cell or the organism. The translational start sequence of the nucleotide sequence of interest in the transfer cassette has been replaced with the first recombination site. A recombinase is provided that recognizes and implements recombination at the recombination sites. Recombination with the target site results in the polynucleotide of interest being operably linked to the ATG translational start site of the target site contained in the polynucleotide. Operably linked indicates a functional fusion between adjacent elements, for example the linkage between a translational start, a promoter, and/or a recombination site indicates that the sequences are put together to generate an in-frame fusion that results in a properly expressed and functional gene product.

In one example a transfer cassette comprising RSc::S3 (noATG)-RSd, where RS represents a recombination site and S represents a polynucleotide of interest, is introduced into a plant having stably incorporated into its genome a polynucleotide comprising P1-RSa-S1-T1-RSb-P2-ATG::RSc-S2(no ATG)-T2-RSd, where P represents a promoter, T represents a terminator, RS represents a recombination site, and the symbol :: indicates operably linked adjacent elements. ATG::RS indicates that the sequences generate an in-frame fusion that results in a properly expressed and functional gene product. An appropriate recombinase is provided and recombination takes place at the recombination sites such that the sequence between the recombination sites of the transfer cassette replaces the sequence between the recombination sites of the target site, thereby yielding a directionally targeted and reintegrated new sequence. The new gene (S3) is now driven off of the P2 promoter in the target site. Designing constructs without an ATG start codon on the nucleotide sequence of interest results in an extremely low probability of expression of the introduced sequence if random integration occurs, since the transfer cassette would need to integrate behind an endogenous promoter region and in the correct reading frame.

The FRT recombination sites provided herein can be used to excise or invert a polynucleotide of interest. In this method, a polynucleotide is providing comprising, in the following order, a first functional recombination site, a polynucleotide of interest, and a second functional recombination site, where the first and the second recombination sites are recombinogenic with respect to one another. Depending on the orientation of the recombination sites, the polynucleotide of interest will be excised or inverted when the appropriate recombinase is provided. For example, directly repeated recombination sites will allow for excision of the polynucleotide of interest and inverted repeats will allow for an inversion of the polynucleotide of interest. Such methods can be employed either in vivo or in vitro.

Methods are also provided for the alteration of the recombination sites. The method provides for converting between different recombination sites and is based on previously described oligonucleotide mediated strategies for making specific targeted nucleotide modifications at a specified extrachromosomal or genomic target sequence (Yoon et al. (1996) Proc Natl Acad Sci USA 93:2071-2076; Cole-Strauss et al. (1996) Science 273:1386-1389; WO99/25853; WO99/25821; and WO 03/076574). Using these methods, the recombination sites can be targeted and modified in various ways. For example, a recombination site could be modified such that the functional pair of dissimilar and non-recombinogenic recombination sites are altered to generate two corresponding and recombinogenic recombination sites. Subsequent or concurrent expression of the appropriate recombinase in cells with the modified, corresponding/recombinogenic sites would lead to excision or inversion of the sequences between these new recombination sites, depending on the orientation of the sites, thereby specifically removing or turning off expression of the undesirable DNA sequences from the previously created construct containing these sequences. A non-limiting application of this approach would be, for example, in the case of a selectable marker which is required during initial steps of a breeding or backcrossing program to maintain and select for preferred individual plants, but which is not desired in the final product. Various oligonucleotide molecules for targeted modification of recombination sites can be designed and will vary depending on the recombination site being targeted. Exemplary oligonucleotides designed to modify recombination sites are described in WO99/25821 and WO 03/076574.

Recombination site conversion can also be employed in the methods to stack various polynucleotides in the genome of an organism, such as a plant. For example, the capabilities of the system can be extended by in vivo conversion of recombination sites to create new sites, rather than re-introducing new recombination sites into the organism. For example, conversion of dissimilar and non-recombinogenic recombination sites flanking a selectable marker to corresponding recombination sites would facilitate removal of a selectable marker, or to allow re-use of the same selectable marker in future transformations, providing a means to recycle selectable markers. A dissimilar recombination site with a known recombination frequency could also be modified in situ to a different recombination site with a similar or altered recombination frequency. Other modifications to alter the function, similarity, or recombinogencity can be accomplished.

In other examples, methods for locating preferred integration sites within the genome of a cell or an organism are provided. The method comprises introducing into a cell or an organism a target site comprising a nucleotide sequence operably linked to a promoter active in the organism. In specific examples, the target site is flanked by a first and a second functional recombination site, wherein the first and the second recombination sites are dissimilar and non-recombinogenic with respect to one another and at least one of the first or the second recombination sites comprises a modified FRT site provided herein. The level of expression of the polynucleotide is determined and the organism expressing the polynucleotide is selected. The cell or the organism harboring this DNA construct can then be characterized for site-specific integration potential, agronomic potential, and copy number. In other examples, a transfer cassette with the appropriate recombination site(s) is introduced into the cell or the organism having the target site described above. A recombinase that recognizes and implements recombination at the recombination sites is provided.

In another example a plurality of copies of the polynucleotide of interest is provided to the organism, such as a plant. In some examples this is accomplished by the incorporation of an extrachromosomal replicon into the transfer cassette (see WO 99/25855). In specific examples, the transfer cassette comprises a replicon and a polynucleotide of interest flanked by a directly repeated first and second recombination site, wherein the recombination sites are recombinogenic with respect to one another. When an appropriate recombinase is provided, the transfer cassette flanked by the directly repeated first and second recombination sites is excised from the genome of the organism, for example a plant, producing a viable replicon containing the polynucleotide of interest. Replication of this replicon results in a high number of copies of the replicon, the polynucleotide of interest, and/or prolongs the availability of the transfer cassette within the cell. In other examples, a third functional recombination site is present between the replicon and the polynucleotide of interest, wherein the third and the first recombination sites are functional sites and dissimilar and non-recombinogenic with respect to one another, and the presence of the appropriate recombinase allows integration of the polynucleotide of interest into a target site flanked by the third and the first recombination sites. In one example, at least one of the recombination sites used in the method comprises a functional, modified FRT recombination site provided herein.

A replicon comprises an extrachromosomal self-replicating unit. The replicon can originate from a virus, plasmid or cell and has the capacity for self-replication. In this example, the transfer cassette comprises both a replicon and the polynucleotide of interest. In one example, an organism having a target site stably incorporated into its genome is provided. A transfer cassette comprising in a 5' to 3' or 3' to 5' orientation: a first functional recombination site, a replicon, a second functional recombination site, the polynucleotide of interest, and a third functional recombination site is provided. The first and third recombination site of this transfer cassette are directly repeated, corresponding and recombinogenic with respect to each, and the second recombination site is dissimilar and non-recombinogenic with respect to the first and the third recombination sites, wherein at least one of the first, the second, or the third recombination sites comprise a functional modified FRT recombination site comprising a spacer sequence selected from the group consisting of SEQ ID NOS: 1, 2, 3, 4, 5, 6, 7, 8, 9, 10, 11, 12, 13, 14, 15, 16, 17, and 18. The transfer cassette can be contained in a T-DNA. In one example, the replicon is a viral replicon. A viral replicon is any DNA or RNA derived from a virus that undergoes episomal replication in a host cell. It contains cis-acting viral sequences necessary for replication, for example the replication origin. It may or may not contain trans-acting viral sequences needed for replication. The excised viral DNA is capable of acting as a replicon or replication intermediate, either independently, or with factors supplied in trans. The viral DNA may or may not encode infectious viral particles and furthermore may contain insertions, deletions, substitutions, rearrangements or other modifications. The viral DNA may contain heterologous DNA. In this case, heterologous DNA refers to any non-viral DNA or DNA from a different virus. For example, the heterologous DNA may comprise an expression cassette for a protein or RNA of interest.

Viral replicons suitable for use in the methods and compositions include those from geminivirus, begomovirus, curtovirus, or mastrevirus, (−) strand RNA viruses, (+) strand RNA viruses, potyvirus, potexvirus, and tobamovirus. Viral replicons can also include those of viruses having a circular DNA genome or replication intermediate, such as: Abuitilon mosaic virus (AbMV), African cassava mosaic virus (ACMV), banana streak virus (BSV), bean dwarf mosaic (BDMV), bean golden mosaic virus (BGMV), beet curly top virus (BCTV), beet western yellow virus (BWYV) and other luteoviruses, cassava latent virus (CLV), carnation etched virus (CERV), cauliflower mosaic virus (CaMV), chloris striate mosaic virus (CSMV), commelina yellow mottle virus (CoYMV), cucumber mosaic virus (CMV), dahlia mosaic virus (DaMV), digitaria streak virus (DSV), figwort mosaic virus (FMV), hop stunt viroid (HSV), maize streak virus (MSV), mirabilias mosaic virus (MMV), miscanthus streak virus (MiSV), potato stunt tuber virus (PSTV), panicum streak virus (PSV), potato yellow mosaic virus (PYMV), potato virus X (PVX), rice tungro bacilliform virus (RTBV), soybean chlorotic mottle virus (SoyCMV), squash leaf curl virus (SqLCV), strawberry vein banding virus (SVBV), sugarcane streak virus (SSV), thistle mottle virus (ThMV), tobacco mosaic virus (TMV), tomato golden mosaic virus (TGMV), tomato mottle virus (TMoV), tobacco ringspot virus (TobRV), tobacco yellow dwarf virus (TobYDV), tomato leaf curl virus (TLCV), tomato yellow leaf curl virus (TYLCV), tomato yellow leaf curl virus-Thailand (TYLCV-t) and wheat dwarf virus (WDV) and derivatives thereof. In some examples, the viral replicon may be from ACMV, MSV, WDV, TGMV or TMV.

In other examples, the insertion of a polynucleotide of interest into the genome of the organism occurs via a single cross over event. For instance, the transfer cassette can comprise a first recombination site, a replicon, a polynucleotide of interest, and a second recombination site. The first and second recombination sites of the transfer cassette are recombinogenic, dissimilar or corresponding, and directly repeated with respect to one another. The target site can comprise a single recombination site that is recombinogenic to one of the recombination sites of the transfer cassette. Such recombinogenic recombination sites can be designed such that integrative recombination events are favored over the excision reaction. Such recombinogenic recombination sites are known, for example, Albert et al. introduced nucleotide changes into the left 13 bp element (LE mutant lox site) or the right 13 bp element (RE mutant lox site) of the lox site. Recombination between the LE mutant lox site and the RE mutant lox site produces the wild-type loxP site and a LE+RE mutant site that is poorly recognized by the recombinase Cre, resulting in a stable integration event (Albert et al. (1995) Plant J 7:649-659). See also, for example, Araki et al. (1997) Nucleic Acids Res 25:868-872.

The transfer cassette is introduced into the organism comprising the target site. When an appropriate recombinase is provided, a recombination event between the recombinogenic recombination sites of the transfer cassette occurs. This event results in excision of the replicon, which may assume a circularized form. Replication of the replicon unit results in a high copy number of the replicon in the organism and prolongs the availability of the transfer cassette in the cell. A second recombination event between the recombinogenic recombination sites of the target site and transfer cassette allows the stable integration of the replicon unit and the polynucleotide of interest at the target site of the organism.

The methods provide for the targeted insertion of a polynucleotide of interest. If the polynucleotide of interest is introduced into an organism, it may impart various changes in the organism, particularly plants, including, but not limited to, modification of the fatty acid composition in the plant, altering the amino acid content of the plant, altering pathogen resistance, and the like. These results can be achieved by providing expression of heterologous products, increased expression of endogenous products in plants, or suppressed expression of endogenous produces in plants.

General categories of polynucleotides of interest include for example, those genes involved in information, such as zinc fingers, those involved in communication, such as kinases, and those involved in housekeeping, such as heat shock proteins. More specific categories of transgenes include for example, sequences encoding traits for agronomics, insect resistance, disease resistance, herbicide resistance, sterility, grain characteristics, oil, starch, carbohydrate, phytate, protein, nutrient, metabolism, digestability, kernel size, sucrose loading, and commercial products. Traits such as oil, starch, and protein content can be genetically altered. Modifications include increasing content of oleic acid, saturated and unsaturated oils, increasing levels of lysine and sulfur, providing essential amino acids, and also modification of starch. Hordothionin protein modifications to alter amino acid levels are described in U.S. Pat. Nos. 5,703,049, 5,885, 801, 5,885,802, 5,990,389. Other examples are a lysine and/or sulfur rich seed protein encoded by the soybean 2S albumin described in U.S. Pat. No. 5,850,016, and the chymotrypsin inhibitor from barley, described in Williamson et al. (1987) Eur J Biochem 165:99-106.

Derivatives of the coding sequences can be made to increase the level of preselected amino acids in the encoded polypeptide. For example, polynucleotides encoding the barley high lysine polypeptide (BHL) are derived from barley chymotrypsin inhibitor (WO 98/20133). Other proteins include methionine-rich plant proteins such as from sunflower seed (Lilley et al. (1989) *Proceedings of the World Congress on Vegetable Protein Utilization in Human Foods and Animal Feedstuffs*, ed. Applewhite (American Oil Chemists Society, Champaign, Ill.), pp. 497-502); corn (Pedersen et al. (1986) J Biol Chem 261:6279; Kirihara et al. (1988) Gene 71:3); and rice (Musumura et al. (1989) Plant Mol Biol 12:123).

Insect resistance polynucleotides may encode resistance to pests such as rootworm, cutworm, European Corn Borer, and the like. Such polynucleotides include, for example, *Bacillus thuringiensis* toxic protein genes (U.S. Pat. Nos. 5,366,892; 5,747,450; 5,737,514; 5,723,756; 5,593,881; and Geiser et al. (1986) Gene 48:109); and the like.

Polynucleotides encoding disease resistance traits include detoxification genes, such as against fumonosin (U.S. Pat. No. 5,792,931); avirulence (avr) and disease resistance (R) genes (Jones et al. (1994) Science 266:789; Martin et al. (1993) Science 262:1432; and Mihdrinos et al. (1994) Cell 78:1089); and the like.

Herbicide resistance traits may include genes coding for resistance to herbicides that act to inhibit the action of acetolactate synthase (ALS), in particular the sulfonylurea-type herbicides such as chlorosulfuron (e.g., the S4 and/or Hra mutations in ALS); genes coding for resistance to herbicides that act to inhibit action of glutamine synthase, such as phosphinothricin or basta (e.g., the bar gene); glyphosate (e.g., the EPSPS gene or the GAT gene; see for example patent publications US20040082770 and WO 03/092360) or other known genes. Antibiotic resistance can also be provided, for example the nptII gene encodes resistance to the antibiotics kanamycin and geneticin.

Sterility genes can also be encoded in an expression cassette and provide an alternative to physical detasseling. Examples of genes used in such ways include male tissue-preferred genes and genes with male sterility phenotypes such as QM, described in U.S. Pat. No. 5,583,210. Other genes include kinases and those encoding compounds toxic to either male or female gametophytic development.

Commercial traits can also be encoded on a gene or genes that could, for example increase starch for ethanol production, or provide expression of proteins. Another commercial use of transformed plants is the production of polymers and bioplastics such as described in U.S. Pat. No. 5,602,321. Genes such as β-Ketothiolase, PHBase (polyhydroxyburyrate synthase), and acetoacetyl-CoA reductase (see Schubert et al. (1988) J Bacteriol 170:5837-5847) facilitate expression of polyhydroxyalkanoates (PHAs).

Reduction of the activity of specific genes (also known as gene silencing, or gene suppression) is desirable for several aspects of genetic engineering in plants. Many techniques for gene silencing are well known, including but not limited to antisense technology (see, e.g., Sheehy et al. (1988) Proc Natl Acad Sci USA 85:8805-8809; and U.S. Pat. Nos. 5,107,065; 5,453,566; and 5,759,829); cosuppression (e.g., Taylor (1997) Plant Cell 9:1245; Jorgensen (1990) Trends Biotech 8:340-344; Flavell (1994) Proc Natl Acad Sci USA 91:3490-3496; Finnegan et al. (1994) Bio/Technology 12: 883-888; and Neuhuber et al. (1994) Mol Gen Genet 244:230-241); RNA interference (Napoli et al. (1990) Plant Cell 2:279-289; U.S. Pat. No. 5,034,323; Sharp (1999) Genes Dev 13:139-141; Zamore et al. (2000) Cell 101:25-33; Javier (2003) Nature 425:257-263; and, Montgomery et al. (1998) Proc Natl Acad Sci USA 95:15502-15507), virus-induced gene silencing (Burton, et al. (2000) Plant Cell 12:691-705; and Baulcombe (1999) Curr Op Plant Bio 2:109-113); target-RNA-specific ribozymes (Haseloff et al. (1988) Nature 334: 585-591); hairpin structures (Smith et al. (2000) Nature 407: 319-320; WO 99/53050; WO 02/00904; and WO 98/53083); ribozymes (Steinecke et al. (1992) EMBO J 11:1525; U.S. Pat. No. 4,987,071; and, Perriman et al. (1993) Antisense Res Dev 3:253); oligonucleotide mediated targeted modification (e.g., WO 03/076574 and WO 99/25853); Zn-finger targeted molecules (e.g., WO 01/52620; WO 03/048345; and WO 00/42219); and other methods or combinations of the above methods known.

The polynucleotides can be provided in a DNA construct. In addition, in specific examples recombination sites and/or the polynucleotide encoding an appropriate recombinase is also contained in the DNA construct. The cassette can include 5' and 3' regulatory sequences operably linked to the polynucleotide of interest. Alternatively, the DNA construct flanked by the appropriate recombination site can lack the 5' and/or 3' regulatory elements. In this instance, the DNA construct is designed such that in the presence of the appropriate recombinase a recombination event at the target site will result in the 5' and/or 3' regulatory regions being operably linked to the sequences of the DNA construct. Intervening sequences can be present between operably linked elements and not disrupt the functional linkage. The cassette may additionally contain at least one additional gene to be introduced into the organism. Alternatively, the additional gene(s) can be provided on multiple DNA constructs. Such a DNA construct may be provided with a plurality of restriction sites or recombination sites for insertion of the sequence of interest to be under the transcriptional regulation of the regulatory regions. The expression cassette may additionally contain selectable and/or screenable marker genes.

In some examples, the DNA construct can include in the 5' to 3' direction of transcription, a transcriptional and translational initiation region, a polynucleotide of interest, and a transcriptional and translational termination region functional in the organism of interest. In other examples, the DNA construct comprises a polynucleotide of interest 3' to a recombination site. In this example, the target site can comprise a promoter 5' to the corresponding recombination site, thereby, upon recombination, the nucleotide sequence of interest is operably linked to the promoter sequence. The various recombination sites provided herein can be positioned anywhere in the DNA construct, including the 5' UTR, 3' UTR, regulatory regions, introns and/or coding sequence.

The transcriptional initiation region, the promoter, may be native, analogous, foreign, or heterologous to the host organism or to the polynucleotide of interest. Additionally, the promoter may be the natural sequence or alternatively a synthetic sequence. Such constructs may change expression levels of the polynucleotide of interest in the organism. The termination region may be native or heterologous with the transcriptional initiation region, it may be native or heterologous with the operably linked polynucleotide of interest, or it may be native or heterologous with the host organism. Convenient termination regions are available from the Ti-plasmid of *A. tumefaciens*, such as the octopine synthase and nopaline synthase termination regions. See also Guerineau et al. (1991) Mol Gen Genet 262:141-144; Proudfoot (1991) Cell 64:671-674; Sanfacon et al. (1991) Genes Dev 5:141-149; Mogen et al. (1990) Plant Cell 2:1261-1272; Munroe et al. (1990) Gene 91:151-158; Ballas et al. (1989) Nucleic Acids Res 17:7891-7903; and Joshi et al. (1987) Nucleic Acids Res 15:9627-9639. The nucleotide sequence of interest can also be native or analogous or foreign or heterologous to the host organism.

Where appropriate, the codon usage in the nucleotide sequence of interest or the recombinase may be modified for expression in the transformed organism. For example, the genes can be synthesized using plant-preferred codons for improved expression. See, for example, Campbell & Gowri (1990) Plant Physiol 92:1-11 for a discussion of host-preferred codon usage. Methods are available for synthesizing plant-preferred genes. See, for example, U.S. Pat. Nos. 5,380,831, and 5,436,391, WO 99/25841, and Murray et al. (1989) Nucleic Acids Res 17:477-498.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The DNA construct may additionally contain 5' leader sequences. Such leader sequences can act to enhance translation. Translation leaders are known and include picornavirus leaders, for example, EMCV leader (Encephalomyocarditis 5' noncoding region) (Elroy-Stein et al. (1989) Proc Natl Acad Sci USA 86:6126-6130); potyvirus leaders, for example, TEV leader (Tobacco Etch Virus) (Gallie et al. (1995) Gene 165:233-238), MDMV leader (Maize Dwarf Mosaic Virus) (Allison et al. (1986) Virology 154:9-20; and Kong et al. (1988) Arch Virol 143:1791-1799), and human immunoglobulin heavy-chain binding protein (BiP) (Macejak et al. (1991) Nature 353:90-94); untranslated leader from the coat protein mRNA of alfalfa mosaic virus (AMV RNA 4) (Jobling et al. (1987) Nature 325:622-625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) Virology 81:382-385). See also, Della-Cioppa et al. (1987) Plant Physiol 84:965-968. Other methods or sequences known to enhance translation can also be utilized, for example, introns, and the like.

In preparing the DNA construct, the various DNA fragments may be manipulated to place the sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, transitions and/or transversions, may be involved.

Generally, the DNA construct will comprise a selectable marker gene for the selection of transformed cells. Selectable marker genes are utilized for the selection of transformed cells or tissues and have been discussed in detail elsewhere herein, as well as, exemplary promoters of interest.

The following examples are offered by way of illustration and not by way of limitation.

EXPERIMENTAL

Example 1

Generating Libraries Comprising Modified FRT Recombination Sites

Two complementary degenerate oligos containing FRT sequences with the 6 central spacer positions being randomly mutagenized were synthesized at Synthetic Genetics (San Diego, Calif.): Oligo 1:5'-gccagcatgcaagcttgaattccgaagttcctatactNNNNNNagaataggaacttcgagatctggatcc gcggaacg-3' (SEQ ID NO:52); and Oligo2: 5'-cgttccgcggatccagatctc-gaagttcctattctNNNNNNagta taggaacttcggaattcaagcttgcat-gctggc-3' (SEQ ID NO:53).

The spacer region is 8 bp. In this experiment, the central 6 bp region was targeted for modification, hence, the other two nucleotides are kept unchanged. One pmol of oligo 1 and one pmol of oligo 2 were annealed by heat denaturation at 95° C. for 2 minutes followed by gradual cooling to room temperature. Annealed oligos were digested with EcoRI and BamHI and ligated into the EcoRI/BamHI sites of a pSport1-derived vector to which 3 additional bases created a HpaI restriction site (BRL Life Technologies, Gaithersburg, Md.) and the PHP13273 vector containing a spectinomycin resistance gene to create a two modified FRT plasmid libraries. A 10:1 and 4:1 molar ratio of annealed oligo to pSport and PHP13273 was used for the respective ligation reactions. Under these ligation conditions, 10 out of 10 randomly picked colonies were found to contain a monomeric insertion of a modified FRT site. The modified FRT library referred to as "library A" is in the pSport vector and carries the antibiotic resistant marker ampicillin. The modified FRT library, referred to as "library B" is in the PHP13273 vector and carries the antibiotic resistant marker spectinomycin. A total number of 15,904 colonies were collected to make FRT library A and 19,600 colonies were collected to make the FRT library B. This represented a 4× coverage of the central 6 positions ($4^6=4096$) in the FRT site. Plasmid DNA was isolated from these two libraries and used for library scale screening.

Example 2

Library Scale Screening to Identify Recombinogenic Modified FRT Recombination Sites An equal molar amount of DNA from each of the modified FRT libraries A and B were mixed into one tube containing reaction buffer for FLP-mediated in vitro recombination. A typical 20 μl recombination reaction comprises 25 mM Tris Cl at pH 7.5, 1 mM MgCl$_2$, 5 mM DTT, 50 fmol library A DNA, 50 fmol library B DNA, and 2 μl FLP (0.07 μg/μl final). The reaction is carried out at 30° C., and aliquots taken at various time points. At each time point, 2 μl aliquots were taken and the reaction stopped by boiling for 1 min with gradual cooling to room temperature. Typically, samples were taken at 0, 2, 5, 10, 30, 60, and 90 minutes and could be used to evaluate fast vs slow reactive FRT sites. If only one time point was taken, the 90 minute timepoint was used.

Reaction samples were transferred into *E. coli* DH5α cells according to standard procedures. Equal aliquots of each transformation mixture was spread onto one plate each containing either ampicillin only, spectinomycin only, or containing both ampicillin and spectinomycin. Successfully recombined co-integrant DNA will carry both selection markers and thus, after transfer into *E. coli*, will confer resistance to both ampicillin and spectinomycin.

Those colonies with resistance to both antibiotics were picked and plasmid DNA was prepared using Montage 96-well HTP plasmid DNA preparation kit (Millipore, Billerica, Mass. USA). Candidate FRT sites were obtained by PCR using primers flanking recombined FRT sites in the co-integrate DNA. The PCR primers used were Forward primer: 5'-gcacatacaaatggacgaacgga-3 (SEQ ID NO:54) and Reverse primer: 5'-cctcttcgctattacgccagct-3'(SEQ ID NO:55). The PCR conditions were as follows: One cycle: 95° C., 1 min; 20 cycles: 95° C., 30 sec; 61° C., 2 min; one cycle:

67° C., 3 min; Hold: 4° C. The sequence of the amplified candidate FRT sites was determined by Cycle sequencing (essentially as described in Slatko et al. (1993) DNA Sequencing. In, *Current Protocols in Molecular Biology*, (ed. By Ausubel et al.) Ch. 7, pp 7.0.1-7.6.13. New York: John Wiley & Sons).

Example 3

Methods for Assaying Excision Efficiency of Recombinogenic Modified FRT Recombination Sites To assay recombinase-mediated excision efficiency of a candidate FRT site, excision vectors were made in which two copies of a candidate recombinogenic modified FRT site were cloned in direct orientation flanking the maize ubiquitin promoter sequence in pSport (BRL Life Technologies, Gaithersburg, Md.). An excision reaction was carried out under the following conditions: 3 µl miniprep excision vector DNA (2 mg/ml), 1 µl 10× buffer (250 mM Tris Cl at pH 7.5, 100 mM $MgCl_2$, 50 mM DTT), 5 µl dd$H_2O$, and 1 µl FLP (0.72 mg/ml). The reaction mixture was incubated at 30° C. for 30 min, boiled for 2 min, cooled to room temperature, digested with EcoRV and XhoI, and then subjected to agarose gel electrophoresis.

EcoRV generates a single cut in the pSport vector backbone while XhoI generates a single cut in the sequence of maize ubiquitin promoter. Double digestion of the non-recombined excision vector produces two fragments of 4332 bp and 769 bp. Double digestion of the product vector after excision takes place produces an additional fragment of 952 bp. The DNA fragments were quantified using Quantity One software from Bio-Rad Laboratories. As excision occurs, an increased amount of the 952 bp fragment is produced and less of the 769 bp fragment is produced. Thus, the ratio of the 952 bp fragment to that of the 769 bp fragment measures absolute excision efficiency. In this experiment, relative recombination excision efficiency (% excision efficiency) of a FRT site is calculated as the excision efficiency in the presence of native yeast FLP of a first modified FRT site with a second modified FRT site divided by the excision efficiency of a pair of wild-type FRT site (SEQ ID NO:39)×100%.

Various modified FRT recombination sites identified in the methods of Example 2 were analyzed for their ability to retain biological activity. Table 1 sets forth various functional modified FRT recombination sites and their relative recombination efficiency determined as outlined above.

TABLE 1

| FRT sites | SEQ ID NO for minimal modified FRT site | Spacer Sequence | SEQ ID No for modified spacer sequence | Excision Efficiency (%) |
|---|---|---|---|---|
| FRT1 | 39 | TTTCTAGA | 43 | 100 |
| FRT12 | 21 | TCTATGTA | 1 | 102 |
| FRT57 | 22 | TTTTCTAA | 2 | 82 |
| FRT85 | 23 | TTTCTTGA | 3 | 116 |
| FRT87 | 24 | TTTCTGGA | 4 | 93 |
| FRT53 | 25 | TGTAAAAA | 5 | 64 |
| FRT62 | 26 | TTTAGGTA | 6 | 72 |

TABLE 1-continued

| FRT sites | SEQ ID NO for minimal modified FRT site | Spacer Sequence | SEQ ID No for modified spacer sequence | Excision Efficiency (%) |
|---|---|---|---|---|
| FRT78 | 27 | TGAAAAGA | 7 | 60 |
| FRT34 | 28 | TGTAATGA | 8 | 34 |
| FRT70 | 29 | TATACAAA | 9 | 25 |
| FRT76 | 30 | TTCCATAA | 10 | 30 |
| FRT89 | 31 | TCTCTAGA | 11 | 39 |
| FRT43 | 32 | TTCCGAGA | 12 | 14 |
| FRT45 | 33 | TCTCTTGA | 13 | 5 |
| FRT55 | 34 | TCCACAGA | 14 | 7 |
| FRT65 | 35 | TGATTGGA | 15 | 18 |
| FRT69 | 36 | TTTTGTGA | 16 | 9 |
| FRT74 | 37 | TGAGAGAA | 17 | 5 |
| FRT86 | 38 | TTTCTCGA | 18 | 12 |
| FRT5 | 40 | CTTTTGAA | 44 | 15 |

*The spacer sequences were flanked by the wild type symmetrical 13 base pair element set forth in FIG. 1.

Example 4

Methods for Assaying Co-Integration Efficiency of Recombinogenic Modified FRT Recombination Sites The experiment was carried out as described in Example 2. Briefly, FRT1, 5, and 6 (SEQ ID NOS:39, 40, and 41) were individually cloned into EcoRI/BamHI sites of PHP13273 and modified pSport1 vector. 50 fmol DNA of FRT1 in PHP13273 (Spec$^r$) was mixed with 50 fmol DNA of FRT1 in modified pSport1 (Ap$^r$) in 20 µl reaction buffer containing 25 mM Tris-Cl at pH 7.5, 10 mM $MgCl_2$, 5 mM DTT, and 2 µl FLP (0.07 µg/µl final). At each time point, 2 µl aliquots were taken and the reaction stopped by boiling for 1 min with gradual cooling to room temperature. Reaction samples were transferred into *E. coli* DH5α cells according to standard procedures. Equal aliquots of each transformation mixture were spread onto one plate each containing ampicillin only, spectinomycin only, or containing both ampicillin and spectinomycin. Successfully recombined co-integrate DNA via FRT1 sites will carry both selection markers and thus, after transfer into *E. coli*, will confer resistance to both ampicillin and spectinomycin. Those colonies with resistance to both antibiotics were picked and co-integrated plasmid DNA was prepared for further analysis. Clones that are resistant to both antibiotics but do not harbor co-integrated plasmid DNA were subtracted in the calculation of co-integration frequency.

Co-integration frequency of FRT1 was determined by calculating the percentage of colonies harboring co-integrated plasmid DNA among colonies resistant to one antibiotic drug. Similarly, in vitro integration of FRT5 or FRT6 was performed and co-integration frequency of FRT5 or FRT6 was determined accordingly. The results are shown in Table 2.

TABLE 2

Percentage of co-integrants recovered from in vitro FLP-mediated recombination (%)

| | Time (h) | | | | |
|---|---|---|---|---|---|
| | 0 | 0.5 | 1.0 | 1.5 | 2.0 |
| FRT1 + FRT1 | 0.01 | 0.32 | 0.70 | 0.98 | 1.03 |
| FRT5 + FRT5 | 0.00 | 0.04 | 0.04 | 0.08 | 0.09 |
| FRT6 + FRT6 | 0.02 | 0.20 | 0.18 | 0.28 | 0.27 |

FLP-mediated in vitro recombination was performed as described before. When DNA containing dissimilar FRT sites are mixed in the reaction, such as in the previously described library-scale screening, intermolecular recombination between two corresponding FRT sites is further reduced. In reactions containing FRT1 sites only, FRT5 sites only, or FRT6 sites only, recombination between FRT1 sites is approximately 10-fold more efficient than between FRT5 sites and approximately 4-fold more efficient than between FRT6 sites (Table 2).

In this example, plasmid DNA containing three different FRT sites (FRT1, FRT5, and FRT6), each residing on modified pSport1 carrying $Ap^r$ selectable marker and PHP13273 carrying $Spec^r$, were mixed in the reaction. Among FRT1, FRT5, and FRT6, two different FRT sites do not recombine with each other. In the reaction having equimolar amount of DNA containing FRT sites of FRT1, FRT5, and FRT6, recombination efficiency between any two corresponding FRT sites is reduced. The results are shown in Table 3. The combined co-integration frequency between two FRT1 sites, two FRT5 sites, and two FRT6 sites was 0.09% after 90 minutes, approximately 10-fold less than that of the reaction having the FRT1 site only. The majority of co-integrates is from recombination via the most efficient FRT sites, FRT1, in the reaction as indicated by the fact that all of the 10 randomly picked co-integrates were recombination products of FRT1 sites. In the reaction having lower molar amount of DNA containing FRT1 site (molar ratio among FRT1, FRT5, and FRT6 is: 0.04:1.00:1.00), the overall recombination was further reduced. Furthermore, none of the 10 randomly picked co-integrates was recombination product of FRT1 sites.

fer cassette, target site, and/or recombinase provided herein. If the polynucleotide does not include a selectable marker, another polynucleotide containing a selectable marker gene can be co-precipitated on the particles used for bombardment. For example, a plasmid containing the PAT gene (Wohlleben et al. (1988) Gene 70:25-37) which confers resistance to the herbicide Bialaphos can be used. Transformation is performed as follows.

The ears are surface sterilized in 50% Chlorox bleach plus 0.5% Micro detergent for 20 minutes, and rinsed two times with sterile water. The immature embryos are excised and placed embryo axis side down (scutellum side up), 25 embryos per plate. These are cultured on 560L agar medium 4 days prior to bombardment in the dark. Medium 560L is an N6-based medium containing Eriksson's vitamins, thiamine, sucrose, 2,4-D, and silver nitrate. The day of bombardment, the embryos are transferred to 560Y medium for 4 hours and are arranged within the 2.5-cm target zone. Medium 560Y is a high osmoticum medium (560L with high sucrose concentration).

A plasmid vector comprising a polynucleotide of interest operably linked to the selected promoter is constructed. This plasmid DNA, plus plasmid DNA containing a PAT selectable marker if needed, is precipitated onto 1.0 µm (average diameter) gold pellets using a CaCl2 precipitation procedure as follows: 100 µl prepared gold particles (0.6 mg) in water, 20 µl (2 µg) DNA in TrisEDTA buffer (1 µg total), 100 µl 2.5 M CaC12, 40 µl 0.1 M spermidine.

Each reagent is added sequentially to the gold particle suspension. The final mixture is sonicated briefly. After the precipitation period, the tubes are centrifuged briefly, liquid removed, washed with 500 µl 100% ethanol, and centrifuged again for 30 seconds. Again the liquid is removed, and 60 µl 100% ethanol is added to the final gold particle pellet. For particle gun bombardment, the gold/DNA particles are briefly sonicated and 5 µl spotted onto the center of each macrocarrier and allowed to dry about 2 minutes before bombardment.

The sample plates are bombarded at a distance of 8 cm from the stopping screen to the tissue, using a DuPont biolis-

TABLE 3

| FRT Sites* | Co-integrate (%) | FRT1 co-integrate/Total co-integrate analyzed |
|---|---|---|
| FRT1 ($Ap^r$, 50fmol) + FRT1 ($Spec^r$, 50fmol) | 0.98 | 10/10 |
| FRT5 ($Ap^r$, 50fmol) + FRT5 ($Spec^r$, 50fmol) | 0.08 | NA |
| FRT6 ($Ap^r$, 50fmol) + FRT6 ($Spec^r$, 50fmol) | 0.28 | NA |
| FRT1 ($Ap^r$, 16fmol) + FRT1 ($Spec^r$, 16fmol) + FRT5 ($Ap^r$, 16fmol) + FRT5 ($Spec^r$, 16fmol) + FRT6 ($Ap^r$, 16fmol) + FRT6 ($Spec^r$, 16fmol) | 0.09 | 10/10 |
| FRT1 ($Ap^r$, 0.8fmol) + FRT1 ($Spec^r$, 0.8fmol) + FRT5 ($Ap^r$, 20fmol) + FRT5 ($Spec^r$, 20fmol) + FRT6 ($Ap^r$, 20fmol) + FRT6 ($Spec^r$, 20fmol) | 0.07 | 0/10 |

*Selection marker and molar amount of DNA used in the reaction are included in parenthesis.

Example 5

Plant Transformation

A. Particle Bombardment Transformation and Regeneration of Maize Callus

Immature maize embryos from greenhouse or field grown High type II (HiII) donor plants are bombarded with an isolated polynucleotide comprising a recombination site, transtics helium particle gun. All samples receive a single shot at 650 PSI, with a total of ten aliquots taken from each tube of prepared particles/DNA.

Four to 12 hours post bombardment, the embryos are moved to 560P (a low osmoticum callus initiation medium similar to 560L but with lower silver nitrate), for 3-7 days, then transferred to 560R selection medium, an N6 based medium similar to 560P containing 3 mg/liter Bialaphos, and subcultured every 2 weeks. After approximately 10 weeks of selection, callus clones are sampled for PCR and/or activity of the polynucleotide of interest. Positive lines are transferred to 288J medium, an MS-based medium with lower sucrose and hormone levels, to initiate plant regeneration. Following somatic embryo maturation (2-4 weeks), well-developed somatic embryos are transferred to medium for germination and transferred to the lighted culture room. Approximately 7-10 days later, developing plantlets are transferred to medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to Classic™ 600 pots (1.6 gallon) and grown to maturity. Plants are monitored for expression of the polynucleotide of interest.

B. *Agrobacterium*-Mediated Transformation and Regeneration of Maize Callus

For *Agrobacterium*-mediated transformation of maize, a polynucleotide comprising a recombination site, transfer cassette, target site, and/or recombinase provided herein is used with the method of Zhao (U.S. Pat. No. 5,981,840).

Briefly, immature embryos are isolated from maize and the embryos contacted with a suspension of *Agrobacterium* containing a polynucleotide of interest, where the bacteria are capable of transferring the nucleotide sequence of interest to at least one cell of at least one of the immature embryos (step 1: the infection step). In this step the immature embryos are immersed in an *Agrobacterium* suspension for the initiation of inoculation. The embryos are co-cultured for a time with the *Agrobacterium* (step 2: the co-cultivation step). Following this co-cultivation period an optional "resting" step may be performed (step 3: resting step). The immature embryos are cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). The immature embryos are cultured on solid medium with a selective agent resulting in the selective growth of transformed cells. The callus is then regenerated into plants (step 5: the regeneration step), and calli grown on selective medium are cultured on solid medium to regenerate the plants.

C. Transformation of Dicots

A polynucleotide comprising a recombination site, transfer cassette, target site, and/or recombinase provided herein can be introduced into embryogenic suspension cultures of soybean by particle bombardment using essentially the methods described in Parrott, et al. (1989) *Plant Cell Rep.* 7:615-617. This method, with modifications, is described below.

Seed is removed from pods when the cotyledons are between 3 and 5 mm in length. The seeds are sterilized in a bleach solution (0.5%) for 15 minutes after which time the seeds are rinsed with sterile distilled water. The immature cotyledons are excised by first cutting away the portion of the seed that contains the embryo axis. The cotyledons are then removed from the seed coat by gently pushing the distal end of the seed with the blunt end of the scalpel blade. The cotyledons are then placed in Petri dishes (flat side up) with SB1 initiation medium (MS salts, B5 vitamins, 20 mg/L 2,4-D, 31.5 g/L sucrose, 8 g/L TC Agar, pH 5.8). The Petri plates are incubated in the light (16 hr day; 75-80 µE) at 26° C. After 4 weeks of incubation the cotyledons are transferred to fresh SB1 medium. After an additional two weeks, globular stage somatic embryos that exhibit proliferative areas are excised and transferred to FN Lite liquid medium (Samoylov, et al. (1998) *In Vitro Cell Dev. Biol.—Plant* 34:8-13). About 10 to 12 small clusters of somatic embryos are placed in 250 ml flasks containing 35 ml of SB172 medium. The soybean embryogenic suspension cultures are maintained in 35 mL liquid media on a rotary shaker, 150 rpm, at 26° C. with florescent lights (20 µE) on a 16:8 hour day/night schedule. Cultures are sub-cultured every two weeks by inoculating approximately 35 mg of tissue into 35 mL of liquid medium.

Soybean embryogenic suspension cultures are then transformed using particle gun bombardment (Klein et al., (1987) *Nature* 327:70; U.S. Pat. No. 4,945,050). A BioRad Biolistica PDS1000/HE instrument can be used for these transformations. A selectable marker gene, which is used to facilitate soybean transformation, is a chimeric gene composed of the 35S promoter from Cauliflower Mosaic Virus (Odell et al. (1985) *Nature* 313:810-812), the hygromycin phosphotransferase gene from plasmid pJR225 (from *E. coli*; Gritz et al. (1983) *Gene* 25:179-188) and the 3' region of the nopaline synthase gene from the T-DNA of the Ti plasmid of *Agrobacterium tumefaciens*.

To 50 µL of a 60 mg/mL 1 µm gold particle suspension is added (in order): 5 µL DNA (1 µg/µL), 20 µl spermidine (0.1 M), and 50 µL CaCl2 (2.5 M). The particle preparation is agitated for three minutes, spun in a microfuge for 10 seconds and the supernatant removed. The DNA-coated particles are washed once in 400 µL 70% ethanol and resuspended in 40 µL of anhydrous ethanol. The DNA/particle suspension is sonicated three times for one second each. Five µL of the DNA-coated gold particles are then loaded on each macro carrier disk.

Approximately 300-400 mg of a two-week-old suspension culture is placed in an empty 60×15 mm petri dish and the residual liquid removed from the tissue with a pipette. Membrane rupture pressure is set at 1100 psi and the chamber is evacuated to a vacuum of 28 inches mercury. The tissue is placed approximately 8 cm away from the retaining screen, and is bombarded three times. Following bombardment, the tissue is divided in half and placed back into 35 ml of FN Lite medium.

Five to seven days after bombardment, the liquid medium is exchanged with fresh medium. Eleven days post bombardment the medium is exchanged with fresh medium containing 50 mg/mL hygromycin. This selective medium is refreshed weekly. Seven to eight weeks post bombardment, green, transformed tissue will be observed growing from untransformed, necrotic embryogenic clusters. Isolated green tissue is removed and inoculated into individual flasks to generate new, clonally propagated, transformed embryogenic suspension cultures. Each new line is treated as an independent transformation event. These suspensions are then subcultured and maintained as clusters of immature embryos, or tissue is regenerated into whole plants by maturation and germination of individual embryos.

D. DNA Isolation from Callus and Leaf Tissues

Putative transformation events can be screened for the presence of the transgene. Genomic DNA is extracted from calli or leaves using a modification of the CTAB (cetyltrimethylammonium bromide, Sigma H5882) method described by Stacey and Isaac (1994 In Methods in Molecular Biology Vol. 28, pp. 9-15, Ed. P. G. Isaac, Humana Press, Totowa, N.J.). Approximately 100-200 mg of frozen tissue is ground into powder in liquid nitrogen and homogenised in 1 ml of CTAB extraction buffer (2% CTAB, 0.02 M EDTA, 0.1 M Tris-Cl pH 8, 1.4 M NaCl, 25 mM DTT) for 30 min at 65° C. Homogenised samples are allowed to cool at room temperature for 15 min before a single protein extraction with approximately 1 ml 24:1 v/v chloroform:octanol is done.

Samples are centrifuged for 7 min at 13,000 rpm and the upper layer of supernatant collected using wide-mouthed pipette tips. DNA is precipitated from the supernatant by incubation in 95% ethanol on ice for 1 h. DNA threads are spooled onto a glass hook, washed in 75% ethanol containing 0.2 M sodium acetate for 10 min, air-dried for 5 min and resuspended in TE buffer. Five μl RNAse A is added to the samples and incubated at 37° C. for 1 h. For quantification of genomic DNA, gel electrophoresis is performed using a 0.8% agarose gel in 1×TBE buffer. One microlitre of each of the samples is fractionated alongside 200, 400, 600 and 800 ng μl-1λ uncut DNA markers.

Example 6

Comparing Relative Recombination Efficiency of Dissimilar FRT Sequences in Maize Cells Two assays are provided that measure relative transgene activation rates as a result of FLP-mediated excision, which brings a promoter and transgene into functional proximity. The method can be used to characterize the recombination efficiency of either corresponding and/or dissimilar recombination sites and thereby determine if the sites are recombinogenic or non-recombinogenic with one another.

Two assays are discussed below: (A) scoring activation of Yellow Fluorescence Protein (YFP) in individual cells and (B) scoring luciferase activity.

A. Fluorescence Assay

Three transgenic expression cassettes (outlined in Table 4) are introduced in either a FRT-Test treatment or a control treatment.

TABLE 4

| FRT-Test construct | Control construct |
|---|---|
| CPN60:FRTx:GUS:FRTx:YFP:35s term<br>Actin::CFP::nos<br>Ubi::FLP::pinII | CPN60:FRTx:YFP:35s term<br>Actin::CFP::nos<br>Ubi::FLP::pinII |

YFP = yellow fluorescence protein;
CFP = cyan fluorescence protein;
CPN60 = maize chaparonin 60 promoter (Close (1993) Master's Thesis, Iowa State University).

In both the control and FRT-testing treatments, the relevant (or appropriate) three expression cassettes are mixed in equimolar ratios, and introduced into scutellar cells of Hi-II immature embryos using standard particle delivery methods. After two days, the numbers of cyan- and yellow-fluorescent cells are counted using a Leica epifluorescent stereomicroscope. The number of cyan-fluorescing cells is used to normalize between treatments by providing a relative measure of how many cells received sufficient DNA to express the transgenes. To validate this assay system, FRT1 is used for the first experiment. As a control treatment, a mixture of the following three plasmids is used: Actin::Cyan FP::nos, CPN60:FRT1:YFP:35s term, and Ubi::FLP::pinII. In the control treatment, when these three plasmids are co-introduced and the numbers of cyan and yellow cells are scored two days later, the numbers of cyan and yellow cells in the population is expected to be approximately equivalent (1:1).

In the FRT-Test treatment, when FRT1 is used in the excision-activated cassette (CPN60:FRT1:GUS:FRT1:YFP:35s term), it is expected that approximately 90-95% of the cells expressing cyan fluorescence also express yellow fluorescence, i.e. excision of the FRT1-flanked region is relatively efficient. Based on previous studies with FRT5, when FRT5 is used in the excision cassette, the frequency of cyan fluorescing cells that also express the yellow fluorescent protein is expected to drop to approximately 15% of that observed in the FRT1 treatment.

The excision-activated cassette can also be used to determine if two dissimilar FRT recombination sites are recombinogenic or non-recombinogenic. To determine if FRT1 and FRT5 are recombinogenic or non-recombinogenic with respect to one another, an excision-activated cassette comprising CPN60:FRT1:GUS:FRT5:YFP:35s term is constructed. As outlined in Table 4, the three expression cassettes are mixed in equimolar ratios, and introduced into scutellar cells of Hi-II immature embryos using standard particle delivery methods. After two days, the numbers of cyan- and yellow-fluorescent cells are counted using a Leica epifluorescent stereomicroscope. The number of cyan-fluorescing cells is used to normalize between treatments by providing a relative measure of how many cells received sufficient DNA to express the transgenes.

When the excision cassette comprises a FRT1 and a FRT5 recombination site, the frequency of cyan fluorescing cells that also express the yellow fluorescent protein is expected to drop to approximately less than 1% of that observed in when an excision cassette comprising two FRT1 recombination sites is employed. The sites are therefore determined to be non-recombinogenic.

B. Assay Based on Activation of Luciferase Enzymatic Activity

The second assay system again uses a mixture of plasmids in equimolar amounts, cobombarded into scutellar cells of Hi-II immature embryos. For this assay the three plasmids are shown in Table 5.

TABLE 5

| FRT-Test Treatment | Control |
|---|---|
| Actin::FRTx:GUS:FRTx:FF-luciferase::nos* | Actin::FRTx:FF-luciferase::nos* |
| Nos::Renilla-luciferase::35S term | Nos::Renilla-luciferase::35S term |
| Ubi::FLP::pinII | Ubi::FLP::pinII |

*FF = firefly luciferase; Renilla-luciferase (Minko et al. (1999) Mol. Gen. Genet. 262: 421-425)

Again, FRT1 is used to validate the assay system. In the control treatment, Actin:FRT1:FF-luciferase::nos, Nos::Renilla-luciferase::35S term, and Ubi::FLP::pinII are introduced into scutellar cells and after 2 days the tissue is extracted using methods and solutions provided in the Promega Dual-luciferase Assay Kit (Promega, Madison, Wis. 53711). Multiple scutella are individually extracted, and the extracts sequentially assayed for firefly and then Renilla luciferase activity using a Fluoroscan. With this mixture of constructs it is expected that the expressed firefly luciferase protein produces approximately 5000 relative light units and the Renilla luciferase produces about 15,000. When FRT1 is used in the excision-activated cassette (Actin:FRT1:GUS:FRT1:Firefly luci:35s term), the firefly luciferase is expected to produce about 4500 light units (about 90% of the control treatment). When FRT 5 is used in the excision cassette, the firefly luciferase activity is expected to drop to approximately 670 light units (~15% of FRT1).

Example 7

Targeting the Insertion of a Polynucleotide of Interest into Maize

A. Establishing a Target Line

For evaluation of FRT sequences for site-specific integration, a target site is first created by stably integrating a polynucleotide comprising a target site having two functional FRT recombination sites, where the recombination sites are dissimilar and non-recombinogenic with respect to one another. This initial transformation is accomplished in Hi-II germplasm (or inbred lines) using standard *Agrobacterium* transformation methods for maize (see Example 5B). For example, to compare the relative efficiency of FRT5 and FRT87 in the site-specific integration system, the following constructs are separately introduced into Hi-II germplasm:

PHP20807:

RB-Ubi:Ubi-intron:FRT1:Yellow Fluorescent Protein::pinII/Ubi:Ubi-intron:

GAT::pinII/In2-1 term:GUS:FRT5:Os-Actin-intron:Os-Actin Pro-LB

PHP20705:

RB-Ubi:Ubi-intron:FRT1:Yellow Fluorescent Protein::pinII/Ubi:Ubi-intron:

GAT::pinII/In2-1 term:GUS:FRT87:Os-Actin-intron:Os-Actin Pro-LB

Stable transformants are selected by looking for yellow-fluorescent callus growing on glyphosate-containing medium. Plants are regenerated and sent to the greenhouse. Leaf samples are taken for Southern analysis. Single-copy transgenic plants are grown to maturity and crossed to wild-type Hi-II (or inbred lines). These transgenic events now contain the FRT1-5 or FRT1-87 target site, and are ready for site-specific recombinase-mediated recombination.

B. Introduction of the Transfer Cassette Using Particle Bombardment.

Immature embryos from the line having the target sites as evidenced by expression of yellow fluorescence are used for the subsequent re-transformation. During the re-transformation process, transfer cassettes are introduced using standard particle bombardment methods (e.g., see Example 5A). For progeny plants that contain the integrated T-DNA from PHP20705 (the FRT1-FRT87 target site), the following insert comprising the transfer cassette is used for re-transformation using the particle gun:

PHP20915:

RB-CaMV35S Term/FRT1:bar::pinII/Ubi:Ubi-intron:*Renilla* luciferase::pinII/In2-1 term:Am-Cyan1:FRT87/CaMV35S Term-LB.

Progeny immature embryos that contain the integrated T-DNA from PHP20807 (the FRT1-FRT5 target site) are re-transformed using the particle gun with the following plasmid:

PHP20954:

RB-CaMV35S Term/FRT1:bar::pinII/Ubi:Ubi-intron:*Renilla* luciferase::pinII/In2-1 term:Am-Cyan1:FRT5/CaMV35S Term-LB.

For both of the plasmids comprising the transfer cassette (PHP20915 and PHP20954), the bar and Cyan FP genes have no promoter. To reduce the likelihood that random integration would result in spurious expression of either gene, the CaMV35S terminator has been placed upstream of the FRT1 site. Each of these plasmids is co-transformed into immature embryos from their respective target-lines along with plasmid PHP5096 (Ubi:Ubi-intron::FLPm::pinII). Either PHP20915 or PHP20954 are mixed with the FLP-containing plasmid (PHP5096), using 100 ng of the FRT-containing plasmid and 10 ng of the FLP plasmid per bombardment.

To prepare DNA for delivery, DNA solutions are added to 50 µl of a gold-particle stock solution (0.1 µg/µl of 0.6 micron gold particles). For example, 10 µl of a 0.1 µg/µl solution of PHP20915 or PHP20954, and 10 µl of a 0.01 µg/µl solution of PHP5096 are first added to 30 µl of water. To this DNA mixture, 50 µl, of the gold stock solution is added and the mixture briefly sonicated. Next 5 µl, of TFX-50 (Promega Corp., 2800 Woods Hollow Road, Madison Wis. 53711) is added and the mixture is placed on a rotary shaker at 100 rpm for 10 minutes. The mixture is briefly centrifuged to pellet the gold particles and remove supernatant. After removal of the excess DNA/TFX solution, 120 µl of absolute EtOH is added, and 10 µl aliquots are dispensed onto the macrocarriers typically used with the DuPont PDS-1000 Helium Particle Gun. The gold particles with adhered DNA are allowed to dry onto the carriers and then these are used for standard particle bombardment. After re-transformation delivery of the plasmid having the transfer cassette plus the FLP-containing plasmid, the immature embryos are placed onto 560P medium for two weeks to recover, and then moved to medium containing 3 mg/l bialaphos for selection. Successful recombination at both the 5' (FRT1) and 3' (FRT87 or 5) recombination target sites will result in activation of both the bar gene and the Cyan Fluorescent Protein gene when these structural genes are brought into functional proximity with the Ubi or Actin promoters, respectively. Thus, proper site-specific integration events will be selected based on the newly activated phenotypes. When these calli are large enough for sampling, genomic DNA is extracted from the tissue, and is analyzed using PCR for the presence of products that result from amplification of fragments using primers that span the newly formed promoter-gene junctions. Finally, leaf samples are taken from regenerated plants for Southern analysis, to verify proper recombination to transfer of the donor cassette into the genomic target locus. Once successful recombinant loci have been verified, plants are grown to maturity and outcrossed or selfed.

C. Introduction of the Transfer Cassette by Crossing

Transfer cassettes can be provided by sexual crossing. In this example stable transgenic, single-copy target events are again used containing a single-copy of the T-DNA cassettes originally delivered from *Agrobacterium* containing PHP20705 or PHP20807. However, in this method stable transgenic donor events are produced using either of two T-DNA *Agrobacterium* vectors shown below.

1. The donor vector that complements PHP20705:

RB-Axig1::LEC1::pinII/Ubi Pro: Ubi-intron::YFP::pinII/-LB and

RB-In2::FLP::pinII-CaMV35S Term/FRT1:bar::pinII/Ubi:Ubi-intron:*Renilla* luciferase::pinII/In2-1 term:Am-Cyan1:FRT87/CaMV35S Term-LB 2. The donor vector that complements PHP20807:

RB-Axig1::LEC1::pinII/Ubi Pro: Ubi-intron::YFP::pinII/-LB and

RB-In2::FLP::pinII-CaMV35S Term/FRT1:bar::pinII/Ubi: Ubi-intron:*Renilla* luciferase::pinII/In2-1 term:Am-Cyan1: FRT5/CaMV35S Term-LB For both of the above plasmids, the expression cassettes in the first T-DNA provide a means of selecting the transgenic donor lines after *Agrobacterium*-mediated transformation. The second T-DNA provides the components for crossing-mediated cassette exchange. Note that for both constructs, the inducible FLP expression cassette is outside the FRT sites and thus this is not transferred into the target site upon successful exchange.

The recombination events having the transfer cassette are selected by visual selection for vigorously growing, yellow-fluorescent calli, regenerated, grown to maturity and crossed to produce donor seed having the transfer cassette. Seed from a target event containing the T-DNA fragment from PHP20705 as well as seed from a donor event containing the T-DNA from Donor plasmid #1 above are planted and grown to maturity. Upon flowering, reciprocal crosses are made between the target and donor plants. The resultant seed are planted and screened for the newly activated phenotypes that indicate successful recombination at the two dissimilar FRT sites, in this case activation of bialaphos resistance indicative of proper recombination at FRT5 and activation of Cyan fluorescence indicative of proper recombination at FRT87. Similar crosses are done using target and transfer lines generated with PHP20807 and Donor plasmid #2, respectively.

Example 8

Transformation of Bacterial Cells

The novel recombination sites provided herein can also be evaluated and used in bacterial cells, such as *E. coli*. Many commercially available competent cell lines and bacterial plasmids are well known and readily available. Isolated polynucleotides for transformation and transformation of bacterial cells can be done by any method known in the art. For example, methods of *E. coli* and other bacterial cell transformation, plasmid preparation, and the use of phages are detailed, for example, in *Current Protocols in Molecular Biology* (F. M. Ausubel et al. (eds.) (1994) a joint venture between Greene Publishing Associates, Inc. and John Wiley & Sons, Inc.). For example, an efficient electroporation protocol (Tung & Chow, *Current Protocols in Molecular Biology*, Supplement 32, Fall 1995) is summarized below.

Inoculate 100 ml LB medium with 1 ml *E. coli* overnight culture. Incubate at 37° C. with vigorous shaking until culture reached OD600=0.6. Chill culture on ice 30 min, pellet cells by centrifuging 4,000×g for 15 min at 4° C. Wash cell pellet twice with 50 ml ice-cold 10% glycerol. After final wash, resuspend cell pellet to a final volume of 0.2 ml in ice-cold GYT medium (10% v/v glycerol; 0.125% w/v yeast extract; 0.25% w/v trytone). Electroporate in prechilled cuvettes using manufacturer's conditions, for example 0.5 ng plasmid DNA/transformation using Gene Pulser (BioRad) set to 25 µF, 200 ohms, 2.5 kV. Immediately after electroporation, add 1 ml SOC medium and transfer cells to a culture tube. Incubate at 37° C. for 1 hr. Plate aliquots of cells on selective agar plates and incubate overnight at 37° C.

Example 9

Transformation of Yeast

The novel recombination sites provided herein can also be evaluated and used in yeast cells, from which FLP recombinase and FRT sites were initially isolated. Many commercially and/or publicly available strains of *S. cerevisiae* are available, as are the plasmids used to transform these cells. For example, strains are available from the American Type Culture Collection (ATCC, Manassas, Va.) and includes the Yeast Genetic Stock Center inventory, which moved to the ATCC in 1998. Other yeast lines, such as *S. pombe* and *P. pastors*, and the like are also available. For example, methods of yeast transformation, plasmid preparation, and the like are detailed, for example, in *Current Protocols in Molecular Biology* (F. M. Ausubel et al. (eds.) (1994) a joint venture between Greene Publishing Associates, Inc. and John Wiley & Sons, Inc., see Unit 13 in particular). Transformation methods for yeast include spheroplast transformation, electroporation, and lithium acetate methods. A versatile, high efficiency transformation method for yeast is described by Gietz & Woods ((2002) *Methods Enzymol.* 350:87-96) using lithium acetate, PEG 3500 and carrier DNA.

Example 10

Transformation of Mammalian Cells

The novel recombination sites provided herein can also be evaluated and used in mammalian cells, such as CHO, HeLa, BALB/c, fibroblasts, mouse embryonic stem cells and the like. Many commercially available competent cell lines and plasmids are well known and readily available, for example from the ATCC (Manassas, Va.). Isolated polynucleotides for transformation and transformation of mammalian cells can be done by any method known in the art. For example, methods of mammalian and other eukaryotic cell transformation, plasmid preparation, and the use of viruses are detailed, for example, in *Current Protocols in Molecular Biology* (F. M. Ausubel et al. (eds.) (1994) a joint venture between Greene Publishing Associates, Inc. and John Wiley & Sons, Inc., see Unit 9 in particular). For example, many methods are available, such as calcium phosphate transfection, electroporation, DEAE-dextran transfection, liposome-mediated transfection, microinjection as well as viral techniques.

Example 11

Methods for In Vitro Recombinational Cloning

In examples A, B, and C below, the two parental nucleic acid molecules (e.g., plasmids) are called the "insert donor" and the "vector donor." The insert donor contains a segment that will become joined to a new sequence contributed by the vector donor. The recombination event produces two daughter molecules: the first referred to as the product (the desired new clone) and the second referred to as the by-product.

In the examples below, two pairs of plasmids are constructed to perform the in vitro recombinational cloning method in two different ways. One pair of plasmids, Plasmid A and plasmid B, are constructed with a FRT site and a lox site, to be used with Cre and FLP recombinase. The other pair of plasmids, Plasmid D and Plasmid E, are constructed to contain the FRT (wild type) site for FLP, and a second mutant FRT site (SEQ ID NO:40), which differs from the FRT wild type site in 3 out of 30 bases total. In this example, each plasmid comprises a set of functional recombination sites wherein the recombination sites are dissimilar and non-recombinogenic with respect to one another.

Buffers:

Various known buffers can be used in the reactions. For restriction enzymes, it is advisable to use the buffers recommended by the manufacturer. Alternative buffers can be readily found in the literature or can be devised by those of ordinary skill in the art. One exemplary buffer for lambda integrase comprises 50 mM Tris-HCl, at pH 7.5-7.8, 70 mM KCl, 5 mM spermidine, 0.5 mM EDTA, and 0.25 mg/ml bovine serum albumin, and optionally, 10% glycerol. An exemplary buffer for P1 Cre recombinase comprises 50 mM Tris-HCl at pH 7.5, 33 mM NaCl, 5 mM spermidine, and 0.5 mg/ml bovine serum albumin and an exemplary buffer for FLP is discussed above in Example 2. An exemplary buffer for Cre and FLP recombinases comprises 50 mM Tris-HCL at pH 7.5, 70 mM NaCl, 2 mM $MgCl_2$, and 0.1 mg/ml BSA, (Buchholz et al. (1996) *Nucleic Acids Res.* 24:4256-4262). The buffer for other site-specific recombinases are either known in the art or can be determined empirically by the skilled artisans, particularly in light of the above-described buffers.

A. Recombinational Cloning Using FLP Recombinase

Two plasmids are constructed. The donor plasmid (plasmid A) comprises in the following order: a wild type FRT site, a constitutive drug marker (chloramphenicol resistance), an origin of replication, a constitutively expressed gene for the tet repressor protein (tetR), a FRT 5 site, and a conditional drug marker (kanamycin resistance whose expression is controlled by the operator/promoter of the tetracycline resistance operon of transposon Tn10). *E. coli* cells containing plasmid A are resistant to chloramphenicol at 30 µg/ml, but sensitive to kanamycin at 100 µg/ml.

The insert donor plasmid (plasmid B) comprises in the following order: the wild type FRT site, a different drug marker (ampicillin resistance), the FRT 5 site, an origin, and a multiple cloning site.

About 75 ng each of plasmid A and B are mixed in a total volume of 30 µl of FLP reaction buffer. Two 10 µl aliquots are transferred to new tubes. One tube receives FLP protein. Both tubes are incubated at 37° C. for 30 minutes, then 70° C. for 10 minutes. Aliquots of each reaction are diluted and transformed into DH5α. Following expression, aliquots are plated on 30 µg/ml chloramphenicol; 100 µg/ml ampicillin plus 200 µg/ml methicillin; or 100 µg/ml kanamycin.

Colonies that are chloramphenicol resistant, ampicillin resistant, and kanamycin sensitive under went the recombination reaction and comprise the newly generated product vector (plasmid C). Plasmid C comprises in the following order: the wild type FRT site, the constitutive drug marker (chloramphenicol resistance), the origin of replication, the constitutively expressed gene for the tet repressor protein (tetR), the FRT 5 site, and the ampicillin resistance marker.

To confirm the structure of the product vector (plasmid C), colonies that are chloramphenicol resistant, ampicillin resistant, and kanamycin sensitive are picked and inoculated into medium containing 100 µg/ml kanamycin. Minipreps are performed and the miniprep DNAs are cut with the appropriate restriction enzymes and electrophoresed.

Plasmid C can be identified by based on the size predicted for the Product plasmid and the resulting fragments of the restriction enzyme digest.

B. Recombinational Cloning Using FLP Recombinase and Cre Recombinase

The plasmids of this method are analogous to those above, except that Plasmid D, the vector donor plasmid, contains a loxP site in place of the wild type FRT site, and Plasmid E, the insert donor plasmid, contains the loxP site in place of the wild type FRT site.

About 500 ng of Plasmid E and Plasmid D are ethanol precipitated and resuspended in 40 µl buffer Cre/FLP reaction buffer (described above). Reactions are incubated at 37° C. for 30 minutes and then at 70° C. for 10 minutes. TE buffer (90 µl; TE: 10 mM Tris-HCl, pH 7.5, 1 mM EDTA) is added to each reaction, and 1 µl each is transformed into *E. coli* DH5α. The transformation mixtures are plated on 100 µg/ml ampicillin plus 200 µg/ml methicillin; 30 µg/ml chloramphenicol; or 100 µg/ml kanamycin.

Colonies that are chloramphenicol resistant, ampicillin resistant, and kanamycin sensitive under went the recombination reaction and comprise the newly generated product vector (plasmid F). Plasmid F comprises in the following order: the wild type loxP site, the constitutive drug marker (chloramphenicol resistance), the origin of replication, the constitutively expressed gene for the tet repressor protein (tetR), the FRT 5 site, and the ampicillin resistance marker.

To confirm the structure of the product vector (plasmid F), colonies that are chloramphenicol resistant, ampicillin resistant, and kanamycin sensitive are picked and inoculated into medium containing 100 µg/ml kanamycin. Minipreps are performed and the miniprep DNAs are cut with the appropriate restriction enzymes and electrophoresed. Plasmid F can be identified by based on the size predicted for the Product plasmid and the resulting fragments of the restriction enzyme digest.

C. In vitro Recombinational Cloning to Subclone the Chloramphenicol Acetyl Transferase Gene into a Vector for Expression in Eukaryotic Cells An insert donor plasmid, Plasmid G, is constructed, comprising in the following order: a wild type FRT site, a chloramphenicol acetyl transferase gene of *E. coli* lacking a promoter, the FRT 5 site, an origin of replication, and a constitutive drug marker (ampicillin resistance).

A vector donor plasmid, Plasmid H, is constructed, which comprises in the following order: kanamycin resistance gene, origin of replication, the cytomegalovirus eukaryotic promoter, a wild type FRT site, the constitutively expressed gene for the tet repressor protein (tetR), a chloramphenicol resistance gene, and the FRT 5 site. One microliter aliquots of each plasmid, typically about 50 ng crude miniprep DNA, are combined in a 10 µl reaction containing a FLP reaction buffer and FLP recombinase. After incubation at 30° C. for 30 minutes and 75° C. for 10 minutes, one microliter is transformed into competent *E. coli* strain DH5α (Life Technologies, Inc.). Aliquots of transformations are spread on agar plates containing 200 µg/ml kanamycin and incubated at 37° C. overnight. An otherwise identical control reaction contains the vector donor plasmid only.

To confirm the structure of the product vector (plasmid 1), minipreps are performed and the miniprep DNAs are cut with the appropriate restriction enzymes and electrophoresed. Plasmid I can be identified by based on the size predicted for the product plasmid and the resulting fragments of the restriction enzyme digest to confirm the chloramphenicol acetyl transferase is cloned downstream of the CMV promoter.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

The article "a" and "an" are used herein to refer to one or more than one (i.e., to at least one) of the grammatical object of the article. By way of example, "an element" means one or more than one element.

The invention claimed is:

1. An isolated polynucleotide comprising a nucleotide sequence comprising at least a first FRT recombination site, the first FRT recombination site comprises the spacer sequence of SEQ ID NO: 1.

2. The polynucleotide of claim 1, wherein the FRT recombination site comprises SEQ ID NO:21.

3. The isolated polynucleotide of claim 1, wherein the polynucleotide further comprises a second recombination site.

4. The isolated polynucleotide of claim 3, wherein the second recombination site is selected from the group consisting of a FRT site, a LOX site, and an att site.

5. The isolated polynucleotide of claim 4, wherein the FRT site is selected from the group consisting of a wild type FRT site or a modified FRT site, and the LOX site is selected from the group consisting of a wild type LOX site, and a modified LOX site, and the att site is selected from the group consisting of a wild type att site, and a modified att site.

6. The isolated polynucleotide of claim 4, wherein the second recombination site comprises a polynucleotide the polynucleotide of SEQ ID NO: 4.

7. The isolated polynucleotide of claim 3, wherein the second recombination site is dissimilar and non-recombinogenic with respect to the first FRT recombination site.

8. The isolated polynucleotide of claim 3, wherein the first FRT recombination site and the second recombination site are corresponding recombination sites.

9. A cell comprising the polynucleotide of claim 1.

10. The cell of claim 9, wherein the cell is from a plant.

11. The cell of claim 9, wherein the polynucleotide is stably integrated into the genome of the cell.

12. The cell of claim 10, wherein the cell is from a monocotyledonous plant or a dicotyledonous plant.

13. The cell of claim 12, wherein the plant cell is from maize, barley, millet, wheat, rice, sorghum, rye, soybean, canola, alfalfa, sunflower, safflower, tobacco, *Arabidopsis*, or cotton.

14. A plant comprising the cell of claim 10.

15. A seed having stably integrated into its genome the polynucleotide of claim 1.

16. The cell of claim 9, wherein the cell further has stably incorporated into its genome a nucleic acid molecule encoding a FLP recombinase.

17. The cell of claim 16, wherein the nucleic acid molecule encodes a biologically active variant of the FLP recombinase.

18. The isolated polynucleotide of claim 3, wherein the polynucleotide comprises a first convergent promoter, the first recombination site, the second recombination site, and a second convergent promoter.

19. The isolated polynucleotide of claim 18, wherein the polynucleotide comprises the first convergent promoter, the first recombination site, a first polynucleotide sequence of interest operably linked to the first convergent promoter, a second polynucleotide of interest operably linked to the second convergent promoter, the second recombination site, and the second convergent promoter.

* * * * *

```
                              SEQUENCE LISTING

<160> NUMBER OF SEQ ID NOS: 72

<210> SEQ ID NO 1
<211> LENGTH: 8
<212> TYPE: DNA
<213> ORGANISM: Artificial Sequence
<220> FEATURE:
<223> OTHER INFORMATION: Novel FRT spacer sequence of FRT 12 site

<400> SEQUENCE: 1 tctatgta                                                                 8

<210> SEQ ID NO 2
<211> LENGTH: 8
<212> TYPE: DNA
<213> ORGANISM: Artificial Sequence
<220> FEATURE:
<223> OTHER INFORMATION: Novel FRT spacer sequence of FRT 57 site

<400> SEQUENCE: 2 ttttctaa                                                                 8

<210> SEQ ID NO 3
<211> LENGTH: 8
<212> TYPE: DNA
<213> ORGANISM: Artificial Sequence
<220> FEATURE:
<223> OTHER INFORMATION: Novel FRT spacer sequence of FRT 85 site

<400> SEQUENCE: 3 tttcttga                                                                 8

<210> SEQ ID NO 4
<211> LENGTH: 8
<212> TYPE: DNA
<213> ORGANISM: Artificial Sequence
<220> FEATURE:
<223> OTHER INFORMATION: Novel FRT spacer sequence of FRT 87 site

<400> SEQUENCE: 4 tttctgga                                                                 8

<210> SEQ ID NO 5
<211> LENGTH: 8
<212> TYPE: DNA
<213> ORGANISM: Artificial Sequence
<220> FEATURE:
<223> OTHER INFORMATION: Novel FRT spacer sequence of FRT 53 site

<400> SEQUENCE: 5 tgtaaaaa                                                                 8

<210> SEQ ID NO 6
<211> LENGTH: 8
```

```
<212> TYPE: DNA
<213> ORGANISM: Artificial Sequence
<220> FEATURE:
<223> OTHER INFORMATION: Novel FRT spacer sequence of FRT 62 site

<400> SEQUENCE: 6 tttaggta                                                             8

<210> SEQ ID NO 7
<211> LENGTH: 8
<212> TYPE: DNA
<213> ORGANISM: Artificial Sequence
<220> FEATURE:
<223> OTHER INFORMATION: Novel FRT spacer sequence of FRT 78 site

<400> SEQUENCE: 7 tgaaaaga                                                             8

<210> SEQ ID NO 8
<211> LENGTH: 8
<212> TYPE: DNA
<213> ORGANISM: Artificial Sequence
<220> FEATURE:
<223> OTHER INFORMATION: Novel FRT spacer sequence of FRT 34 site

<400> SEQUENCE: 8 tgtaatga                                                             8

<210> SEQ ID NO 9
<211> LENGTH: 8
<212> TYPE: DNA
<213> ORGANISM: Artificial Sequence
<220> FEATURE:
<223> OTHER INFORMATION: Novel FRT spacer sequence of FRT 70 site

<400> SEQUENCE: 9 tatacaaa                                                             8

<210> SEQ ID NO 10
<211> LENGTH: 8
<212> TYPE: DNA
<213> ORGANISM: Artificial Sequence
<220> FEATURE:
<223> OTHER INFORMATION: Novel FRT spacer sequence of FRT 76 site

<400> SEQUENCE: 10 ttccataa                                                             8

<210> SEQ ID NO 11
<211> LENGTH: 8
<212> TYPE: DNA
<213> ORGANISM: Artificial Sequence
<220> FEATURE:
<223> OTHER INFORMATION: Novel FRT spacer sequence of FRT 89 site

<400> SEQUENCE: 11 tctctaga                                                             8

<210> SEQ ID NO 12
<211> LENGTH: 8
<212> TYPE: DNA
<213> ORGANISM: Artificial Sequence
<220> FEATURE:
<223> OTHER INFORMATION: Novel FRT spacer sequence of FRT 43 site

<400> SEQUENCE: 12
```

```
ttccgaga                                                              8

<210> SEQ ID NO 13
<211> LENGTH: 8
<212> TYPE: DNA
<213> ORGANISM: Artificial Sequence
<220> FEATURE:
<223> OTHER INFORMATION: Novel FRT spacer sequence of FRT 45 site

<400> SEQUENCE: 13 tctcttga                                                              8

<210> SEQ ID NO 14
<211> LENGTH: 8
<212> TYPE: DNA
<213> ORGANISM: Artificial Sequence
<220> FEATURE:
<223> OTHER INFORMATION: Novel FRT spacer sequence of FRT 55 site

<400> SEQUENCE: 14 tccacaga                                                              8

<210> SEQ ID NO 15
<211> LENGTH: 8
<212> TYPE: DNA
<213> ORGANISM: Artificial Sequence
<220> FEATURE:
<223> OTHER INFORMATION: Novel FRT spacer sequence of FRT 65 site

<400> SEQUENCE: 15 tgattgga                                                              8

<210> SEQ ID NO 16
<211> LENGTH: 8
<212> TYPE: DNA
<213> ORGANISM: Artificial Sequence
<220> FEATURE:
<223> OTHER INFORMATION: Novel FRT spacer sequence of FRT 69 site

<400> SEQUENCE: 16 ttttgtga                                                              8

<210> SEQ ID NO 17
<211> LENGTH: 8
<212> TYPE: DNA
<213> ORGANISM: Artificial Sequence
<220> FEATURE:
<223> OTHER INFORMATION: Novel FRT spacer sequence of FRT 74 site

<400> SEQUENCE: 17 tgagagaa                                                              8

<210> SEQ ID NO 18
<211> LENGTH: 8
<212> TYPE: DNA
<213> ORGANISM: Artificial Sequence
<220> FEATURE:
<223> OTHER INFORMATION: Novel FRT spacer sequence of FRT 86 site

<400> SEQUENCE: 18 tttctcga                                                              8

<210> SEQ ID NO 19
<211> LENGTH: 11
<212> TYPE: DNA
<213> ORGANISM: Artificial Sequence
```

```
<220> FEATURE:
<223> OTHER INFORMATION: 5' FLP binding site (symmetry element) of
      wildtype FRT site

<400> SEQUENCE: 19
agttcctata c                                                             11

<210> SEQ ID NO 20
<211> LENGTH: 11
<212> TYPE: DNA
<213> ORGANISM: Artificial Sequence
<220> FEATURE:
<223> OTHER INFORMATION: 3' FLP binding site (symmetry element) of
      wildtype FRT site

<400> SEQUENCE: 20
gaataggaac t                                                             11

<210> SEQ ID NO 21
<211> LENGTH: 30
<212> TYPE: DNA
<213> ORGANISM: Artificial Sequence
<220> FEATURE:
<223> OTHER INFORMATION: Novel minimal FRT 12 site

<400> SEQUENCE: 21
agttcctata ctctatgtag aataggaact                                         30

<210> SEQ ID NO 22
<211> LENGTH: 30
<212> TYPE: DNA
<213> ORGANISM: Artificial Sequence
<220> FEATURE:
<223> OTHER INFORMATION: Novel minimal FRT 57 site

<400> SEQUENCE: 22
agttcctata cttttctaag aataggaact                                         30

<210> SEQ ID NO 23
<211> LENGTH: 30
<212> TYPE: DNA
<213> ORGANISM: Artificial Sequence
<220> FEATURE:
<223> OTHER INFORMATION: Novel minimal FRT 85 site

<400> SEQUENCE: 23
agttcctata ctttcttgag aataggaact                                         30

<210> SEQ ID NO 24
<211> LENGTH: 30
<212> TYPE: DNA
<213> ORGANISM: Artificial Sequence
<220> FEATURE:
<223> OTHER INFORMATION: Novel minimal FRT 87 site

<400> SEQUENCE: 24
agttcctata ctttctggag aataggaact                                         30

<210> SEQ ID NO 25
<211> LENGTH: 30
<212> TYPE: DNA
<213> ORGANISM: Artificial Sequence
<220> FEATURE:
<223> OTHER INFORMATION: Novel minimal FRT 53 site

<400> SEQUENCE: 25
```
agttcctata ctgtaaaaag aataggaact        30

<210> SEQ ID NO 26
<211> LENGTH: 30
<212> TYPE: DNA
<213> ORGANISM: Artificial Sequence
<220> FEATURE:
<223> OTHER INFORMATION: Novel minimal FRT 62 site

<400> SEQUENCE: 26
agttcctata ctttaggtag aataggaact        30

<210> SEQ ID NO 27
<211> LENGTH: 30
<212> TYPE: DNA
<213> ORGANISM: Artificial Sequence
<220> FEATURE:
<223> OTHER INFORMATION: Novel minimal FRT 78 site

<400> SEQUENCE: 27
agttcctata ctgaaaagag aataggaact        30

<210> SEQ ID NO 28
<211> LENGTH: 30
<212> TYPE: DNA
<213> ORGANISM: Artificial Sequence
<220> FEATURE:
<223> OTHER INFORMATION: Novel minimal FRT 34 site

<400> SEQUENCE: 28
agttcctata ctgtaatgag aataggaact        30

<210> SEQ ID NO 29
<211> LENGTH: 30
<212> TYPE: DNA
<213> ORGANISM: Artificial Sequence
<220> FEATURE:
<223> OTHER INFORMATION: Novel minimal FRT 70 site

<400> SEQUENCE: 29
agttcctata ctatacaaag aataggaact        30

<210> SEQ ID NO 30
<211> LENGTH: 30
<212> TYPE: DNA
<213> ORGANISM: Artificial Sequence
<220> FEATURE:
<223> OTHER INFORMATION: Novel minimal FRT 76 site

<400> SEQUENCE: 30
agttcctata cttccataag aataggaact        30

<210> SEQ ID NO 31
<211> LENGTH: 30
<212> TYPE: DNA
<213> ORGANISM: Artificial Sequence
<220> FEATURE:
<223> OTHER INFORMATION: Novel minimal FRT 89 site

<400> SEQUENCE: 31
agttcctata ctctctagag aataggaact        30

<210> SEQ ID NO 32
<211> LENGTH: 30
<212> TYPE: DNA
<213> ORGANISM: Artificial Sequence -continued

```
<220> FEATURE:
<223> OTHER INFORMATION: Novel minimal FRT 43 site

<400> SEQUENCE: 32
agttcctata cttccgagag aataggaact                                           30

<210> SEQ ID NO 33
<211> LENGTH: 30
<212> TYPE: DNA
<213> ORGANISM: Artificial Sequence
<220> FEATURE:
<223> OTHER INFORMATION: Novel minimal FRT 45 site

<400> SEQUENCE: 33
agttcctata ctctcttgag aataggaact                                           30

<210> SEQ ID NO 34
<211> LENGTH: 30
<212> TYPE: DNA
<213> ORGANISM: Artificial Sequence
<220> FEATURE:
<223> OTHER INFORMATION: Novel minimal FRT 55 site

<400> SEQUENCE: 34
agttcctata ctccacagag aataggaact                                           30

<210> SEQ ID NO 35
<211> LENGTH: 30
<212> TYPE: DNA
<213> ORGANISM: Artificial Sequence
<220> FEATURE:
<223> OTHER INFORMATION: Novel minimal FRT 65 site

<400> SEQUENCE: 35
agttcctata ctgattggag aataggaact                                           30

<210> SEQ ID NO 36
<211> LENGTH: 30
<212> TYPE: DNA
<213> ORGANISM: Artificial Sequence
<220> FEATURE:
<223> OTHER INFORMATION: Novel minimal FRT 69 site

<400> SEQUENCE: 36
agttcctata cttttgtgag aataggaact                                           30

<210> SEQ ID NO 37
<211> LENGTH: 30
<212> TYPE: DNA
<213> ORGANISM: Artificial Sequence
<220> FEATURE:
<223> OTHER INFORMATION: Novel minimal FRT 74 site

<400> SEQUENCE: 37
agttcctata ctgagagaag aataggaact                                           30

<210> SEQ ID NO 38
<211> LENGTH: 30
<212> TYPE: DNA
<213> ORGANISM: Artificial Sequence
<220> FEATURE:
<223> OTHER INFORMATION: Novel minimal FRT 86 site

<400> SEQUENCE: 38
agttcctata ctttctcgag aataggaact                                           30
```

```
<210> SEQ ID NO 39
<211> LENGTH: 30
<212> TYPE: DNA
<213> ORGANISM: Artificial Sequence
<220> FEATURE:
<223> OTHER INFORMATION: Minimal wildtype FRT site

<400> SEQUENCE: 39
agttcctata ctttctagag aataggaact                                30

<210> SEQ ID NO 40
<211> LENGTH: 30
<212> TYPE: DNA
<213> ORGANISM: Artificial Sequence
<220> FEATURE:
<223> OTHER INFORMATION: minimal mutant FRT5 site

<400> SEQUENCE: 40
agttcctata ctcttttgag aataggaact                                30

<210> SEQ ID NO 41
<211> LENGTH: 30
<212> TYPE: DNA
<213> ORGANISM: Artificial Sequence
<220> FEATURE:
<223> OTHER INFORMATION: Minimal mutant FRT6 site

<400> SEQUENCE: 41
agttcctata cttttgaag aataggaact                                 30

<210> SEQ ID NO 42
<211> LENGTH: 30
<212> TYPE: DNA
<213> ORGANISM: Artificial Sequence
<220> FEATURE:
<223> OTHER INFORMATION: Minimal mutant FRT7 site

<400> SEQUENCE: 42
agttcctata cttattgaag aataggaact                                30

<210> SEQ ID NO 43
<211> LENGTH: 8
<212> TYPE: DNA
<213> ORGANISM: Artificial Sequence
<220> FEATURE:
<223> OTHER INFORMATION: Spacer sequence of wildtype FRT recombination
      site

<400> SEQUENCE: 43 tttctaga                                                         8

<210> SEQ ID NO 44
<211> LENGTH: 8
<212> TYPE: DNA
<213> ORGANISM: Artificial Sequence
<220> FEATURE:
<223> OTHER INFORMATION: Spacer sequence of FRT 5 recombination site

<400> SEQUENCE: 44 cttttgaa                                                         8

<210> SEQ ID NO 45
<211> LENGTH: 1032
<212> TYPE: DNA
<213> ORGANISM: Bacteriophage C1
<220> FEATURE:
```

-continued

```
<221> NAME/KEY: CDS
<222> LOCATION: (1)...(1016)

<400> SEQUENCE: 45 atg tcc aat tta ctg acc gta cac caa aat ttg cct gca tta ccg gtc      48
Met Ser Asn Leu Leu Thr Val His Gln Asn Leu Pro Ala Leu Pro Val
 1               5                  10                  15 gat gca acg agt gat gag gtt cgc aag aac ctg atg gac atg ttc agg      96
Asp Ala Thr Ser Asp Glu Val Arg Lys Asn Leu Met Asp Met Phe Arg
             20                  25                  30 gat cgc cag gcg ttt tct gag cat acc tgg aaa atg ctt ctg tcc gtt     144
Asp Arg Gln Ala Phe Ser Glu His Thr Trp Lys Met Leu Leu Ser Val
         35                  40                  45 tgc cgg tcg tgg gcg gca tgg tgc aag ttg aat aac cgg aaa tgg ttt     192
Cys Arg Ser Trp Ala Ala Trp Cys Lys Leu Asn Asn Arg Lys Trp Phe
     50                  55                  60 ccc gca gaa cct gaa gat gtt cgc gat tat ctt cta tat ctt cag gcg     240
Pro Ala Glu Pro Glu Asp Val Arg Asp Tyr Leu Leu Tyr Leu Gln Ala
 65                  70                  75                  80 cgc ggt ctg gca gta aaa act atc cag caa cat ttg ggc cag cta aac     288
Arg Gly Leu Ala Val Lys Thr Ile Gln Gln His Leu Gly Gln Leu Asn
                 85                  90                  95 atg ctt cat cgt cgg tcc ggg ctg cca cga cca agt gac agc aat gct     336
Met Leu His Arg Arg Ser Gly Leu Pro Arg Pro Ser Asp Ser Asn Ala
            100                 105                 110 gtt tca ctg gtt atg cgg cgg atc cga aaa gaa aac gtt gat gcc ggt     384
Val Ser Leu Val Met Arg Arg Ile Arg Lys Glu Asn Val Asp Ala Gly
        115                 120                 125 gaa cgt gca aaa cag gct cta gcg ttc gaa cgc act gat ttc gac cag     432
Glu Arg Ala Lys Gln Ala Leu Ala Phe Glu Arg Thr Asp Phe Asp Gln
    130                 135                 140 gtt cgt tca ctc atg gaa aat agc gat cgc tgc cag gat ata cgt aat     480
Val Arg Ser Leu Met Glu Asn Ser Asp Arg Cys Gln Asp Ile Arg Asn
145                 150                 155                 160 ctg gca ttt ctg ggg att gct tat aac acc ctg tta cgt ata gcc gaa     528
Leu Ala Phe Leu Gly Ile Ala Tyr Asn Thr Leu Leu Arg Ile Ala Glu
                165                 170                 175 att gcc agg atc agg gtt aaa gat atc tca cgt act gac ggt ggg aga     576
Ile Ala Arg Ile Arg Val Lys Asp Ile Ser Arg Thr Asp Gly Gly Arg
            180                 185                 190 atg tta atc cat att ggc aga acg aaa acg ctg gtt agc acc gca ggt     624
Met Leu Ile His Ile Gly Arg Thr Lys Thr Leu Val Ser Thr Ala Gly
        195                 200                 205 gta gag aag gca ctt agc ctg ggg gta act aaa ctg gtc gag cga tgg     672
Val Glu Lys Ala Leu Ser Leu Gly Val Thr Lys Leu Val Glu Arg Trp
    210                 215                 220 att tcc gtc tct ggt gta gct gat gat ccg aat aac tac ctg ttt tgc     720
Ile Ser Val Ser Gly Val Ala Asp Asp Pro Asn Asn Tyr Leu Phe Cys
225                 230                 235                 240 cgg gtc aga aaa aat ggt gtt gcc gcg cca tct gcc acc agc cag cta     768
Arg Val Arg Lys Asn Gly Val Ala Ala Pro Ser Ala Thr Ser Gln Leu
                245                 250                 255 tca act cgc gcc ctg gaa ggg att ttt gaa gca act cat cga ttg att     816
Ser Thr Arg Ala Leu Glu Gly Ile Phe Glu Ala Thr His Arg Leu Ile
            260                 265                 270 tac ggc gct aag gat gac tct ggt cag aga tac ctg gcc tgg tct gga     864
Tyr Gly Ala Lys Asp Asp Ser Gly Gln Arg Tyr Leu Ala Trp Ser Gly
        275                 280                 285 cac agt gcc cgt gtc gga gcc gcg cga gat atg gcc cgc gct gga gtt     912
His Ser Ala Arg Val Gly Ala Ala Arg Asp Met Ala Arg Ala Gly Val
```

```
                290                 295                 300
tca ata ccg gag atc atg caa gct ggt ggc tgg acc aat gta aat att       960
Ser Ile Pro Glu Ile Met Gln Ala Gly Gly Trp Thr Asn Val Asn Ile
305                 310                 315                 320 gtc atg aac tat atc cgt aac ctg gat agt gaa aca ggg gca atg gtg      1008
Val Met Asn Tyr Ile Arg Asn Leu Asp Ser Glu Thr Gly Ala Met Val
                325                 330                 335 cgc ctg ct ggaagatggc gattag                                          1032
Arg Leu <210> SEQ ID NO 46
<211> LENGTH: 338
<212> TYPE: PRT
<213> ORGANISM: Bacteriophage C1

<400> SEQUENCE: 46

Met Ser Asn Leu Leu Thr Val His Gln Asn Leu Pro Ala Leu Pro Val
 1               5                  10                  15

Asp Ala Thr Ser Asp Glu Val Arg Lys Asn Leu Met Asp Met Phe Arg
                20                  25                  30

Asp Arg Gln Ala Phe Ser Glu His Thr Trp Lys Met Leu Leu Ser Val
            35                  40                  45

Cys Arg Ser Trp Ala Ala Trp Cys Lys Leu Asn Asn Arg Lys Trp Phe
 50                  55                  60

Pro Ala Glu Pro Glu Asp Val Arg Asp Tyr Leu Leu Tyr Leu Gln Ala
 65                  70                  75                  80

Arg Gly Leu Ala Val Lys Thr Ile Gln Gln His Leu Gly Gln Leu Asn
                85                  90                  95

Met Leu His Arg Arg Ser Gly Leu Pro Arg Pro Ser Asp Ser Asn Ala
            100                 105                 110

Val Ser Leu Val Met Arg Arg Ile Arg Lys Glu Asn Val Asp Ala Gly
        115                 120                 125

Glu Arg Ala Lys Gln Ala Leu Ala Phe Glu Arg Thr Asp Phe Asp Gln
130                 135                 140

Val Arg Ser Leu Met Glu Asn Ser Asp Arg Cys Gln Asp Ile Arg Asn
145                 150                 155                 160

Leu Ala Phe Leu Gly Ile Ala Tyr Asn Thr Leu Leu Arg Ile Ala Glu
                165                 170                 175

Ile Ala Arg Ile Arg Val Lys Asp Ile Ser Arg Thr Asp Gly Gly Arg
            180                 185                 190

Met Leu Ile His Ile Gly Arg Thr Lys Thr Leu Val Ser Thr Ala Gly
        195                 200                 205

Val Glu Lys Ala Leu Ser Leu Gly Val Thr Lys Leu Val Glu Arg Trp
210                 215                 220

Ile Ser Val Ser Gly Val Ala Asp Asp Pro Asn Asn Tyr Leu Phe Cys
225                 230                 235                 240

Arg Val Arg Lys Asn Gly Val Ala Ala Pro Ser Ala Thr Ser Gln Leu
                245                 250                 255

Ser Thr Arg Ala Leu Glu Gly Ile Phe Glu Ala Thr His Arg Leu Ile
            260                 265                 270

Tyr Gly Ala Lys Asp Asp Ser Gly Gln Arg Tyr Leu Ala Trp Ser Gly
        275                 280                 285

His Ser Ala Arg Val Gly Ala Ala Arg Asp Met Ala Arg Ala Gly Val
290                 295                 300

Ser Ile Pro Glu Ile Met Gln Ala Gly Gly Trp Thr Asn Val Asn Ile
```

-continued

```
                305                 310                 315                 320
Val Met Asn Tyr Ile Arg Asn Leu Asp Ser Glu Thr Gly Ala Met Val
                    325                 330                 335

Arg Leu

<210> SEQ ID NO 47
<211> LENGTH: 1032
<212> TYPE: DNA
<213> ORGANISM: Artificial Sequence
<220> FEATURE:
<223> OTHER INFORMATION: Nucleotide sequence encoding Cre protein from
      Bacteriophage P1 having maize preferred codons
      (moCRE)
<220> FEATURE:
<221> NAME/KEY: CDS
<222> LOCATION: (1)...(1032)

<400> SEQUENCE: 47 atg tcc aac ctg ctc acg gtt cac cag aac ctt ccg gct ctt cca gtg        48
Met Ser Asn Leu Leu Thr Val His Gln Asn Leu Pro Ala Leu Pro Val
 1               5                  10                  15 gac gcg acg tcc gat gaa gtc agg aag aac ctc atg gac atg ttc cgc        96
Asp Ala Thr Ser Asp Glu Val Arg Lys Asn Leu Met Asp Met Phe Arg
             20                  25                  30 gac agg caa gcg ttc agc gag cac acc tgg aag atg ctg ctc tcc gtc       144
Asp Arg Gln Ala Phe Ser Glu His Thr Trp Lys Met Leu Leu Ser Val
         35                  40                  45 tgc cgc tcc tgg gct gca tgg tgc aag ctg aac aac agg aag tgg ttc       192
Cys Arg Ser Trp Ala Ala Trp Cys Lys Leu Asn Asn Arg Lys Trp Phe
     50                  55                  60 ccc gct gag ccc gag gac gtg agg gat tac ctt ctg tac ctg caa gct       240
Pro Ala Glu Pro Glu Asp Val Arg Asp Tyr Leu Leu Tyr Leu Gln Ala
 65                  70                  75                  80 cgc ggg ctg gca gtg aag acc atc cag caa cac ctt gga caa ctg aac       288
Arg Gly Leu Ala Val Lys Thr Ile Gln Gln His Leu Gly Gln Leu Asn
                 85                  90                  95 atg ctt cac agg cgc tcc ggc ctc ccg cgc ccc agc gac tcg aac gcc       336
Met Leu His Arg Arg Ser Gly Leu Pro Arg Pro Ser Asp Ser Asn Ala
            100                 105                 110 gtg agc ctc gtc atg cgc cgc atc agg aag gaa aac gtc gat gcc ggc       384
Val Ser Leu Val Met Arg Arg Ile Arg Lys Glu Asn Val Asp Ala Gly
        115                 120                 125 gaa agg gca aag cag gcc ctc gcg ttc gag agg acc gat ttc gac cag       432
Glu Arg Ala Lys Gln Ala Leu Ala Phe Glu Arg Thr Asp Phe Asp Gln
    130                 135                 140 gtc cgc agc ctg atg gag aac agc gac agg tgc cag gac att agg aac       480
Val Arg Ser Leu Met Glu Asn Ser Asp Arg Cys Gln Asp Ile Arg Asn
145                 150                 155                 160 ctg gcg ttc ctc gga att gca tac aac acg ctc ctc agg atc gcg gaa       528
Leu Ala Phe Leu Gly Ile Ala Tyr Asn Thr Leu Leu Arg Ile Ala Glu
                165                 170                 175 att gcc cgc att cgc gtg aag gac att agc cgc acc gac ggc ggc agg       576
Ile Ala Arg Ile Arg Val Lys Asp Ile Ser Arg Thr Asp Gly Gly Arg
            180                 185                 190 atg ctt atc cac att ggc agg acc aag acg ctc gtt tcc acc gca ggc       624
Met Leu Ile His Ile Gly Arg Thr Lys Thr Leu Val Ser Thr Ala Gly
        195                 200                 205 gtc gaa aag gcc ctc agc ctc gga gtg acc aag ctc gtc gaa cgc tgg       672
Val Glu Lys Ala Leu Ser Leu Gly Val Thr Lys Leu Val Glu Arg Trp
    210                 215                 220 atc tcc gtg tcc ggc gtc gcg gac gac cca aac aac tac ctc ttc tgc       720
```

-continued

```
Ile Ser Val Ser Gly Val Ala Asp Asp Pro Asn Asn Tyr Leu Phe Cys
225                 230                 235                 240 cgc gtc cgc aag aac ggg gtg gct gcc cct agc gcc acc agc caa ctc     768
Arg Val Arg Lys Asn Gly Val Ala Ala Pro Ser Ala Thr Ser Gln Leu
                245                 250                 255 agc acg agg gcc ttg gaa ggt att ttc gag gcc acc cac cgc ctg atc     816
Ser Thr Arg Ala Leu Glu Gly Ile Phe Glu Ala Thr His Arg Leu Ile
            260                 265                 270 tac ggc gcg aag gat gac agc ggt caa cgc tac ctc gca tgg tcc ggg     864
Tyr Gly Ala Lys Asp Asp Ser Gly Gln Arg Tyr Leu Ala Trp Ser Gly
        275                 280                 285 cac tcc gcc cgc gtt gga gct gct agg gac atg gcc cgc gcc ggt gtt     912
His Ser Ala Arg Val Gly Ala Ala Arg Asp Met Ala Arg Ala Gly Val
    290                 295                 300 tcc atc ccc gaa atc atg cag gcg ggt gga tgg acg aac gtg aac att     960
Ser Ile Pro Glu Ile Met Gln Ala Gly Gly Trp Thr Asn Val Asn Ile
305                 310                 315                 320 gtc atg aac tac att cgc aac ctt gac agc gag acg ggc gca atg gtt    1008
Val Met Asn Tyr Ile Arg Asn Leu Asp Ser Glu Thr Gly Ala Met Val
                325                 330                 335 cgc ctc ctg gaa gat ggt gac tga                                    1032
Arg Leu Leu Glu Asp Gly Asp *
            340

<210> SEQ ID NO 48
<211> LENGTH: 1260
<212> TYPE: DNA
<213> ORGANISM: Saccharomyces cerevisiae
<220> FEATURE:
<221> NAME/KEY: CDS
<222> LOCATION: (1)...(1260)

<400> SEQUENCE: 48 atg cca caa ttt ggt ata tta tgt aaa aca cca cct aag gtg ctt gtt      48
Met Pro Gln Phe Gly Ile Leu Cys Lys Thr Pro Pro Lys Val Leu Val
1               5                   10                  15 cgt cag ttt gtg gaa agg ttt gaa aga cct tca ggt gag aaa ata gca      96
Arg Gln Phe Val Glu Arg Phe Glu Arg Pro Ser Gly Glu Lys Ile Ala
            20                  25                  30 tta tgt gct gct gaa cta acc tat tta tgt tgg atg att aca cat aac     144
Leu Cys Ala Ala Glu Leu Thr Tyr Leu Cys Trp Met Ile Thr His Asn
        35                  40                  45 gga aca gca atc aag aga gcc aca ttc atg agc tat aat act atc ata     192
Gly Thr Ala Ile Lys Arg Ala Thr Phe Met Ser Tyr Asn Thr Ile Ile
    50                  55                  60 agc aat tcg ctg agt ttc gat att gtc aat aaa tca ctc cag ttt aaa     240
Ser Asn Ser Leu Ser Phe Asp Ile Val Asn Lys Ser Leu Gln Phe Lys
65                  70                  75                  80 tac aag acg caa aaa gca aca att ctg gaa gcc tca tta aag aaa ttg     288
Tyr Lys Thr Gln Lys Ala Thr Ile Leu Glu Ala Ser Leu Lys Lys Leu
                85                  90                  95 att cct gct tgg gaa ttt aca att att cct tac tat gga caa aaa cat     336
Ile Pro Ala Trp Glu Phe Thr Ile Ile Pro Tyr Tyr Gly Gln Lys His
            100                 105                 110 caa tct gat atc act gat att gta agt agt ttg caa tta cag ttc gaa     384
Gln Ser Asp Ile Thr Asp Ile Val Ser Ser Leu Gln Leu Gln Phe Glu
        115                 120                 125 tca tcg gaa gaa gca gat aag gga aat agc cac agt aaa aaa atg ctt     432
Ser Ser Glu Glu Ala Asp Lys Gly Asn Ser His Ser Lys Lys Met Leu
    130                 135                 140 aaa gca ctt cta agt gag ggt gaa agc atc tgg gag atc act gag aaa     480
```

| | | | | | | | | | | | | | | |
|---|---|---|---|---|---|---|---|---|---|---|---|---|---|---|
| Lys | Ala | Leu | Leu | Ser | Glu | Gly | Glu | Ser | Ile | Trp | Glu | Ile | Thr | Glu | Lys |
| 145 | | | | | 150 | | | | | 155 | | | | | 160 |

```
ata cta aat tcg ttt gag tat act tcg aga ttt aca aaa aca aaa act      528
Ile Leu Asn Ser Phe Glu Tyr Thr Ser Arg Phe Thr Lys Thr Lys Thr
            165                 170                 175 tta tac caa ttc ctc ttc cta gct act ttc atc aat tgt gga aga ttc      576
Leu Tyr Gln Phe Leu Phe Leu Ala Thr Phe Ile Asn Cys Gly Arg Phe
            180                 185                 190 agc gat att aag aac gtt gat ccg aaa tca ttt aaa tta gtc caa aat      624
Ser Asp Ile Lys Asn Val Asp Pro Lys Ser Phe Lys Leu Val Gln Asn
            195                 200                 205 aag tat ctg gga gta ata atc cag tgt tta gtg aca gag aca aag aca      672
Lys Tyr Leu Gly Val Ile Ile Gln Cys Leu Val Thr Glu Thr Lys Thr
    210                 215                 220 agc gtt agt agg cac ata tac ttc ttt agc gca agg ggt agg atc gat      720
Ser Val Ser Arg His Ile Tyr Phe Phe Ser Ala Arg Gly Arg Ile Asp
225                 230                 235                 240 cca ctt gta tat ttg gat gaa ttt ttg agg aat tct gaa cca gtc cta      768
Pro Leu Val Tyr Leu Asp Glu Phe Leu Arg Asn Ser Glu Pro Val Leu
                245                 250                 255 aaa cga gta aat agg acc ggc aat tct tca agc aat aaa cag gaa tac      816
Lys Arg Val Asn Arg Thr Gly Asn Ser Ser Ser Asn Lys Gln Glu Tyr
                260                 265                 270 caa tta tta aaa gat aac tta gtc aga tcg tac aat aaa gct ttg aag      864
Gln Leu Leu Lys Asp Asn Leu Val Arg Ser Tyr Asn Lys Ala Leu Lys
                275                 280                 285 aaa aat gcg cct tat tca atc ttt gct ata aaa aat ggc cca aaa tct      912
Lys Asn Ala Pro Tyr Ser Ile Phe Ala Ile Lys Asn Gly Pro Lys Ser
290                 295                 300 cac att gga aga cat ttg atg acc tca ttt ctt tca atg aag ggc cta      960
His Ile Gly Arg His Leu Met Thr Ser Phe Leu Ser Met Lys Gly Leu
305                 310                 315                 320 acg gag ttg act aat gtt gtg gga aat tgg agc gat aag cgt gct tct     1008
Thr Glu Leu Thr Asn Val Val Gly Asn Trp Ser Asp Lys Arg Ala Ser
                325                 330                 335 gcc gtg gcc agg aca acg tat act cat cag ata aca gca ata cct gat     1056
Ala Val Ala Arg Thr Thr Tyr Thr His Gln Ile Thr Ala Ile Pro Asp
            340                 345                 350 cac tac ttc gca cta gtt tct cgg tac tat gca tat gat cca ata tca     1104
His Tyr Phe Ala Leu Val Ser Arg Tyr Tyr Ala Tyr Asp Pro Ile Ser
            355                 360                 365 aag gaa atg ata gca ttg aag gat gag act aat cca att gag gag tgg     1152
Lys Glu Met Ile Ala Leu Lys Asp Glu Thr Asn Pro Ile Glu Glu Trp
370                 375                 380 cag cat ata gaa cag cta aag ggt agt gct gaa gga agc ata cga tac     1200
Gln His Ile Glu Gln Leu Lys Gly Ser Ala Glu Gly Ser Ile Arg Tyr
385                 390                 395                 400 ccc gca tgg aat ggg ata ata tca cag gag gta cta gac tac ctt tca     1248
Pro Ala Trp Asn Gly Ile Ile Ser Gln Glu Val Leu Asp Tyr Leu Ser
                405                 410                 415 tcc tac ata aat                                                     1260
Ser Tyr Ile Asn
            420
```

<210> SEQ ID NO 49
<211> LENGTH: 420
<212> TYPE: PRT
<213> ORGANISM: Saccharomyces cerevisiae

<400> SEQUENCE: 49

-continued

```
Met Pro Gln Phe Gly Ile Leu Cys Lys Thr Pro Pro Lys Val Leu Val
 1               5                  10                  15

Arg Gln Phe Val Glu Arg Phe Glu Arg Pro Ser Gly Glu Lys Ile Ala
             20                  25                  30

Leu Cys Ala Ala Glu Leu Thr Tyr Leu Cys Trp Met Ile Thr His Asn
             35                  40                  45

Gly Thr Ala Ile Lys Arg Ala Thr Phe Met Ser Tyr Asn Thr Ile Ile
 50                  55                  60

Ser Asn Ser Leu Ser Phe Asp Ile Val Asn Lys Ser Leu Gln Phe Lys
 65                  70                  75                  80

Tyr Lys Thr Gln Lys Ala Thr Ile Leu Glu Ala Ser Leu Lys Lys Leu
             85                  90                  95

Ile Pro Ala Trp Glu Phe Thr Ile Pro Tyr Tyr Gly Gln Lys His
                100                 105                 110

Gln Ser Asp Ile Thr Asp Ile Val Ser Ser Leu Gln Leu Gln Phe Glu
             115                 120                 125

Ser Ser Glu Glu Ala Asp Lys Gly Asn Ser His Ser Lys Lys Met Leu
 130                 135                 140

Lys Ala Leu Leu Ser Glu Gly Glu Ser Ile Trp Glu Ile Thr Glu Lys
145                 150                 155                 160

Ile Leu Asn Ser Phe Glu Tyr Thr Ser Arg Phe Thr Lys Thr Lys Thr
                165                 170                 175

Leu Tyr Gln Phe Leu Phe Leu Ala Thr Phe Ile Asn Cys Gly Arg Phe
             180                 185                 190

Ser Asp Ile Lys Asn Val Asp Pro Lys Ser Phe Lys Leu Val Gln Asn
             195                 200                 205

Lys Tyr Leu Gly Val Ile Ile Gln Cys Leu Val Thr Glu Thr Lys Thr
 210                 215                 220

Ser Val Ser Arg His Ile Tyr Phe Phe Ser Ala Arg Gly Arg Ile Asp
225                 230                 235                 240

Pro Leu Val Tyr Leu Asp Glu Phe Leu Arg Asn Ser Glu Pro Val Leu
                245                 250                 255

Lys Arg Val Asn Arg Thr Gly Asn Ser Ser Ser Asn Lys Gln Glu Tyr
             260                 265                 270

Gln Leu Leu Lys Asp Asn Leu Val Arg Ser Tyr Asn Lys Ala Leu Lys
             275                 280                 285

Lys Asn Ala Pro Tyr Ser Ile Phe Ala Ile Lys Asn Gly Pro Lys Ser
 290                 295                 300

His Ile Gly Arg His Leu Met Thr Ser Phe Leu Ser Met Lys Gly Leu
305                 310                 315                 320

Thr Glu Leu Thr Asn Val Val Gly Asn Trp Ser Asp Lys Arg Ala Ser
                325                 330                 335

Ala Val Ala Arg Thr Thr Tyr Thr His Gln Ile Thr Ala Ile Pro Asp
             340                 345                 350

His Tyr Phe Ala Leu Val Ser Arg Tyr Tyr Ala Tyr Asp Pro Ile Ser
             355                 360                 365

Lys Glu Met Ile Ala Leu Lys Asp Glu Thr Asn Pro Ile Glu Glu Trp
 370                 375                 380

Gln His Ile Glu Gln Leu Lys Gly Ser Ala Glu Gly Ser Ile Arg Tyr
385                 390                 395                 400

Pro Ala Trp Asn Gly Ile Ile Ser Gln Glu Val Leu Asp Tyr Leu Ser
                405                 410                 415

Ser Tyr Ile Asn
```

<210> SEQ ID NO 50
<211> LENGTH: 1260
<212> TYPE: DNA
<213> ORGANISM: Artificial Sequence
<220> FEATURE:
<223> OTHER INFORMATION: Nucleotide sequence having maize preferred codons encoding FLP recombinase (FLPm)
<220> FEATURE:
<221> NAME/KEY: CDS
<222> LOCATION: (1)...(1260)

<400> SEQUENCE: 50

```
atg ccc cag ttc gac atc ctc tgc aag acc ccc ccc aag gtg ctc gtg      48
Met Pro Gln Phe Asp Ile Leu Cys Lys Thr Pro Pro Lys Val Leu Val
1               5                   10                  15 agg cag ttc gtg gag agg ttc gag agg ccc tcc ggc gag aag atc gcc      96
Arg Gln Phe Val Glu Arg Phe Glu Arg Pro Ser Gly Glu Lys Ile Ala
            20                  25                  30 ctc tgc gcc gcc gag ctc acc tac ctc tgc tgg atg atc acc cac aac     144
Leu Cys Ala Ala Glu Leu Thr Tyr Leu Cys Trp Met Ile Thr His Asn
        35                  40                  45 ggc acc gcc att aag agg gcc acc ttc atg tca tac aac acc atc atc     192
Gly Thr Ala Ile Lys Arg Ala Thr Phe Met Ser Tyr Asn Thr Ile Ile
    50                  55                  60 tcc aac tcc ctc tcc ttc gac atc gtg aac aag tcc ctc cag ttc aaa     240
Ser Asn Ser Leu Ser Phe Asp Ile Val Asn Lys Ser Leu Gln Phe Lys
65                  70                  75                  80 tac aag acc cag aag gcc acc atc ctc gag gcc tcc ctc aag aag ctc     288
Tyr Lys Thr Gln Lys Ala Thr Ile Leu Glu Ala Ser Leu Lys Lys Leu
                85                  90                  95 atc ccc gcc tgg gag ttc acc atc atc ccc tac tac ggc cag aag cac     336
Ile Pro Ala Trp Glu Phe Thr Ile Ile Pro Tyr Tyr Gly Gln Lys His
            100                 105                 110 cag tcc gac atc acc gac atc gtg tca tcc ctc cag ctt cag ttc gag     384
Gln Ser Asp Ile Thr Asp Ile Val Ser Ser Leu Gln Leu Gln Phe Glu
        115                 120                 125 tcc tcc gag gag gct gac aag ggc aac tcc cac tcc aag aag atg ctg     432
Ser Ser Glu Glu Ala Asp Lys Gly Asn Ser His Ser Lys Lys Met Leu
    130                 135                 140 aag gcc ctc ctc tcc gag ggc gag tcc atc tgg gag atc acc gag aag     480
Lys Ala Leu Leu Ser Glu Gly Glu Ser Ile Trp Glu Ile Thr Glu Lys
145                 150                 155                 160 atc ctc aac tcc ttc gag tac acc tcc agg ttc act aag acc aag acc     528
Ile Leu Asn Ser Phe Glu Tyr Thr Ser Arg Phe Thr Lys Thr Lys Thr
                165                 170                 175 ctc tac cag ttc ctc ttc ctc gcc acc ttc atc aac tgc ggc agg ttc     576
Leu Tyr Gln Phe Leu Phe Leu Ala Thr Phe Ile Asn Cys Gly Arg Phe
            180                 185                 190 tca gac atc aag aac gtg gac ccc aag tcc ttc aag ctc gtg cag aac     624
Ser Asp Ile Lys Asn Val Asp Pro Lys Ser Phe Lys Leu Val Gln Asn
        195                 200                 205 aag tac ctc ggc gtg atc atc cag tgc ctc gtg acc gag acc aag acc     672
Lys Tyr Leu Gly Val Ile Ile Gln Cys Leu Val Thr Glu Thr Lys Thr
    210                 215                 220 tcc gtg tcc agg cac atc tac ttc ttc tcc gct cgc ggc agg atc gac     720
Ser Val Ser Arg His Ile Tyr Phe Phe Ser Ala Arg Gly Arg Ile Asp
225                 230                 235                 240 ccc ctc gtg tac ctc gac gag ttc ctc agg aac tca gag ccc gtg ctc     768
Pro Leu Val Tyr Leu Asp Glu Phe Leu Arg Asn Ser Glu Pro Val Leu
                245                 250                 255
```

```
aag agg gtg aac agg acc ggc aac tcc tcc tcc aac aag cag gag tac      816
Lys Arg Val Asn Arg Thr Gly Asn Ser Ser Ser Asn Lys Gln Glu Tyr
        260                 265                 270 cag ctc ctc aag gac aac ctc gtg agg tcc tac aac aag gcc ctc aag      864
Gln Leu Leu Lys Asp Asn Leu Val Arg Ser Tyr Asn Lys Ala Leu Lys
    275                 280                 285 aag aac gcc ccc tac tcc atc ttc gcc atc aag aac ggc ccc aag tcc      912
Lys Asn Ala Pro Tyr Ser Ile Phe Ala Ile Lys Asn Gly Pro Lys Ser
290                 295                 300 cac atc ggt agg cac ctc atg acc tcc ttc ctc tca atg aag ggc ctc      960
His Ile Gly Arg His Leu Met Thr Ser Phe Leu Ser Met Lys Gly Leu
305                 310                 315                 320 acc gag ctc acc aac gtg gtg ggc aac tgg tcc gac aag agg gcc tcc     1008
Thr Glu Leu Thr Asn Val Val Gly Asn Trp Ser Asp Lys Arg Ala Ser
            325                 330                 335 gcc gtg gcc agg acc acc tac acc cac cag atc acc gcc atc ccc gac     1056
Ala Val Ala Arg Thr Thr Tyr Thr His Gln Ile Thr Ala Ile Pro Asp
        340                 345                 350 cac tac ttc gcc ctc gtg tca agg tac tac gcc tac gac ccc atc tcc     1104
His Tyr Phe Ala Leu Val Ser Arg Tyr Tyr Ala Tyr Asp Pro Ile Ser
    355                 360                 365 aag gag atg atc gcc ctc aag gac gag act aac ccc atc gag gag tgg     1152
Lys Glu Met Ile Ala Leu Lys Asp Glu Thr Asn Pro Ile Glu Glu Trp
370                 375                 380 cag cac atc gag cag ctc aag ggc tcc gcc gag ggc tcc atc agg tac     1200
Gln His Ile Glu Gln Leu Lys Gly Ser Ala Glu Gly Ser Ile Arg Tyr
385                 390                 395                 400 ccc gcc tgg aac ggc atc atc tcc cag gag gtg ctc gac tac ctc tcc     1248
Pro Ala Trp Asn Gly Ile Ile Ser Gln Glu Val Leu Asp Tyr Leu Ser
            405                 410                 415 tcc tac atc aac                                                     1260
Ser Tyr Ile Asn
            420

<210> SEQ ID NO 51
<211> LENGTH: 78
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: 38, 39, 40, 41, 42, 43
<223> OTHER INFORMATION: n = A,T,C or G

<400> SEQUENCE: 51
gccagcatgc aagcttgaat tccgaagttc ctatactnnn nnnagaatag gaacttcgag      60
atctggatcc gcggaacg                                                   78

<210> SEQ ID NO 52
<211> LENGTH: 78
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: 36, 37, 38, 39, 40, 41
<223> OTHER INFORMATION: n = A,T,C or G

<400> SEQUENCE: 52
cgttccgcgg atccagatct cgaagttcct attctnnnnn nagtatagga acttcggaat      60
```

-continued

```
tcaagcttgc atgctggc                                                   78

<210> SEQ ID NO 53
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 53
gcacatacaa atggacgaac gga                                             23

<210> SEQ ID NO 54
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 54
cctcttcgct attacgccag ct                                              22

<210> SEQ ID NO 55
<211> LENGTH: 8
<212> TYPE: DNA
<213> ORGANISM: Artificial Sequence
<220> FEATURE:
<223> OTHER INFORMATION: Spacer sequence of FRT6 site

<400> SEQUENCE: 55 tttttgaa                                                               8

<210> SEQ ID NO 56
<211> LENGTH: 8
<212> TYPE: DNA
<213> ORGANISM: Artificial Sequence
<220> FEATURE:
<223> OTHER INFORMATION: Spacer sequence of FRT7 site

<400> SEQUENCE: 56 ttattgaa                                                               8

<210> SEQ ID NO 57
<211> LENGTH: 8
<212> TYPE: DNA
<213> ORGANISM: Artificial Sequence
<220> FEATURE:
<223> OTHER INFORMATION: Spacer sequence of FRT22s site WO 01/23545

<400> SEQUENCE: 57 tatctaga                                                               8

<210> SEQ ID NO 58
<211> LENGTH: 8
<212> TYPE: DNA
<213> ORGANISM: Artificial Sequence
<220> FEATURE:
<223> OTHER INFORMATION: Spacer sequence of FRT72s site WO 01/23545

<400> SEQUENCE: 58 tttctaca                                                               8

<210> SEQ ID NO 59
<211> LENGTH: 8
<212> TYPE: DNA
<213> ORGANISM: Artificial Sequence
```

```
<220> FEATURE:
<223> OTHER INFORMATION: Spacer sequence of FRT3s site WO 01/23545

<400> SEQUENCE: 59 tatttgaa                                                                  8

<210> SEQ ID NO 60
<211> LENGTH: 8
<212> TYPE: DNA
<213> ORGANISM: Artificial Sequence
<220> FEATURE:
<223> OTHER INFORMATION: Spacer sequence of FRT2161s site WO 01/23545

<400> SEQUENCE: 60 tctctgga                                                                  8

<210> SEQ ID NO 61
<211> LENGTH: 8
<212> TYPE: DNA
<213> ORGANISM: Artificial Sequence
<220> FEATURE:
<223> OTHER INFORMATION: Spacer sequence of FRT2151s site WO 01/23545

<400> SEQUENCE: 61 tctccaga                                                                  8

<210> SEQ ID NO 62
<211> LENGTH: 8
<212> TYPE: DNA
<213> ORGANISM: Artificial Sequence
<220> FEATURE:
<223> OTHER INFORMATION: Spacer sequence of FRT2272s site WO 01/23545

<400> SEQUENCE: 62 tatctaca                                                                  8

<210> SEQ ID NO 63
<211> LENGTH: 8
<212> TYPE: DNA
<213> ORGANISM: Artificial Sequence
<220> FEATURE:
<223> OTHER INFORMATION: Spacer sequence of FRT2262s site WO 01/23545

<400> SEQUENCE: 63 tatcttga                                                                  8

<210> SEQ ID NO 64
<211> LENGTH: 8
<212> TYPE: DNA
<213> ORGANISM: Artificial Sequence
<220> FEATURE:
<223> OTHER INFORMATION: Spacer sequence of FRT2373s site WO 01/23545

<400> SEQUENCE: 64 tgtctata                                                                  8

<210> SEQ ID NO 65
<211> LENGTH: 30
<212> TYPE: DNA
<213> ORGANISM: Artificial Sequence
<220> FEATURE:
<223> OTHER INFORMATION: Minimal FRT f22 site WO 01/23545

<400> SEQUENCE: 65
agttcctata ctatctagag aataggaact                                         30
```

```
<210> SEQ ID NO 66
<211> LENGTH: 30
<212> TYPE: DNA
<213> ORGANISM: Artificial Sequence
<220> FEATURE:
<223> OTHER INFORMATION: Minimal FRT f72 site WO 01/23545

<400> SEQUENCE: 66
agttcctata ctttctacag aataggaact                                     30

<210> SEQ ID NO 67
<211> LENGTH: 30
<212> TYPE: DNA
<213> ORGANISM: Artificial Sequence
<220> FEATURE:
<223> OTHER INFORMATION: Minimal FRT f3 site WO 01/23545

<400> SEQUENCE: 67
agttcctata ctatttgaag aataggaact                                     30

<210> SEQ ID NO 68
<211> LENGTH: 30
<212> TYPE: DNA
<213> ORGANISM: Artificial Sequence
<220> FEATURE:
<223> OTHER INFORMATION: Minimal FRT f2161 site WO 01/23545

<400> SEQUENCE: 68
agttcctata ctctctggag aataggaact                                     30

<210> SEQ ID NO 69
<211> LENGTH: 30
<212> TYPE: DNA
<213> ORGANISM: Artificial Sequence
<220> FEATURE:
<223> OTHER INFORMATION: Minimal FRT f2151 site WO 01/23545

<400> SEQUENCE: 69
agttcctata ctctccagag aataggaact                                     30

<210> SEQ ID NO 70
<211> LENGTH: 30
<212> TYPE: DNA
<213> ORGANISM: Artificial Sequence
<220> FEATURE:
<223> OTHER INFORMATION: Minimal FRT f2272 site WO 01/23545

<400> SEQUENCE: 70
agttcctata ctatctacag aataggaact                                     30

<210> SEQ ID NO 71
<211> LENGTH: 30
<212> TYPE: DNA
<213> ORGANISM: Artificial Sequence
<220> FEATURE:
<223> OTHER INFORMATION: Minimal FRT f2262 site WO 01/23545

<400> SEQUENCE: 71
agttcctata ctatcttgag aataggaact                                     30

<210> SEQ ID NO 72
<211> LENGTH: 30
```

-continued

```
<212> TYPE: DNA
<213> ORGANISM: Artificial Sequence
<220> FEATURE:
<223> OTHER INFORMATION: Minimal FRT f2373 site WO 01/23545

<400> SEQUENCE: 72
agttcctata ctgtctatag aataggaact                                      30
```